(12) United States Patent
Tanimoto et al.

(10) Patent No.: US 6,933,317 B2
(45) Date of Patent: Aug. 23, 2005

(54) PGD$_2$ RECEPTOR ANTAGONISTIC PHARMACEUTICAL COMPOSITIONS

(75) Inventors: Norihiko Tanimoto, Osaka (JP); Yoshiharu Hiramatsu, Osaka (JP); Tsunetoshi Honma, Osaka (JP); Masanao Inagaki, Osaka (JP)

(73) Assignee: Shionogi & Co. Ltd., Osaka (JP)

( * ) Notice: Subject to any disclaimer, the term of this patent is extended or adjusted under 35 U.S.C. 154(b) by 220 days.

(21) Appl. No.: 10/399,605

(22) PCT Filed: Oct. 26, 2001

(86) PCT No.: PCT/JP01/09435

§ 371 (c)(1),
(2), (4) Date: Apr. 18, 2003

(87) PCT Pub. No.: WO02/36583

PCT Pub. Date: May 10, 2002

(65) Prior Publication Data

US 2004/0054003 A1 Mar. 18, 2004

(30) Foreign Application Priority Data

Nov. 1, 2000 (JP) ........................... 2000-334383

(51) Int. Cl.$^7$ ............... C07D 31/343; C07D 31/381; A61K 31/38; A61K 31/34
(52) U.S. Cl. ............ 514/443; 514/448; 514/469; 549/57; 549/467
(58) Field of Search ............ 549/57, 467; 514/448, 514/469, 443

(56) References Cited

U.S. PATENT DOCUMENTS

| | | | |
|---|---|---|---|
| 5,625,067 A | 4/1997 | Rehwinkel et al. | |
| 6,069,166 A | 5/2000 | Honma et al. | |
| 6,083,974 A | 7/2000 | Honma et al. | |
| 6,172,113 B1 | 1/2001 | Ohtani et al. | |
| 6,225,336 B1 | 5/2001 | Honma | |
| 6,384,075 B1 | 5/2002 | Ohtani et al. | |
| 6,498,190 B1 | 12/2002 | Ohtani et al. | |
| 2004/0024019 A1 | 2/2004 | Tanimoto et al. | |

FOREIGN PATENT DOCUMENTS

| | | |
|---|---|---|
| DE | 42 25 488 A1 | 2/1994 |
| EP | 0 945 450 A1 | 9/1999 |
| EP | 1 016 660 B1 | 7/2000 |
| EP | 1 295 872 A1 | 3/2003 |
| WO | WO 92/09573 | 6/1992 |
| WO | WO97/00853 | 1/1997 |
| WO | WO/9962555 | * 12/1999 |

OTHER PUBLICATIONS

Deike, P., et al., "Syntheses of New Metabolically Stabilized TXA$_2$/PGH$_2$–Receptor Antagonists and Their Biological Properties," *Bioorganic & Medicinal Chemistry Letters*, vol. 2, No. 9, pp. 1069–1072, 1992.

Hildebrand, M., "Pharmacokinetics of Iloprost and Cicaprost in Mice," *Protaglandins*, vol. 44, pp. 431–442, 1992.

Klar, U., et al., "Novel Protanoid Thromboxane A$_2$ Antagonists," *Bioorganic & Medicinal Chemistry Letters*, vol. 5, No. 12, pp. 1219–1224, 1995.

Skuballa, W., et al., "Synthesis of a New Chemically and Metabolically Stable Prostacyclin Analogue with High and Long–Lasting Oral Activity," *Journal of Medicinal Chemistry*, vol. 29, No. 3, pp. 313–315, Mar. 1986.

Sturzebecher, S., et al., "Pharmacological Profile of a Novel Carbacyclin Derivative with High Metabolic Stability and Oral Activity in the Rat," *Prostaglandins*, vol. 31:95, 1986.

* cited by examiner

*Primary Examiner*—Taofiq Solola
*Assistant Examiner*—Robin Waller
(74) *Attorney, Agent, or Firm*—Foley & Lardner LLP

(57) ABSTRACT

Compounds of the general formula (I) which are metabolically stable and have an antagonistic activity against PGD$_2$ receptor:

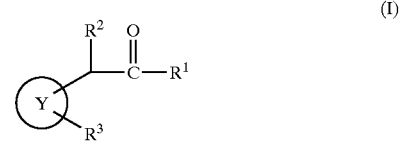

(I)

wherein Y is bicyclic ring; R$^1$ is optionally substituted heteroaryl; R$^2$ is hydrogen, etc.; R$^3$ is —CH$_2$—CH$_2$—CH$_2$—CH$_2$—CH=CH—COOR$^4$, —CH$_2$—CH$_2$—CH$_2$—CH$_2$—X$^1$—CH$_2$—COOR$^4$, —CH$_2$—CH=CH—CH$_2$—X$^1$—CH$_2$—COOR$^4$ or —CH$_2$—CH$_2$—CH$_2$—COOR$^4$; R$^4$ is hydrogen, etc.; X$^1$ is —O—, etc.

16 Claims, No Drawings

PGD₂ RECEPTOR ANTAGONISTIC PHARMACEUTICAL COMPOSITIONS

This application is the national phase of International Application No. PCT/JP01/09435, filed Oct. 26, 2001, published in a non-English language.

TECHNICAL FIELD

This invention relates to a bicyclic amide derivative, an antagonist against PGD₂ receptor, and a pharmaceutical composition comprising the same.

BACKGROUND ART

As a pharmaceutical composition comprising an antagonist against PGD₂ receptor, a compound of the formula:

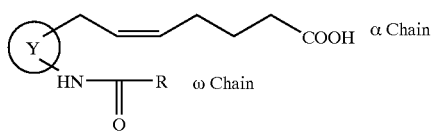

wherein Y is bicyclic ring and R is phenyl etc., was described in WO 97/00853 (International publication date: Jan. 1, 1997).

On the other hand, it was disclosed that 3-oxa-derivatives were prepared as metabolically stable $TXA_2/PGH_2$ receptor antagonists in Bioorganic & Medicinal Chemistry Letters, Vol. 2, No. 9, pp. 1069–1072, 1992. The active value of the compound was only described but the metabolic stability has not been described in the literature.

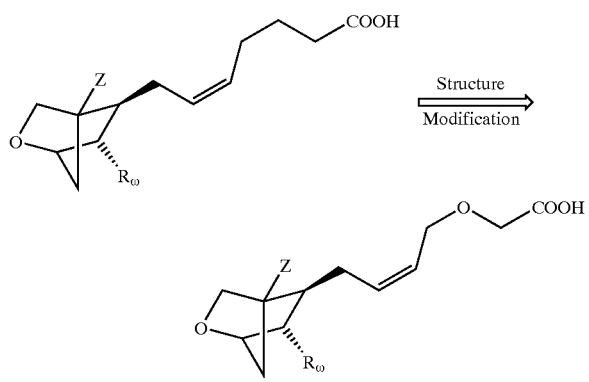

wherein, Z is p-fluorophenyl; Rω is benzenesulfonamino and the like.

Furthermore, it was reported in PROSTAGLANDINS, 1986, 31, 95 that ILOPROST, $PGI_2$ mimetics was stabilized metabolically by converting to the 3-oxa-derivative. But, remaining activity of each compound was only compared under a presence of the metabolic enzyme of a rat and the metabolic stability did not mentioned.

DISCLOSURE OF INVENTION

The present inventors have carried out the structure modification research on α chain of a pharmaceutical composition comprising an antagonist against PGD₂ receptor described in WO97/00853, found out a metabolically stable antagonist against PGD₂ receptor and have completed the present invention.

The present invention provides:
(1) a compound represented by the formula (I):

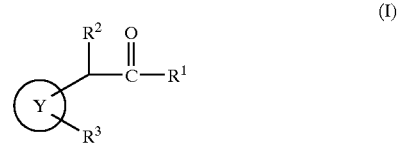

wherein

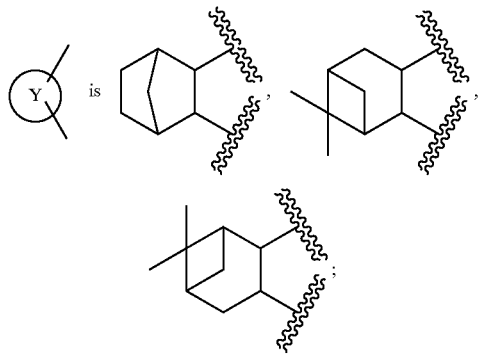

$R^1$ is optionally substituted heteroaryl;
$R^2$ is hydrogen or alkyl;
$R^3$ is $-CH_2-CH_2-CH_2-CH_2-CH=CH-COOR^4$, $-CH_2-CH_2-CH_2-CH_2-X^1-CH_2-COOR^4$, $-CH_2-CH=CH-CH_2-X^1-CH_2-COOR^4$ or $-CH_2-CH_2-CH_2-CH_2-COOR^4$;
$R^4$ is hydrogen or alkyl;
$X^1$ is $-O-$ or $-S-$,
a prodrug, a pharmaceutically acceptable salt or a solvate thereof,
(2) a compound as described in (1), wherein

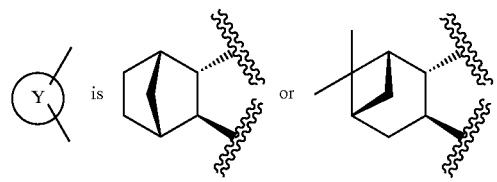

a prodrug, a pharmaceutically acceptable salt or a solvate thereof,
(3) a compound as described in (1) or (2), wherein $R^1$ is optionally substituted thienyl, optionally substituted benzothienyl, optionally substituted furyl, optionally substituted benzofuryl, optionally substituted pyrrolyl, optionally substituted thienopyrrolyl or optionally substituted indolyl, a prodrug, a pharmaceutically acceptable salt or a solvate thereof,
(4) a compound as described in (1) or (2), wherein $R^1$ is heteroaryl which may be substituted with a group of the formula: $-Z^1-Z^2$ wherein $Z^1$ is a bond, $-O-$, $-S-$, $-NH-$, $-NH-C(=O)-$, $-NH-C(=O)-O-$, $-NH-SO_2-$, $-C(=O)-$, $-O-C(=O)-$, $-C(=O)-O-$, $-SO_2-$, $-CH_2-O-$, $-CH_2-NH-C(=O)-$, $-CH_2-NH-C(=O)-O-$, $-CH_2-NH-SO_2-$ or $-CH_2-C(=O)-$ and $Z^2$ is alkyl or optionally substituted amino; carboxy; halogen; hydroxy; or nitro, a prodrug, a pharmaceutically acceptable salt or a solvate thereof, (5) a compound as described in any one of (1) to (4), wherein $R^3$ is —$CH_2$—$CH_2$—$CH_2$——$CH_2$—$CH_2$—$CH$=$CH$— $COOR^4$, —$CH_2$—$CH_2$—$CH_2$—$CH_2$—$X^1$—$CH_2$— $COOR^4$, —$CH_2$—$CH$=$CH$—$CH_2$—$X^1$—$CH_2$— $COOR^4$ or —$CH_2$—$CH_2$—$CH_2$—$CH_2$—$COOR^4$; $R^4$ is hydrogen; and $X^1$ is —O— or —S—, a prodrug, a pharmaceutically acceptable salt or a solvate thereof, (6) a compound as described in (5), wherein $R^3$ is —$CH_2$— $CH_2$—$CH_2$—$CH_2$—$CH$=$CH$—$COOR^4$ or —$CH_2$— $CH_2$—$CH_2$—$CH_2$—$X^1$—$CH_2$—$COOR^4$; $R^4$ is hydrogen; and $X^1$ is —O— or —S—, a prodrug, a pharmaceutically acceptable salt or a solvate thereof, (7) a pharmaceutical composition containing a compound, a prodrug, a pharmaceutically acceptable salt, or a solvate thereof as described in any one of (1) to (6), (8) a pharmaceutical composition having an antagonistic activity against $PGD_2$ receptor as described in (7), (9) a pharmaceutical composition as described in (7), which is used for the treatment of nasal,

(10) a pharmaceutical composition as described in (7), which is used for the treatment of allergic conjunctivitis,

(11) a pharmaceutical composition as described in (7), which is used for the treatment of allergic rhinitis,

(12) a method for treating nasal blockage, allergic conjunctivitis or allergic rhinitis, which comprises administrating a composition as described in (7), and

(13) use of the compound as described in any one of (1) to (6) for the preparation of a pharmaceutical composition for treating nasal blockage, allergic conjunctivitis or allergic rhinitis.

The terms used herein is explained below. Each term used herein is defined to have meanings below in either case of a single or a joint use with other terms.

The term "heteroaryl" includes a 5- to 7-membered aromatic heterocycle containing one or more oxygen atom, sulfur atom and/or nitrogen atom in the ring, or such an aromatic heterocycle as fused with one or more carbocycle or other aromatic heterocycle, which has a bond at any substitutable. Any one of aromatic heterocycle and aromatic carbocycle may have a bond.

Examples of "heteroaryl" include pyrrolyl (e.g., 2-pyrrolyl, 3-pyrrolyl), pyridyl (e.g., 2-pyridyl, 3-pyridyl, 4-pyridyl), pyrazolyl (e.g., 3-pyrazolyl, 4pyrazolyl), imidazolyl (e.g., 2-imidazolyl, 4-imidazolyl), pyrimidinyl (e.g., 2-pyrimidinyl, 4-pyrimidinyl, 5-pyrimidinyl), pyrazinyl (e.g., 2-pyrazinyl), indolyl (e.g., 1-indolyl, 2-indolyl, 3-indolyl, 4-indolyl, 5-indolyl, 6-indolyl, 7-indolyl), carbazolyl (e.g., 1-carbazolyl, 2-carbazolyl, 3-carbazolyl, 4-carbazolyl), benzimidazolyl (e.g., 2-benzimidazolyl, 4-benzimidazolyl, 5-benzimidazolyl), indazolyl (e.g., 3-indazolyl, 4-indazolyl, 5-indazolyl, 6-indazolyl, 7-indazolyl), quinolyl (e.g., 2-quinolyl, 3-quinolyl, 4-quinolyl, 5-quinolyl, 6-quinolyl, 7-quinolyl, 8-quinolyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), furyl (e.g., 2-furyl, 3-furyl), benzofuryl (e.g., 2-benzofuryl, 3-benzofuryl, 4-benzofuryl, 5-benzofuryl, 6-benzofuryl, 7-benzofuryl), thienyl (e.g., 2-thienyl, 3-thienyl), benzothienyl (e.g., benzo[b]thiophen-2-yl, benzo[b]thiophen-3-yl, benzo[b]thiophen-4-yl, benzo[b]thiophen-5-yl, benzo[b]thiophen-6-yl, benzo[b]thiophen-7-yl), dibenzothienyl (e.g., 2-dibenzothienyl, 3-dibenzothienyl), dibenzofuryl (e.g., 2-dibenzofuryl, 3-dibenzofuryl), naphthothienyl (e.g., naphtho[2,3-b]thiophen-2-yl, naphtho[2,3-b]thiophen-3-yl, naphtho[1.2-b]thiophen-2-yl, naphtho[1.2-b]thiophen-3-yl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), imidazothiazolyl (e.g., imidazo[2.1-b]thiazol-2-yl, imidazo[2.1-b]thiazol-3-yl), benzoisoxazolyl (e.g., benzo[d]isoxazol-3-yl), benzothiazolyl (e.g., benzo[d]thiazol-2-yl), thienopyrrolyl (e.g., thieno[2,3-b]pyrrole-2-yl, thieno[2,3-b]pyrrole-3-yl, thieno[2,3-b]pyrrole-5-yl, thieno[2,3-c]pyrrole-2-yl, thieno[2,3-c]pyrrole-4-yl, thieno[3,2-b]pyrrole-2-yl, thieno[3,2-b]pyrrole-3-yl, thieno[3,2-b]pyrrole-5-yl), and the like.

Thienyl, benzothienyl, furyl, benzofuryl, pyrrolyl, are indolyl preferred.

The term of "aromatic carbocycle or other aromatic heterocycle" which may fuse the above "heteroaryl" includes 5- to 7-membered aromatic cycle which may contains one or more oxygen atom, sulfur atom and/or nitrogen atom in the ring, or such an aromatic ring as fused with one or more other aromatic rings.

The above "heteroaryl" may be fused 4- to 7-membered cycloalkane or 4- to 7-membered non-aromatic heterocycle. Examples of cycloalkane include cyclobutane, cyclopentane, cyclohexane, and cycloheptane. Examples of non-aromatic heterocycle include pyrrolidine, piperazine, oxorane, 1,3-dioxorane, 1,4-dioxane, thiorane, or the like. The above "cycloalkane" and "non-aromatic heterocycle" may be fused with other aromatic carbocycle such as benzene or aromatic heterocycle such as thiophene or furan. Examples of heteroaryl fused with 4- to 7-membered cycloalkane or 4- to 7-membered non-aromatic heterocycle are illustrated below.

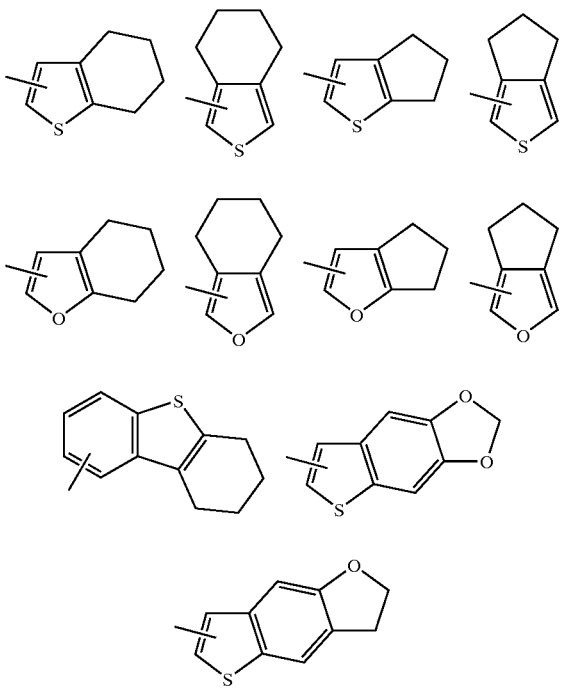

Examples of the substituent on "optionally substituted heteroaryl" include a group of the formula: -$Z^1$-$Z^2$ wherein $Z^1$ is a bond, —O—, —S—, —NH—, —NH—C(=O)—, —NH—C(=O)—O—, —NH—$SO_2$—, —C(=O)—, —O—C(=O)—, —C(=O)—O—, —$SO_2$—, —$CH_2$—

O—, —CH₂—NH—C(=O)—, —CH₂—NH—C(=O)—O—, —CH₂—NH—SO₂—, or —CH₂—C(=O)—, and $Z^2$ is alkyl, haloalkyl, alkenyl, alkynyl, or optionally substituted amino; carboxy; halogen (F, Cl, Br, I); hydroxyalkyl; hydroxy; nitro; cyano; mercapto; thioformyl; thioacetyl; thiocarboxy; dithiocarboxy; thiocarbamoyl; sulfino; sulfo; sulfamoyl; sulfoamino and the like. A group of the formula: $-Z^1-Z^2$ wherein $Z^1$ is a bond, —O—, —S—, —NH—, —NH—C(=O)—, —NH—C(=O)—O—, —NH—SO₂—, —C(=O)—, —O—C(=O)—, —C(=O)—O—, —SO₂—, —CH₂—O—, —CH₂—NH—C(=O)—, —CH₂NH—C(=O)—O—, —CH₂—NH—SO₂—, or —CH₂—C(=O)—, and $Z^2$ is alkyl or optionally substituted amino; carboxy; halogen; hydroxy; and nitro are preferred. Further, A group of the formula: $-Z^1-Z^2$ wherein $Z^1$ is a bond, —O—, —NH—C(=O)—, or —C(=O)—, and $Z^2$ is alkyl or optionally substituted amino; halogen; and hydroxy are preferred. One to three of the above substituents may be at any suitable position on the above heteroaryl.

"Alkyl" includes a straight or branched C1 to C8 alkyl group or a C3 to C8 cycloalkyl group. Examples are methyl, ethyl, n-propyl, isopropyl, n-butyl, isobutyl, tert-butyl, n-pentyl, isopentyl, n-hexyl, n-heptyl, n-octyl, cyclopropyl, cyclobutyl, cyclopentyl, cyclohexyl, cycloheptyl and the like. A straight or branched C1 to C3 alkyl group is preferred.

"Haloalkyl" includes the above alkyl substituted with one to three halogen(s). A straight or branched C1 to C3 haloalkyl is preferred. Trifluoromethyl, 2,2,2-trifluoroethyl and the like are exemplified.

"Alkenyl" includes the above alkyl having one to three double bond(s). A straight or branched C2 to C3 alkenyl is preferred. Vinyl, allyl, 1-propenyl, isopropenyl and the like are exemplified.

"Alkynyl" includes the above alkyl having one to three triple bond(s). A straight C2 to C3 alkynyl is preferred. Ethynyl and the like are preferred.

Examples of the substituent of "optionally substituted amino" include alkyl, alkyloxy, alkylsulfonyl, hydroxy, and the like. It may be mono- or di-substituted with these substituents.

"Hydroxy alkyl" includes the above alkyl substituted with one to three hydroxy. A straight or branched C1 to C3 hydroxyalkyl is preferred. Hydroxymethyl, 2-hydroxyethyl, 1-hydroxyethyl and the like are exemplified.

"Halogen" includes fluoro, chloro, bromo, and iodo.

A compound of the present invention has the following [2.2.1] and [3.1.1] bicyclic skeleton.

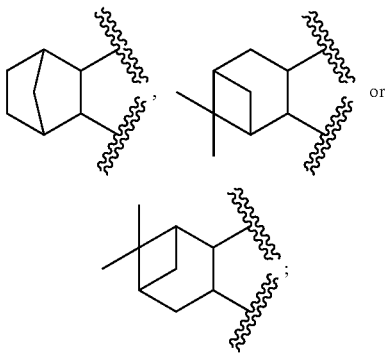

A compound of the present invention can be any of the following stereo isomers of [2.2.1] and [3.1.1] bicyclic skeleton.

In a case of

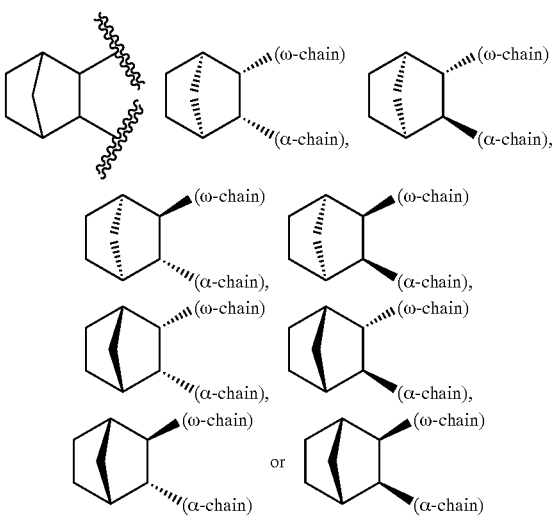

In a case of

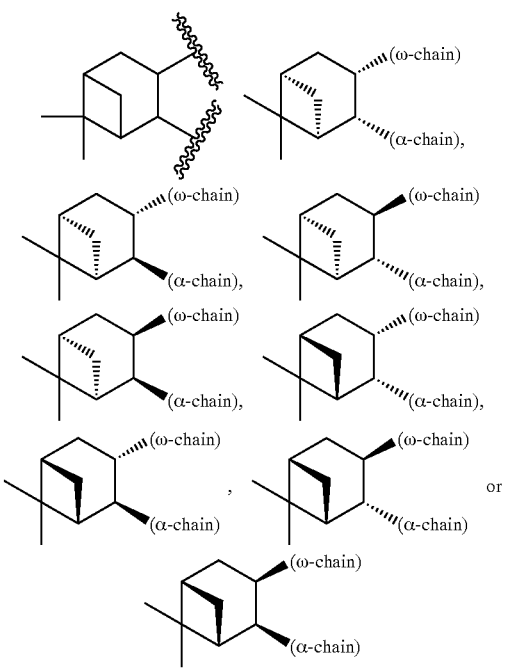

In a case of

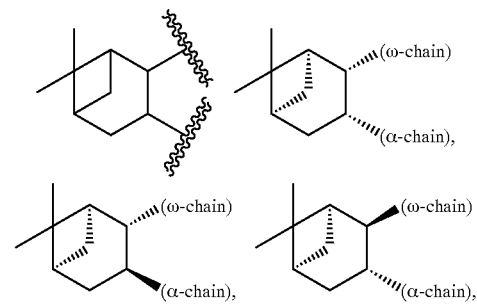

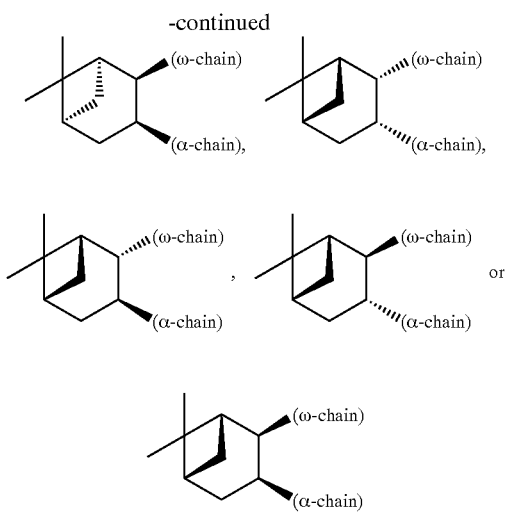

In these stereo isomers, preferable is a compound having the skeleton of the formula:

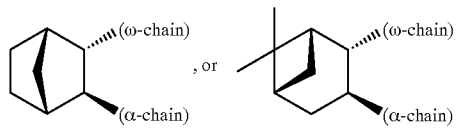

The present invention includes all stereo isomers of them and the optional mixtures thereof. Namely, the bond binding to the bicyclic ring is in R configuration or S configuration, and all of the stereo isomers (diastereomer, epimer, enantiomer and the like), racemates, and optional mixture thereof are included in the present invention.

Moreover, the α chain of the compound of the present invention can be in Z configuration or E configuration, thus a compound having any of the configurations and the mixture thereof are included in the present invention.

Further, as the α chain ($R^3$) of the compound of the present invention, $-CH_2-CH_2-CH_2-CH_2-CH=CH-COOR^4$, $-CH_2-CH_2-CH_2-CH_2-X^1-CH_2-COOR^4$, $-CH_2-CH=CH-CH_2-X^1-CH_2-COOR^4$ and $-CH_2-CH_2-CH_2-CH_2-COOR^4$ ($R^4$ is hydrogen or alkyl; $X^1$ is $-O-$ or $-S-$) are exemplified. Especially, $-CH_2-CH_2-CH_2-CH_2-CH=CH-COOR^4$, $-CH_2-CH_2-CH_2-CH_2-X^1-CH_2-COOR^4$, $-CH_2-CH=CH-CH_2-X^1-CH_2-COOR^4$ and $-CH_2-CH_2-CH_2-CH_2-COOR^4$ ($R^4$ is hydrogen; $X^1$ is $-O-$ or $-S-$) are preferred. Further, $-CH_2-CH_2-CH_2-CH_2-CH=CH-COOR^4$ and $-CH_2-CH_2-CH_2-X^1-CH_2-COOR^4$ ($R^4$ is hydrogen; $X^1$ is $-O-$ or $-S-$) are preferred.

This invention includes not only a compound represented by the formula (I), but also a prodrug, a pharmaceutically acceptable salt or a solvate thereof.

A prodrug of a compound of the formula (I) is a derivative of the compound of the present invention having a group which can be decomposed chemically or metabolically, and such prodrug is converted to a pharmaceutically active compound of the present invention by means of solvolysis or by placing the compound in vivo under a physiological condition. Method for the selection and process of an appropriate prodrug derivative are described in the literature such as Design of Prodrugs, Elsevier, Amsterdam 1985.

When the compound of the formula (I) has a carboxyl group, an ester derivative prepared by reacting a basal acid compound with a suitable alcohol or an amide derivative prepared by reacting a basal acid compound with a suitable amine is exemplified as a prodrug. A particularly preferred ester derivative as an prodrug is an optionally substituted alkyl ester derivative (e.g., methyl ester, ethyl ester, n-propyl ester, isopropyl ester, n-butyl ester, isobutyl ester, tert-butyl ester, morpholinoethyl ester), an arylalkyl ester derivative (e.g., benzyl ester, phenethyl ester, benzhydryl ester), or the like. A particularly preferred amide derivative as a prodrug is alkyl amide derivative (e.g., N-methyl amide, N-ethyl amide, N-(n-propyl)amide, N-isopropyl amide, N-(n-butyl) amide, N-isobutyl amide, N-(tert-butyl)amide), aryl alkyl amide (e.g., N-benzyl amide, N-phenethyl amide, benzhydryl amide), or the like.

When the compound of the formula (I) has a hydroxy group, an acyloxy derivative prepared by reacting with a suitable acyl halide or a suitable acid anhydride is exemplified as a prodrug. A particularly preferred acyloxy derivative as a prodrug is a derivative substituted with optionally substituted alkylcarbonyloxy (e.g., $-OCOC_2H_5$, $-OCO$ (tert-Bu), $-OCOC_{15}H_{31}$, $-OCOCH_2CH_2COONa$, $-OCOCH(NH_2)CH_3$, $-OCOCH_2N(CH_3)_2-$), optionally substituted arylcarbonyloxy (e.g., $-OCO(m-COONa-Ph)$ or the like.

When the compound of the formula (I) has an amino group, an amide derivative prepared by reacting with a suitable acid halide or a suitable acid anhydride is exemplified as a prodrug. A particularly preferred amide derivative as a prodrug is a derivative substituted with optionally substituted alkylcarbonyl (e.g., $-NHCO(CH_2)_{20}CH_3$, $-NHCOCH(NH_2)CH_3$) or the like.

Examples of a salt of the compound of the formula (I) or its prodrug include alkali metal salts such as lithium salts, sodium salts or potassium salts, alkaline-earth metal salts such as calcium salts, salts with organic bases such as tromethamine, trimethylamine, triethylamine, 2-aminobutane, tert-butylamine, diisopropylethylamine, n-butylmethylamine, cyclohexylamine, dicyclohexylamine, N-isopropylcyclohexylamine, furfurylamine, benzylamine, methylbenzylamine, dibenzylamine, N,N-dimethylbenzylamine, 2-chlorobenzylamine, 4-methoxybenzylamine, 1-naphthylene methylamine, diphenylbenzylamine, triphenylamine, 1-naphthylamine, 1-aminoanthorathene, 2-aminoanthorathene, dehydroabiethylamine, N-methylmorpholine, pyridine), basic amino acid salts such as arginine salts or lysine salts.

A solvate means a solvate with an organic solvent, a hydrate and the like of the compound of the formula (I), its prodrug or its pharmaceutically acceptable salt, for example, monohydrate, dihydrate or the like.

"A pharmaceutical composition having an antagonistic activity against $PGD_2$ receptor" means a pharmaceutical composition comprising at least one compound of the formula (I) having an antagonistic activity against a $PGD_2$ receptor. In addition to a compound of the formula (I), the other active agents (e.g. antiinflammatory agents, antiallergy agents and the like) and pharmaceutically acceptable admixtures (e.g., binding agent, filler and the like) may be included.

A $PGD_2$ antagonist is useful in the improvement of conditions due to excessive production of $PGD_2$, particularly as a composition for treating diseases in which mast cell dysfunction is involved, for example, systemic mastocytosis and disorder of systemic mast cell activation as well as for nasal blockage, allergic conjunctivitis, allergic rhinitis, airway contraction, asthma, urticaria, ischemic reperfusion injury, inflammation, and atopic dermatitis.

This invention includes a method for treating a condition due to excessive production of $PGD_2$ such as nasal blockage, allergic conjunctivitis, allergic rhinitis, and the like, which comprises administrating a compound represented by the formula (I). In addition, this invention includes use of the compound represented by the formula (I) for the preparation of a pharmaceutical composition for treating a condition due to excessive production of $PGD_2$ such as nasal blockage, allergic conjunctivitis or allergic rhinitis.

BEST MODE FOR CARRYING OUT THE INVENTION

The compound represented by the formula (I) can be prepared in accordance with the following method.

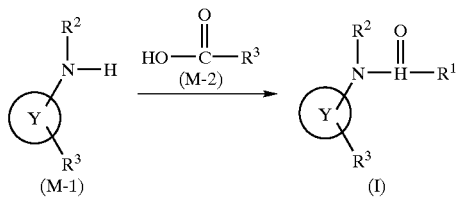

wherein

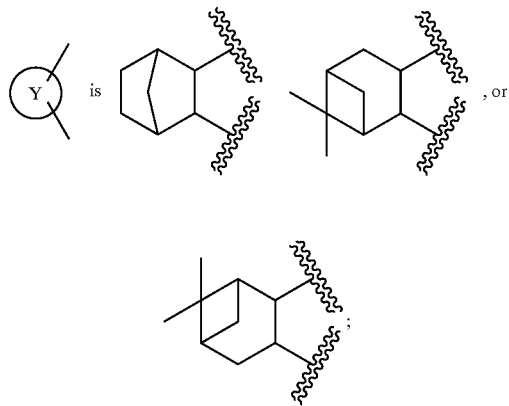

$R^1$ is optionally substituted heteroaryl;
$R^2$ is hydrogen or alkyl;
$R^3$ is —$CH_2$—$CH_2$—$CH_2$—$CH_2$—CH=CH—$COOR^4$,
    —$CH_2$—$CH_2$—$CH_2$—$CH_2$—$X^1$—$CH_2$—$COOR^4$,
    —$CH_2$—CH=CH—$CH_2$—$X^1$—$CH_2$—$COOR^4$ or
    —$CH_2$—$CH_2$—$CH_2$—$CH_2$—$COOR^4$;
$R^4$ is hydrogen or alkyl; and
$X^1$ is —O— or —S—.

As shown in the above process, the compound of the formula (I) can be prepared by reacting a carboxylic acid of the formula (M-2) or its reactive derivative with an amino compound of the formula (M-1).

The reactive derivatives of carboxylic acid of the formula (M-2) mean the corresponding acid halides (e.g., chloride, bromide, iodide), anhydrides (e.g., mixed anhydride with formic acid or acetic acid), active esters (e.g., N-hydroxysuccinimide ester), and the like, and include acylating agents used for the usual acylation of amino group.

For example, an acid halide is obtained by reacting the compound (M-2) with a thionyl halide (e.g., thionyl chloride), phosphorous halide (e.g., phosphorous trichloride, phosphorous pentachloride), oxalyl halide (e.g., oxalyl chloride), and the like, in accordance with known methods as described in the literatures.

The reaction can be conducted under a condition generally used for the acylation of amino group. For example, in the case of condensation with the acid halide, the reaction is carried out in a solvent such as an ether solvent (e.g., diethyl ether, tetrahydrofuran, dioxane), benzene solvent (e.g., benzene, toluene, xylene), halogenated hydrocarbon solvent (e.g., dichloromethane, dichloroethane, chloroform) as well as ethyl acetate, dimethylformamide, dimethyl sulfoxide, acetonitrile, or the like, if necessary, in the presence of a base (e.g., organic base such as triethylamine, pyridine, N,N-dimethylaminopyridine, N-methylmorpholine; inorganic base such as sodium hydroxide, potassium hydroxide, potassium carbonate, or the like) under cooling, at room temperature, or under heating, preferably at a temperature ranging from −20° C. to ice-cooling temperature, or from room temperature to a refluxing temperature of the reaction system, during several min to several hr, preferably for 0.5 hr to 24 hr, more preferably for 1 hr to 12 hr.

When $R^4$ is alkyl, a free form may be used without converting the carboxy group (M-2) into the reactive derivatives and the reaction may be conducted in the presence of a condensing agent (e.g., dicyclohexylcarbodiimide (DCC), 1-ethyl-3-(3-methylaminopropyl)carbodiimide, N,N'-carbonyldiimidazole, or the like) usually used in the condensation reaction of amine and carboxylic acid.

When the substituent of "optionally substituted aryl" or "optionally substituted heteroaryl" of the compound of the formula (M-2) is substituted with a hydroxy group, an amino group or the like, such a compound can be used after protection by acetyl group or the like in accordance with the well known method.

In the reaction of the other reactive derivatives or free acid (M-2) with the amine (M-1), the reaction conditions are determined according to the property of each reactive derivative or free acid, in accordance with a known method. The reaction product can be purified in accordance with a conventional purification, such as the extraction with a solvent, chromatography, recrystallization, and the like.

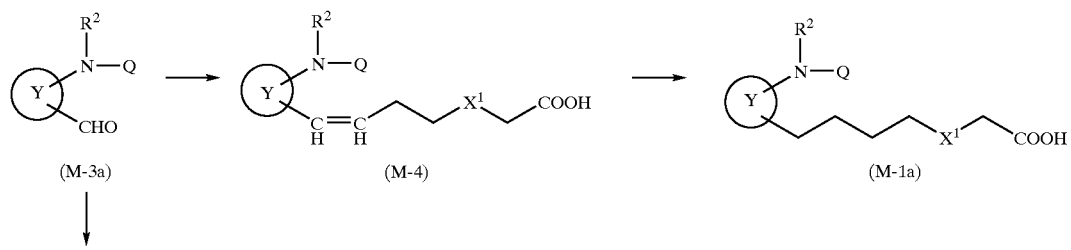

-continued

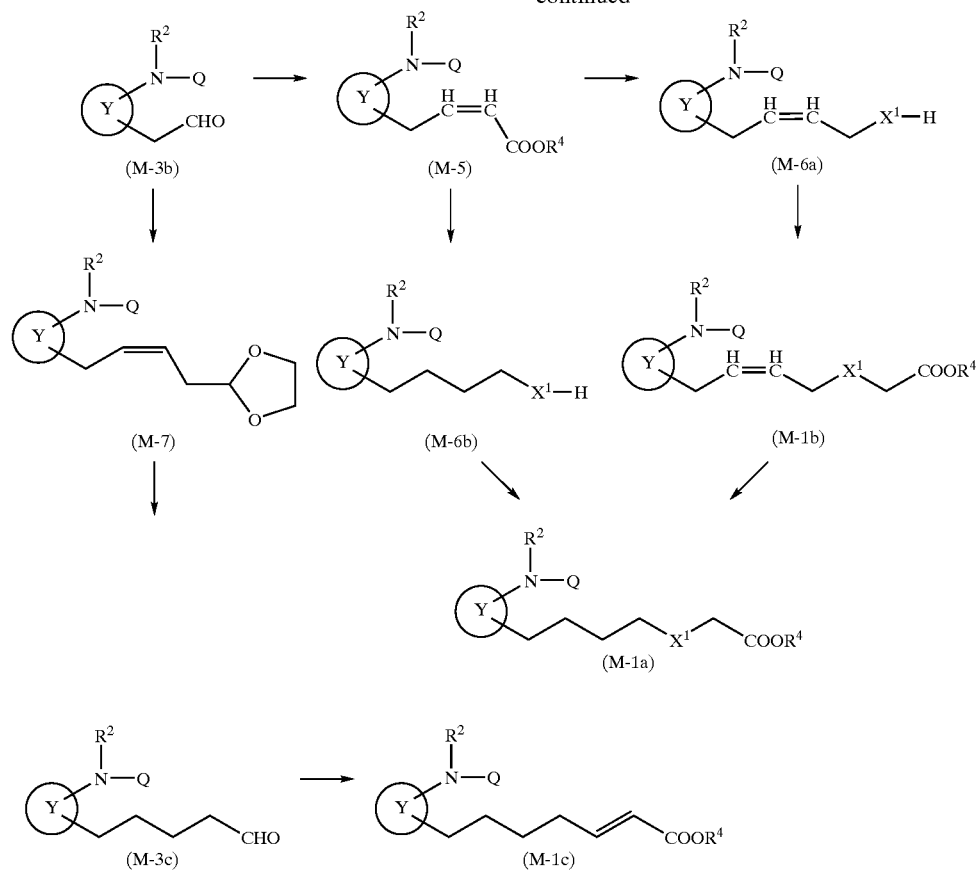

wherein Q is a protective group of an amino group; $R^2$, $X^1$ and $R^4$ are as defined above.

The compounds represented by formula (M-1) can be prepared from the aldehyde derivative (Q is a protecting group such as benzyloxycarbonyl, t-butoxycarbonyl and the like) represented by a general formula (M-3a) or (M-3b) by one or more reaction(s) of a ylide compound under a Wittig reaction condition (Org. Reaction, 1965, 14, 270) in combination with other reactions.

For example, the aldehyde (M-3a) is reacted with phosphonium salt derived from 6-bromo-3-oxahexanoic acid described in WO97/40104 under a well known Wittig reaction condition to give a compound (M-4). The compound (M-4) is hydrogenated in the presence of palladium, platinum and the like to give a starting material (M-1a, $X^1$=O), wherein $R^3$ is —$CH_2CH_2CH_2CH_2OCH_2COOR^4$. Furthermore, after Wittig reaction using methoxymethyltriphenyl-phosphonium salt, followed by a hydrolysis with hydrochloric acid, formic acid, acetic acid and the like can furnish an aldehyde (M-3b). Under Wittig reaction condition using a stable ylide such as methyl (triphenylphophoranidene)acetate and the like or Honer-Emmons reaction condition using methyl dimethylphosphonoacetate, the above aldehyde can be converted into α,β-unsaturated carboxylic acid derivative represented by the formula (M-5). An alcohol derivative (M-6a, $X^1$=O) which is obtained by reduction of compound (M-5) is reacted with halogenated acetic acid or its ester derivative in accordance with well known methods to give a starting compound (M-1b, $X^1$=O) wherein $R^3$ is —$CH_2CH$=$CHCH_2OCH_2COOR^4$. Further, after an alcohol derivative (M-6a, $X^1$=O) is converted into a thiol derivative ($X^1$=S) in accordance with well known methods, the obtained compound is reacted with halogenated acetic acid derivative as shown the above to give a starting compound (M-1b, $X^1$=S) wherein $R^3$ is —$CH_2CH$=$CHCH_2SCH_2COOR^4$. Also, after an alcohol derivative (M-6a, $X^1$=O) is converted into a halogenated derivative in accordance with well known methods, the obtained compound is reacted with a glycolic acid or a thioglycollic acid in the presence of a base to give the above compound (M-1b, $X^1$=S). The double bonds in the $R^3$ can be reduced by hydrogenation in the presence of catalyst such as palladium, platinum, and the like at the suitable stage to give a corresponding saturated derivative (M-1a, $X^1$=O or S) at ease.

The aldehyde (M-3b) is converted into a compound represented by the formula (M-7) by Wittig reaction using 2-(1,3-dioxolane-2-yl)ethyltriphenylphosphonium salt. A hydrogenation of the compound (M-7) and an acidic hydrolysis of acetal are carried out to give the aldehyde (M-3c) as shown in the above. Under Wittig reaction condition using a stable ylide such as methyl (triphenylphophoranidene)acetate and the like or Honer-Emmons reaction condition using methyl dimethylphosphonoacetate, the above aldehyde (M-3c) can be converted into a starting compound (M-1c) wherein $R^3$ corresponds to —$CH_2CH_2CH_2CH_2CH$=$CHCOOR^4$.

Amidation with a starting carboxylic acid (M-2) can be accomplished after a deprotection of an amino protecting group Q in a way of conversion to α-chain, if necessary.

In case of the introduction of a substituent(s) into the "optionally substituted aryl" or "optionally substituted heteroaryl", the change of the functional group can be performed before or after reacting a carboxylic acid or its reactive derivative thereof (M-2) with the amine (M-1). For example, the compound having an aromatic heterocycle substituted with a nitro group can be prepared through the nitration of the compound with a nitrating acid. Moreover, the compound having an aromatic heterocycle substituted with an amino group can be prepared through the reduction of the above-obtained compound with tin in the presence of hydrochloride. Moreover, the compound having an aromatic heterocycle substituted with a hydroxy group can be prepared through the diazonization of the above-obtained compound and the hydrolysis with alkali. On the other hand, the compound having an aromatic heterocycle substituted with an alkoxy group can be prepared through the reaction of the diazonium derivative with alcohol. The compound having an aromatic heterocycle substituted with halogen can be prepared through Sandmeyer reaction, the reaction of the diazonium derivative with a copper salt (e.g., $CuCl_2$, $CuBr_2$). The compound having an aromatic heterocycle substituted with halogen can be also prepared through the direct reaction of the compound having an aromatic heterocycle with chlorine and the like. Using the above-mentioned methods appropriately, halogen can be introduced into a desired position(s). The group of alkyl, alkenyl or acyl group can be directly introduced into an aromatic heterocycle through Friedel Crafts reaction with alkylating agent, an alkenylating agent, or an acylating agent, respectively, in the presence of anhydrous aluminum chloride and the like.

When using the compound (I) of the present invention in treatment, it can be formulated into ordinary formulations for oral and parenteral administration. A pharmaceutical composition containing the compound (I) of the present invention can be in the form for oral and parenteral administration. Specifically, it can be formulated into formulations for oral administration such as tablets, capsules, granules, powders, syrup, and the like; or those for parenteral administration such as injectable solution or suspension for intravenous, intramuscular, or subcutaneous injection, inhalant, eye drops, nasal drops, suppositories, or percutaneous formulations such as ointment.

In preparing the formulations, carriers, excipients, solvents, and bases known to one having ordinary skill in the art may be used. In case of tablets, they are prepared by compressing or formulating an active ingredient together with auxiliary components. Examples of usable auxiliary components include pharmaceutically acceptable excipients such as binders (e.g., cornstarch), fillers (e.g., lactose, microcrystalline cellulose), disintegrants (e.g., starch sodium glycolate) or lubricants (e.g., magnesium stearate). Tablets may be coated appropriately. In case of liquid formulations such as syrups, solutions, or suspensions, they may contain suspending agents (e.g., methyl cellulose), emulsifiers (e.g., lecithin), preservatives, and the like. In case of injectable formulations, it may be in the form of solution, suspension, or oily or aqueous emulsion, which may contain suspension-stabilizing agents or dispersing agent, and the like. In case of an inhalant, it is formulated into a liquid formulation applicable to an inhaler. In case of eye drops, it is formulated into a solution or a suspension.

Especially, in case of a nasal drug for treating nasal blockage, it can be used as a solution or suspension prepared by a conventional formulating method, or administered as a powder formulated using a powdering agent (e.g., hydroxypropyl cellulose, carbopole) into the nasal cavity. Alternatively, it can be used as an aerosol filled into a special container together with a solvent of low boiling point.

In a case using as an eyewash drug for treating allergic conjunctivitis, it can be used as a solution or suspension of the compound or can be used by solving or suspending the compound before use. A stabilizing agent, solubilizing agent, suspending agent, emulsifier, buffer, preservatives and the like can be included. In a case using as an eyewash drug, aseptic treatment is preferable.

Although an appropriate dosage of the compound (I) varies depending on the administration route, age, body weight, sex, or conditions of the patient, and the kind of drug(s) used together, if any, and should be determined by the physician in the end, in the case of oral administration, the daily dosage can generally be between 0.01–100 mg, preferably 0.01–10 mg, more preferably 0.01–1 mg, per kg body weight. In case of parenteral administration, the daily dosage can generally be between 0.001–100 mg, preferably 0.001–1 mg, more preferably 0.001–0.1 mg, per kg body weight. The daily dosage can be administered in 1–4 divisions.

EXAMPLE

The following examples are provided to further illustrate the present invention and are not to be construed as limiting the scope.

Example 1

Preparation of (Ic-4)

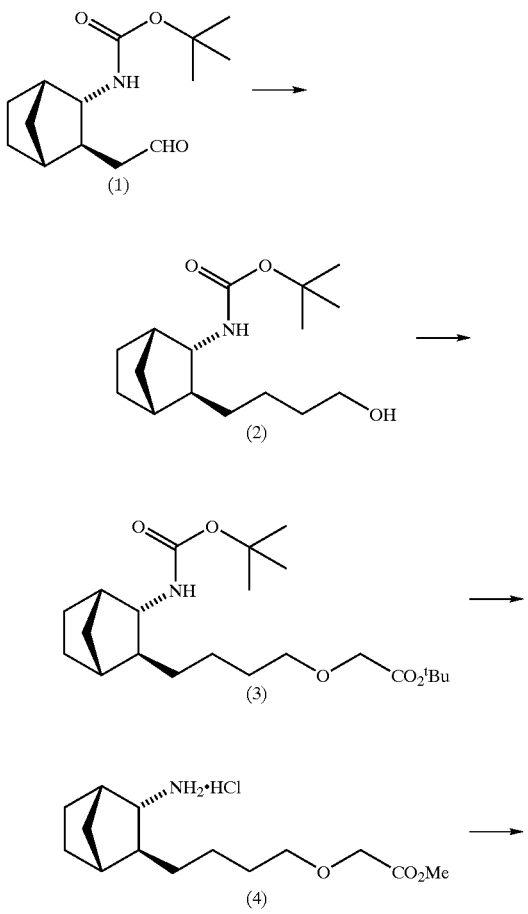

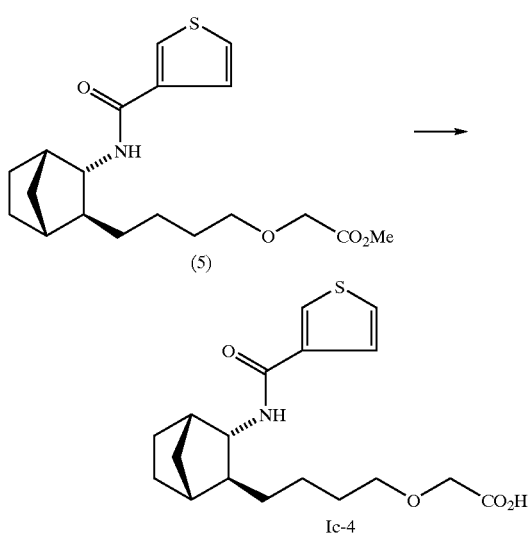

Process 1

To a solution of compound (1) (10.11 g, 39.9 mmol) in toluene (100 ml) was added triphenylphosphoranylidene acetic acid methyl ester (14.68 g, 43.9 mmol) and the resulting mixture was stirred for 17 h at room temperature. Hexane (100 ml) was added to the mixture and the insoluble residue was filtered off. The filtration was concentrated to give 16.56 g of residue. 16.12 g of the residue was dissolved in THF(160 ml), 2N lithium hydroxide aq. (40 ml) was added to the solution and the resulting mixture was stirred for 5 h at 60° C. After THF was concentrated in vacuo, the residue was diluted with water (100 ml). The water layer was washed with toluene twice and acidified with hydrochloric acid (pH=1) and extracted with ethyl acetate. The organic layer was washed with water and brine, dried, and concentrated. To a solution of the residue in methanol was added 10% palladium-carbon (360 mg) and the resulting mixture was stirred for 3 h under hydrogen atmosphere. The reaction mixture was filtered and concentrated and the residues was dissolved in THF (120 ml). To the mixture were added triethylamine (6.2 ml, 44.5 mmol) and ethyl chloroformate (4.3 ml, 44.5 mmol ) at ice-cooling, and the resulting mixture was stirred for 30 min at ice-cooling. The insoluble salt was filtered off and sodium borohydride (3.06 g, 80.9 mmol) was added to the filtration. To the mixture was added methanol (40 ml) dropwise over 30 min and the mixture was stirred for 30 min. The reaction mixture was diluted with water and extracted with ethyl acetate. The organic layer was washed with water and brine respectively and dried. The residue was crystallized from hexane-ethyl acetate (90:10) to give compound (2) (8.77 g; yield 80%). mp. 90–92° C.

Process 2

To a solution of the compound (2) (1.68 g, 5.94 mmol) in toluene (17 ml) were added t-butyl bromoacetate (1.32 ml, 68.91 mmol), sodium hydrogensulfate (201 mg, 0.6 mmol) and 50% sodium hydroxide aq. (1.7 ml) and the resulting mixture was vigorously stirred for 22 h at room temperature. Toluene layer was separated, washed with water and brine respectively, dried, concentrated, and chromatographed on silica gel (hexane-ethyl acetate=7:1) to give compound (3) (1.60 g; yield 68%).

Process 3

To a solution of the compound (3) (10.42 g, 26.2 mmol) in methanol (50 ml) was added 4N dioxane solution of hydrogen chloride (65.5 ml, 262 mmol) and the resulting mixture was stirred for 5 h at room temperature. The reaction mixture was concentrated in vacuo to give crystalline residue. The residue was washed with hexane-ether to give compound (4) (6.88 g; yield 90%).

Process 4

To a solution of compound (4) (642 mg, 2.20 mmol) in THF (8 ml) were added thiophene-3-carboxylic acid (256 mg, 2.00 mmol), 1-hydroxybenzotriazole (27 mg, 0.20 mmol) and triethylamine (0.34 ml, 2.40 mmol) at ice-cooling. Further, 3-ethyl-3-(3-dimethylaminopropyl) carbodiimide (370 mg, 2.40 mmol) was added to the mixture at ice-cooling. The reaction mixture was stirred for 16 h at room temperature and diluted with ethyl acetate. The resulting mixture was washed with dilute hydrochloric acid and sodium hydrogencarbonate respectively, dried, concentrated, and chromatographed on silica gel (toluene-hexane=3:1) to give compound (5) (627 mg; yield 86%). m.p. 68–70° C.

Process 5

To a solution of compound (5) (620 mg, 1.70 mmol) in methanol (2 ml)-THF (1 ml) was added 4N sodium hydroxide aq.(1.0 ml, 4.0 mmol) and the resulting mixture was stirred for 16 h at room temperature. The reaction mixture was acidified with 2N hydrochloric acid. and extracted with ethyl acetate. The organic layer was washed with water and brine respectively, dried and concentrated. The residue was crystallized from methanol-water (5:7) to give compound (Ic-4) (461 mg; yield 77%). m.p. 104–105° C.

Example 2

Preparation of Compound (Ie-34)

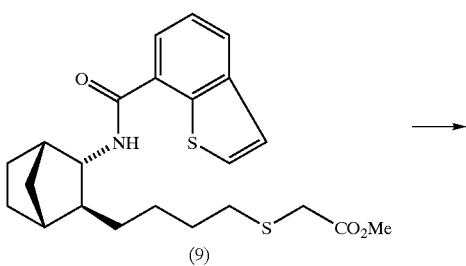

(9)

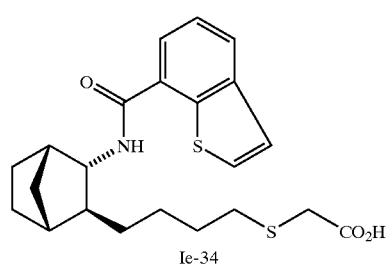

Ie-34

Process 1

To a solution of compound (2) (2.28 g, 8.05 mmol) in dichloromethane (20 ml) were added triphenylphosphine (2.32 g, 8.85 mmol) and N-bromosuccinimide (1.58 g, 8.85 mmol) at ice-cooling and the resulting mixture was stirred for 1 h at the same temperature. The reaction mixture was diluted with toluene, washed with water and brine respectively, dried, concentrated, and chromatographed on silica gel (hexane-ethyl acetate=9:1) to give compound (6) (2.70 g; yield 97%).

Process 2

To a solution of sodium methoxide (842 mg, 15.6 mmol) in methanol (20 ml) was added methyl thioglycolate (1.40 ml, 15.6 mmol) and the resulting mixture was stirred for 15 min at room temperature. To the mixture was added a THF (20 ml) solution of compound (6) (2.70 g, 7.80 mmol) and the resulting mixture was stirred for 15 h. The reaction was diluted with ethyl acetate, washed with water and brine respectively, dried, concentrated, and chromatographed on silica gel (hexane-ethyl acetate=78:22) to give compound (7) (2.84 g; yield 98%).

Process 3

4N Ethyl acetate solution of hydrogen chloride (15 ml) was added to compound (7) (2.84 g, 7.64 mmol) and the resulting mixture was stirred for 2 h at room temperature. The reaction mixture was concentrated in vacuo to give the residue. The residue was crystallized from hexane-ether to give compound (8) (2.16 g; yield 92%).

Process 4

To a solution of compound (8) (246 mg, 0.80 mmol) in THF (6 ml) were added benzothiophene-7-carboxylic acid (150 mg, 0.80 mmol), 1-hydroxybenzotriazole (11 mg, 0.08 mmol), triethylamine (0.12 ml, 0.96 mmol) at ice-cooling. Further, 1-ethyl-3-(3-dimethylaminopropyl)carbodiimide (149 mg, 0.96 mmol) was added to the mixture at ice-cooling. The reaction mixture was stirred for 16 h at room temperature and diluted with ethyl acetate. The resulting mixture was washed with dilute hydrochloric acid and sodium hydrogencarbonate aq. respectively, dried, concentrated, and chromatographed on silica gel (hexane-ethyl acetate=3:1) to give compound (9) (324 mg; yield 94%).

Process 5

To a solution of compound (9) (315 mg, 0.73 mmol) in THF (3.6 ml)-methanol (7.3 ml) was added 1N sodium hydroxide aq.(1.82 ml, 1.82 mmol) and the resulting mixture was stirred for 48 h at room temperature. The reaction mixture was acidified with 2N hydrochloric acid and extracted with ethyl acetate. The organic layer was washed with water and brine respectively to give compound (Ie-34) (301 mg; yield 99%).

Example 3

Preparation of Compound (IIb-28)

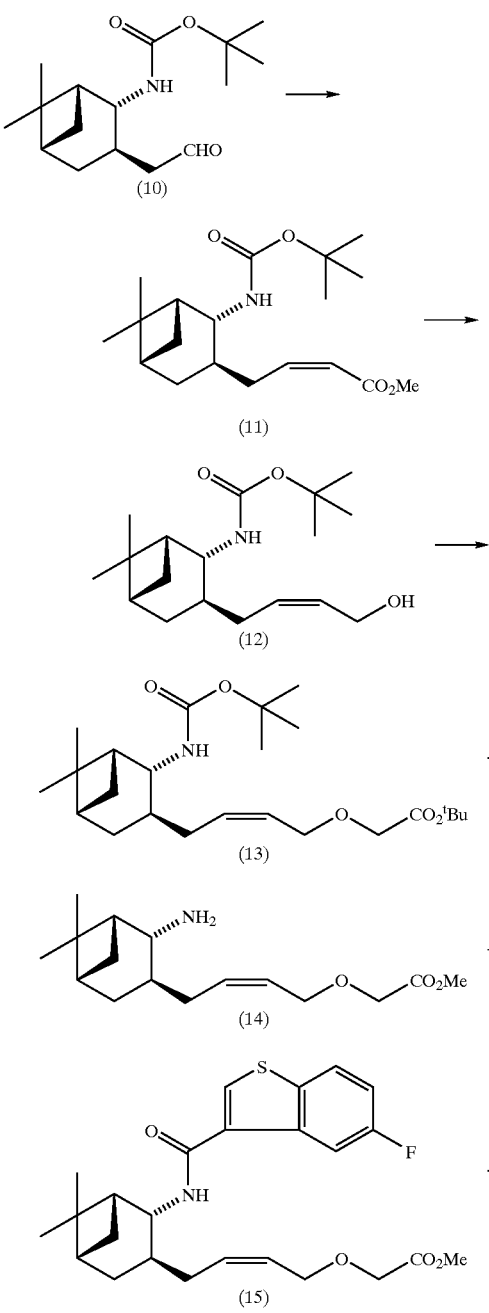

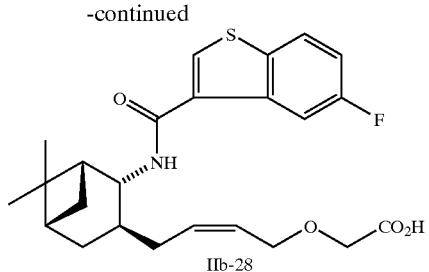

IIb-28

Process 1

A solution of methyl bis(2,2,2-trifluoroethyl) phosphonoacetate (3.0 ml, 14.3 mmol) and 18-crown-6 (5.64 g, 21.3 mmol) in THF (100 ml) was cooled at −55° C. and bis(trimethylsilyl)amide potassium (0.5M toluene solution, 28.5 ml, 14.3 mmol) was added dropwise to the mixture. The resulting mixture was stirred for 15 min. To the mixture was added a solution of compound (10) (2.0 g, 7.11 mmol) in THF (20 ml) was added dropwise over 15 min and the mixture was stirred for 1 h at the same temperature. The reaction mixture was allowed to warm to 0° C., diluted with water, and extracted with ethyl acetate. The organic layer was washed with water and brine respectively, dried, concentrated, and chromatographed on silica gel (hexane-ethyl acetate=4:1) to give compound (11) (2.16 g; yield 90%).

Process 2

A solution of compound (11) (1.37 g, 4.05 mmol) in dichloromethane (10 ml)-hexane (10 ml) was cooled to −60° C. and diisopropylaluminum hydride (0.95M hexane solution, 10.7 ml, 10.2 mmol) was added dropwise to the solution. The mixture was stirred for 30 min at the same temperature and methanol (0.6 ml) was added. The resulting mixture was allowed to warm to room temperature and 2N hydrochloric acid was added. The mixture was extracted with ethyl acetate and the organic layer was washed with sodium hydrogencarbonate aq. and brine respectively, dried, concentrated, and chromatographed on silica gel (hexane-ethyl acetate=2:1) to give compound (12) (1.14 g; yield 91%). m.p. 67–69° C.

Process 3

To a solution of compound (12) (1.03 g, 3.31 mmol) in toluene (10 ml) were added t-butyl bromoacetate (0.70 ml, 4.30 mmol), tetrabutylammonium hydrogensulfate (170 mg, 0.5 mmol), and 50% sodium hydroxide (1.5 ml) and the resulting mixture was vigorously stirred for 18 h at room temperature. The reaction mixture was extracted with toluene, washed with water and brine respectively, dried, concentrated, and chromatographed on silica gel (hexane-ethyl acetate=4:1) to give compound (13) (1.32 g; yield 94%).

Process 4

To a solution of compound (13) (1.3 g, 3.07 mmol) in toluene (3 ml) was added trifluoroacetic acid (3.5 ml, 46 mmol) and the resulting mixture was stirred for 3.5 h at 65° C. The reaction mixture was concentrated in vacuo and methanol (30 ml) and concentrated sulphuric acid (0.33 ml) were added to the mixture. The resulting mixture was stirred for 1 h at reflux. The reaction mixture was concentrated and the residue was dissolved in toluene. To the mixture was added triethylamine (4.3 ml, 30 mmol) and sodium hydrogencarbonate aq. respectively. The toluene layer was separated, washed with water and brine respectively, dried, and concentrated to give compound (14) (697 mg; yield 81%).

Process 5

To a solution of compound (14) (141 mg, 0.50 mmol) in THF (4 ml) were added 5-fluorobenzothiophene-3-carboxylic acid (98 mg, 0.50 mmol) and 1-hydroxybenzotriazole (7 mg, 0.05 mmol) at ice-cooling. Further, 1-ethyl-3-(3-dimethylaminopropyl)carbodiimide (93 mg, 0.6 mmol) was added at the same temperature. The reaction mixture was stirred for 16 h at room temperature, diluted with ethyl acetate, washed with dilute hydrochloric acid and sodium hydrogencarbonate aq. respectively, dried, concentrated, and chromatographed on silica gel (hexane-ethyl acetate=83:17) to give compound (15) (93 mg; yield 40%).

Process 6

To a solution of compound (15) (93 mg, 0.20 mmol) in THF (1 ml)-methanol (2 ml) was added 1N sodium hydroxide aq.(0.5 ml, 0.5 mmol) and the resulting mixture was stirred for 18 h at room temperature. The reaction mixture was acidified with 2N hydrochloric acid and extracted with ethyl acetate. The organic layer was washed with water and brine respectively to give compound (IIb-28) (82 mg; yield 91%).

Example 4

Preparation of Compound (IIa-52)

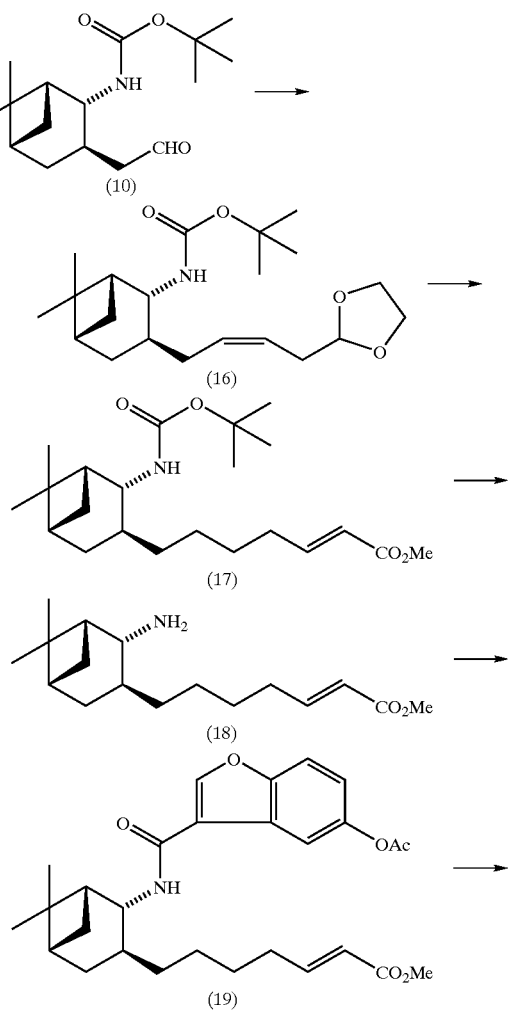

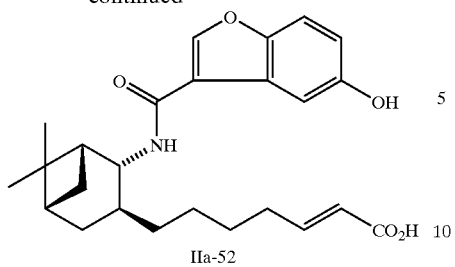
IIa-52

Process 1

A suspension of 2-(1,3-dioxorane-2-yl)ethyltriphenylphosphonium bromide (13.28 g, 30.0 mmol) in THF (60 ml) was cooled to −30° C. and potassium t-butoxide (6.73 g, 60.0 mmol) was added. The mixture was stirred for 1 h at −30° C. to 0° C. and allowed to cool to −25° C. To the mixture was added a solution of compound (10) (5.62 g, 20.0 mmol) in THF (40 ml) dropwise over 15 min. The reaction mixture was allowed to warm to 0° C., stirred for additional 1.5 h, diluted with water. The water layer was extracted with ethyl acetate and the extract is washed with water and brine, dried, concentrated, and chromatographed on silica gel (hexane-ethyl acetate=85:15) to give compound (16) (6.27 g; yield 86%).

Process 2

A solution of compound (16) (4.10 g, 11.2 mmol) in methanol (41 ml) was stirred for 2 h in the presence of 10% palladium-carbon (0.21 g) under hydrogen atmosphere. The reaction mixture was filtered and concentrated to give a residue (4.12 g; yield 100%). To a solution of the crude compound (3.68 g, 10.0 mmol) in acetone-water (4:1, 50 ml) was added pyridinium p-toluenesulfonate (503 mg, 2.0 mmol) and the mixture was heated for 6 h at reflux. The reaction mixture was diluted with water and extracted with ethyl acetate. The organic layer was washed with water and brine, dried, concentrated. A solution of the residue in toluene (35 ml) was added methyl (triphenylphosphoranylidene)acetate (2.93 g, 8.76 mmol) and the resulting mixture was stirred for 18 h at room temperature. The mixture was diluted with ethyl acetate, washed with water and brine, dried, concentrated, and chromatographed on silica gel (hexane-ethyl acetate=85:15) to give compound (17) (2.71 g; yield 71%).

Process 3

To a solution of compound (17) (2.35 g, 6.19 mmol) in dichloromethane (38 ml) was added trifluoroacetic acid (3.82 ml, 49.5 mmol) and the resulting mixture was stirred for 3 h at room temperature. The reaction mixture was concentrated in vacuo and the residue was dissolved in toluene (50 ml) and water (10 ml). The water layer was alkalinized with 2N sodium hydroxide (pH=10). Toluene layer was separated, washed with water and brine, dried, and concentrated to give compound (18) (1.70 g, yield 98%).

Process 4

To a solution of compound (18) (280 mg, 1.0 mmol) in THF (5 ml) were added 5-acetoxybenzofuran-3-carboxylic acid (220 mg, 1.0 mmol), 1-hydroxybenzotriazole (13 mg, 0.1 mmol). Further, 1-ethyl-3-(3-dimethylaminopropyl) carbodiimide (200 mg, 1.3 mmol) was added at ice-cooling. After the reaction mixture was stirred for 16 h at room temperature, the mixture was diluted with toluene, washed with dilute hydrochloric acid and sodium hydrogencarbonate aq. respectively, dried, and concentrated. The residue was chromatographed on silica gel (hexane-ethyl acetate= 3:1) to give compound (19) (422 mg; yield 88%). m.p. 119–120° C.

Process 5

To a solution of compound (19) (422 mg, 0.88 mmol) in THF (5.6 ml) was added 1N lithium hydroxide aq. (3.0 ml, 3.0 mmol) and the resulting mixture was stirred for 20 h at room temperature. The reaction mixture was acidified with 2N hydrochloric acid and extracted with ethyl acetate. The extract was washed with water and brine respectively, dried, and concentrated. The residue was crystallized from hexane-ethyl acetate to give compound (IIa-52) (327 mg; yield 87%). m.p. 159–160° C.

The structure and physical property of the compound prepared in accordance with the above examples are shown below. Each sign such as Ia, Ib, IIe, and IIf used in the following Tables means the partial structure represented below:

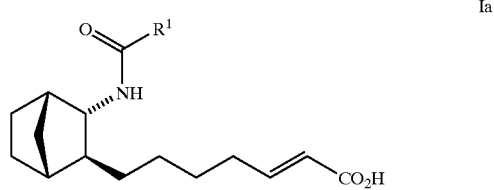
Ia

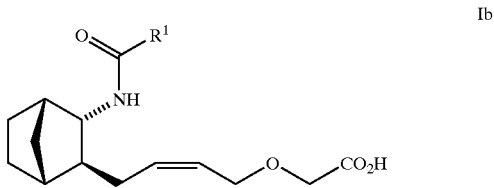
Ib

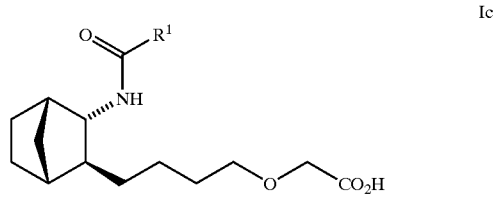
Ic

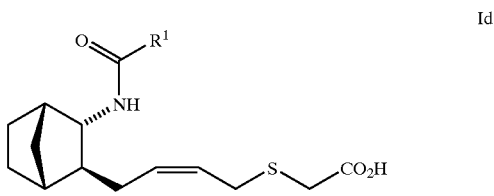
Id

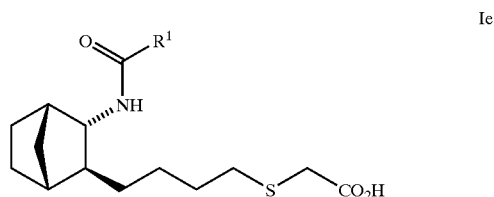
Ie

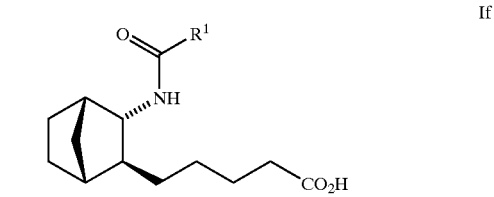
If

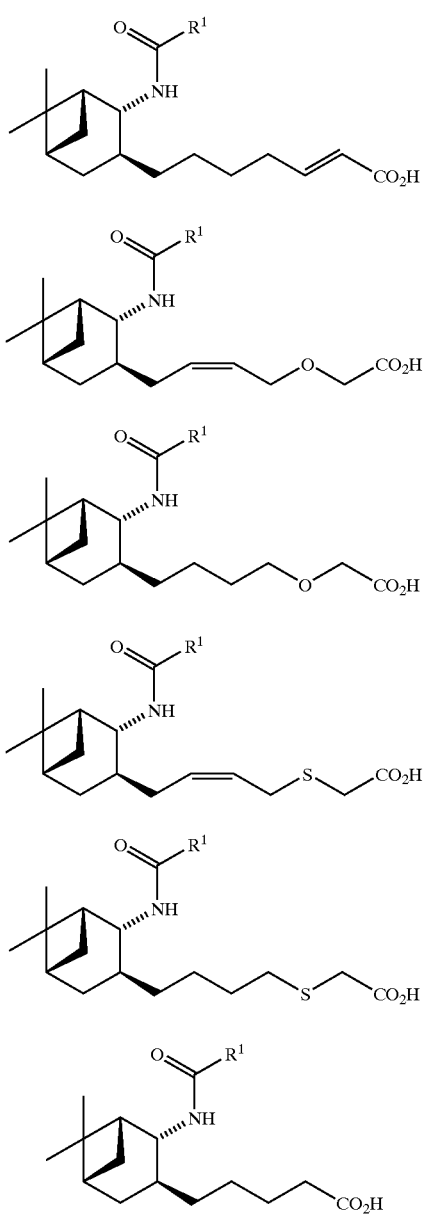

TABLE 1

| R¹ | Ia | Ib | Ic | Id | Ie | If |
|---|---|---|---|---|---|---|
| 2-methylthiophene | Ia-1 | Ib-1 | Ic-1 | Id-1 | Ie-1 | If-1 |
| 2,5-dimethylthiophene | Ia-2 | Ib-2 | Ic-2 | Id-2 | Ie-2 | If-2 |
| 2,3-dimethylthiophene | Ia-3 | Ib-3 | Ic-3 | Id-3 | Ie-3 | If-3 |
| 3-methylthiophene | Ia-4 | Ib-4 | Ic-4 | Id-4 | Ie-4 | If-4 |
| 2,4-dimethylthiophene | Ia-5 | Ia-5 | Ic-5 | Id-5 | Ie-5 | If-5 |
| 2-isopropyl-4-methylthiophene | Ia-6 | Ib-6 | Ic-6 | Id-6 | Ie-6 | If-6 |
| 2,3-dimethylthiophene variant | Ia-7 | Ib-7 | Ic-7 | Id-7 | Ie-7 | If-7 |
| 3,4-dimethylthiophene | Ia-8 | Ib-8 | Ic-8 | Id-8 | Ie-8 | If-8 |
| 2-bromo-4-methylthiophene | Ia-9 | Ib-9 | Ic-9 | Id-9 | Ie-9 | If-9 |
| 2-methoxy-4-methylthiophene | Ia-10 | Ib-10 | Ic-10 | Id-10 | Ie-10 | If-10 |

TABLE 2

Structure: norbornane with -NH-C(=O)-R¹ substituent and R³ substituent

| R¹ | Ia | Ib | Ic | Id | Ie | If |
|---|---|---|---|---|---|---|
| 4-methyl-2-(methylthio)thiophene | Ia-11 | Ib-11 | Ic-11 | Id-11 | Ie-11 | If-11 |
| 2-methylbenzothiophene | Ia-12 | Ib-12 | Ic-12 | Id-12 | Ie-12 | If-12 |
| 2-methyl-7-methylbenzothiophene | Ia-13 | Ib-13 | Ic-13 | Id-13 | Ie-13 | If-13 |
| 2-methyl-7-hydroxybenzothiophene | Ia-14 | Ib-14 | Ic-14 | Id-14 | Ie-14 | If-14 |
| 2-methyl-7-methoxybenzothiophene | Ia-15 | Ia-15 | Ic-15 | Id-15 | Ie-15 | If-15 |
| 2-methyl-5-hydroxybenzothiophene | Ia-16 | Ib-16 | Ic-16 | Id-16 | Ie-16 | If-16 |
| 3-methylbenzothiophene | Ia-17 | Ib-17 | Ic-17 | Id-17 | Ie-17 | If-17 |
| 2,3-dimethylbenzothiophene | Ia-18 | Ib-18 | Ic-18 | Id-18 | Ie-18 | If-18 |
| 3-methyl-6-methylbenzothiophene | Ia-19 | Ib-19 | Ic-19 | Id-19 | Ie-19 | If-19 |
| 3-methyl-6-methylbenzothiophene (isomer) | Ia-20 | Ib-20 | Ic-20 | Id-20 | Ie-20 | Ief-20 |

TABLE 3

Structure: norbornane with -NH-C(=O)-R¹ substituent and R³ substituent

| R¹ | Ia | Ib | Ic | Id | Ie | If |
|---|---|---|---|---|---|---|
| 3-methyl-7-hydroxybenzothiophene | Ia-21 | Ib-21 | Ic-21 | Id-21 | Ie-21 | If-21 |
| 3-methyl-6-hydroxybenzothiophene | Ia-22 | Ib-22 | Ic-22 | Id-22 | Ie-22 | If-22 |
| 3-methyl-5-hydroxybenzothiophene | Ia-23 | Ib-23 | Ic-23 | Id-23 | Ie-23 | If-23 |
| 3-methyl-4-hydroxybenzothiophene | Ia-24 | Ib-24 | Ic-24 | Id-24 | Ie-24 | If-24 |
| 3-methyl-5-acetoxybenzothiophene | Ia-25 | Ia-25 | Ic-25 | Id-25 | Ie-25 | If-25 |
| 3-methyl-5-methoxybenzothiophene | Ia-26 | Ib-26 | Ic-26 | Id-26 | Ie-26 | If-26 |
| 3-methyl-6-fluorobenzothiophene | Ia-27 | Ib-27 | Ic-27 | Id-27 | Ie-27 | If-27 |
| 3-methyl-5-fluorobenzothiophene | Ia-28 | Ib-28 | Ic-28 | Id-28 | Ie-28 | If-28 |
| 3-methyl-6-bromobenzothiophene | Ia-29 | Ib-29 | Ic-29 | Id-29 | Ie-29 | If-29 |
| 3-methyl-5-bromobenzothiophene | Ia-30 | Ib-30 | Ic-30 | Id-30 | Ie-30 | If-30 |

TABLE 4
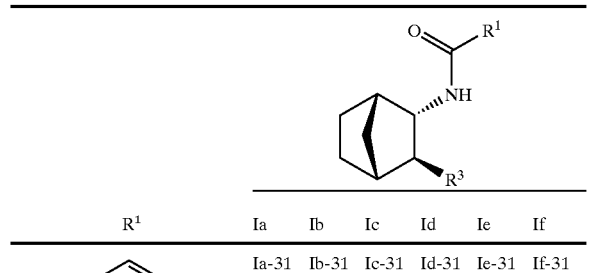
| R¹ | Ia | Ib | Ic | Id | Ie | If |
|---|---|---|---|---|---|---|
| 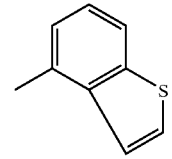 | Ia-31 | Ib-31 | Ic-31 | Id-31 | Ie-31 | If-31 |
| 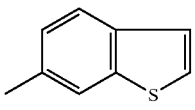 | Ia-32 | Ib-32 | Ic-32 | Id-32 | Ie-32 | If-32 |
| 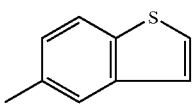 | Ia-33 | Ib-33 | Ic-33 | Id-33 | Ie-33 | If-33 |
| 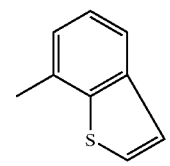 | Ia-34 | Ib-34 | Ic-34 | Id-34 | Ie-34 | If-34 |
| 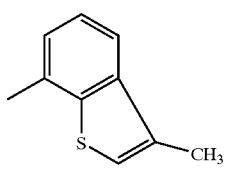 | Ia-35 | Ia-35 | Ic-35 | Id-35 | Ie-35 | If-35 |
| 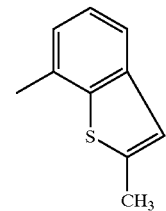 | Ia-36 | Ib-36 | Ic-36 | Id-36 | Ie-36 | If-36 |
| 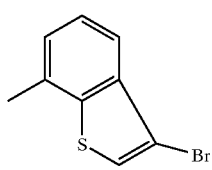 | Ia-37 | Ib-37 | Ic-37 | Id-37 | Ie-37 | If-37 |
| 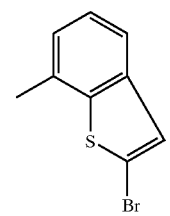 | Ia-38 | Ib-38 | Ic-38 | Id-38 | Ie-38 | If-38 |
TABLE 4-continued
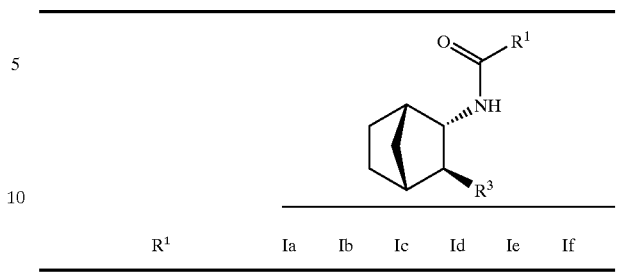
| R¹ | Ia | Ib | Ic | Id | Ie | If |
|---|---|---|---|---|---|---|
| 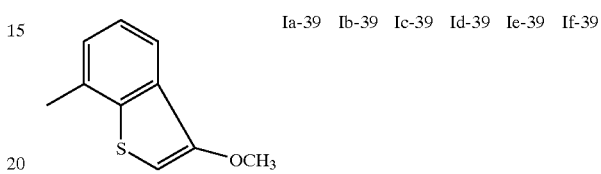 | Ia-39 | Ib-39 | Ic-39 | Id-39 | Ie-39 | If-39 |
| 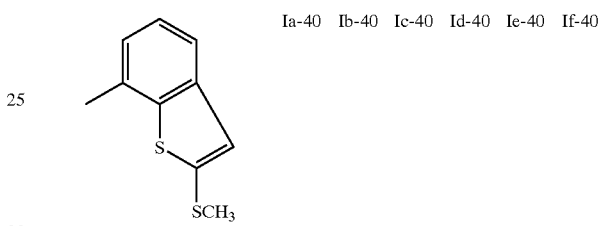 | Ia-40 | Ib-40 | Ic-40 | Id-40 | Ie-40 | If-40 |
TABLE 5
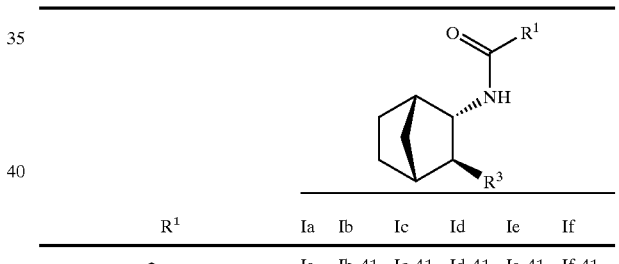
| R¹ | Ia | Ib | Ic | Id | Ie | If |
|---|---|---|---|---|---|---|
| 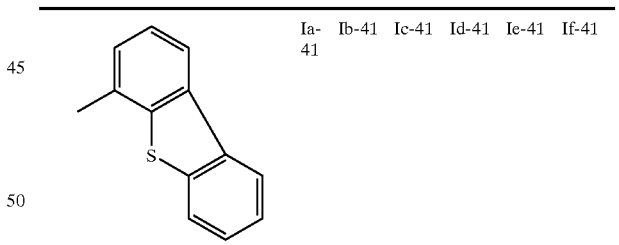 | Ia-41 | Ib-41 | Ic-41 | Id-41 | Ie-41 | If-41 |
| 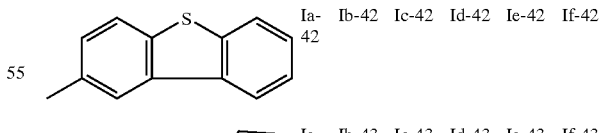 | Ia-42 | Ib-42 | Ic-42 | Id-42 | Ie-42 | If-42 |
| 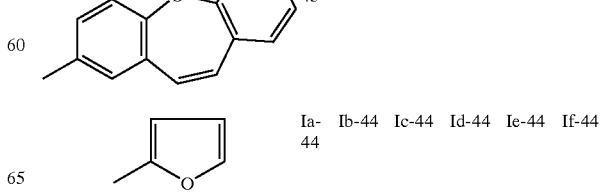 | Ia-43 | Ib-43 | Ic-43 | Id-43 | Ie-43 | If-43 |
| | Ia-44 | Ib-44 | Ic-44 | Id-44 | Ie-44 | If-44 |

TABLE 5-continued

| R¹ | Ia | Ib | Ic | Id | Ie | If |
|---|---|---|---|---|---|---|
| (3-methylfuran) | Ia-45 | Ib-45 | Ic-45 | Id-45 | Ie-45 | If-45 |
| (2-methylbenzofuran) | Ia-46 | Ib-46 | Ic-46 | Id-46 | Ie-46 | If-46 |
| (3-methylbenzofuran) | Ia-47 | Ib-47 | Ic-47 | Id-47 | Ie-47 | If-47 |
| (3,7-dimethylbenzofuran) | Ia-48 | Ib-48 | Ic-48 | Id-48 | Ie-48 | If-48 |
| (7-methoxymethyl-3-methylbenzofuran) | Ia-49 | Ib-49 | Ic-49 | Id-49 | Ie-49 | If-49 |
| (7-hydroxy-3-methylbenzofuran) | Ia-50 | Ib-50 | Ic-50 | Id-50 | Ie-50 | If-50 |

TABLE 6

| R¹ | Ia | Ib | Ic | Id | Ie | If |
|---|---|---|---|---|---|---|
| (6-hydroxy-3-methylbenzofuran) | Ia-51 | Ib-51 | Ic-51 | Id-51 | Ie-51 | If-51 |
| (5-hydroxy-3-methylbenzofuran) | Ia-52 | Ib-52 | Ic-52 | Id-52 | Ie-52 | If-52 |
| (4-hydroxy-3-methylbenzofuran) | Ia-53 | Ib-53 | Ic-53 | Id-53 | Ie-53 | If-53 |
| (6-fluoro-3-methylbenzofuran) | Ia-54 | Ib-54 | Ic-54 | Id-54 | Ie-54 | If-54 |
| (5-fluoro-3-methylbenzofuran) | Ia-55 | Ia-55 | Ic-55 | Id-55 | Ie-55 | If-55 |
| (7-methylbenzofuran) | Ia-56 | Ib-56 | Ic-56 | Id-56 | Ie-56 | If-56 |
| (methyldibenzofuran) | Ia-57 | Ib-57 | Ic-57 | Id-57 | Ie-57 | If-57 |
| (methyldibenzofuran) | Ia-58 | Ib-58 | Ic-58 | Id-58 | Ie-58 | If-58 |
| (2-methylpyrrole) | Ia-59 | Ib-59 | Ic-59 | Id-59 | Ie-59 | If-59 |
| (1,2-dimethylpyrrole) | Ia-60 | Ib-60 | Ic-60 | Id-60 | Ie-60 | If-60 |

TABLE 7

[Structure: norbornane with NHC(O)R¹ and R³ substituents]

| R¹ | Ia | Ib | Ic | Id | Ie | If |
|---|---|---|---|---|---|---|
| 3-methyl-1H-pyrrole | Ia-61 | Ib-61 | Ic-61 | Id-61 | Ie-61 | If-61 |
| 1-methyl-3-methyl-pyrrole | Ia-62 | Ib-62 | Ic-62 | Id-62 | Ie-62 | If-62 |
| 2-methyl-1H-indole | Ia-63 | Ib-63 | Ic-63 | Id-63 | Ie-63 | If-63 |
| 3-methyl-1H-indole | Ia-64 | Ib-64 | Ic-64 | Id-64 | Ie-64 | If-64 |
| methyl-thieno-pyrrole | Ia-65 | Ia-65 | Ic-65 | Id-65 | Ie-65 | If-65 |
| methyl-pyrrolo-thiophene | Ia-66 | Ib-66 | Ic-66 | Id-66 | Ie-66 | If-66 |
| methyl-thieno-pyrrole | Ia-67 | Ib-67 | Ic-67 | Id-67 | Ie-67 | If-67 |
| methyl-thieno-pyrrole | Ia-68 | Ib-68 | Ic-68 | Id-68 | Ie-68 | If-68 |
| N-methyl-thieno-pyrrole | Ia-69 | Ib-69 | Ic-69 | Id-69 | Ie-69 | If-69 |

TABLE 7-continued

[Structure: norbornane with NHC(O)R¹ and R³ substituents]

| R¹ | Ia | Ib | Ic | Id | Ie | If |
|---|---|---|---|---|---|---|
| N-methyl-thieno-pyrrole | Ia-70 | Ib-70 | Ic-70 | Id-70 | Ie-70 | If-70 |

TABLE 8

[Structure: norbornane with NHC(O)R¹ and R³ substituents]

| R¹ | Ia | Ib | Ic | Id | Ie | If |
|---|---|---|---|---|---|---|
| methyl-thieno-pyrrole | Ia-71 | Ib-71 | Ic-71 | Id-71 | Ie-71 | If-71 |
| N-methyl-thieno-pyrrole | Ia-72 | Ib-72 | Ic-72 | Id-72 | Ie-72 | If-72 |
| N-methyl-pyrrolo-thiophene | Ia-73 | Ib-73 | Ic-73 | Id-73 | Ie-73 | If-73 |
| methyl-thieno-thiophene | Ia-74 | Ib-74 | Ic-74 | Id-74 | Ie-74 | If-74 |
| methyl-thieno-thiophene | Ia-75 | Ia-75 | Ic-75 | Id-75 | Ie-75 | If-75 |
| 6-methyl-1H-indole | Ia-76 | Ib-76 | Ic-76 | Id-76 | Ie-76 | If-76 |

TABLE 8-continued
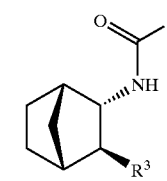
| R¹ | Ia | Ib | Ic | Id | Ie | If |
|---|---|---|---|---|---|---|
| 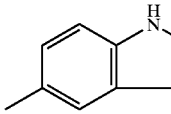 | Ia-77 | Ib-77 | Ic-77 | Id-77 | Ie-77 | If-77 |
| 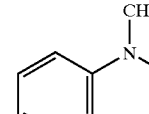 | Ia-78 | Ib-78 | Ic-78 | Id-78 | Ie-78 | If-78 |
| 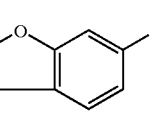 | Ia-79 | Ib-79 | Ic-79 | Id-79 | Ie-79 | If-79 |
| 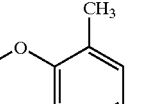 | Ia-80 | Ib-80 | Ic-80 | Id-80 | Ie-80 | If-80 |
TABLE 9
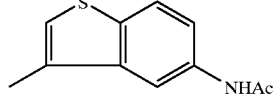
| R¹ | Ia | Ib | Ic | Id | Ie | If |
|---|---|---|---|---|---|---|
| 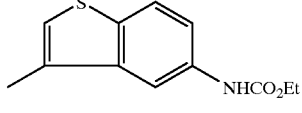 | Ia-81 | Ib-81 | Ic-81 | Id-81 | Ie-81 | If-81 |
| 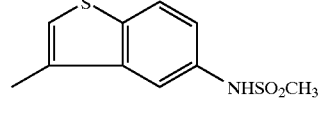 | Ia-82 | Ib-82 | Ic-82 | Id-82 | Ie-82 | If-82 |
TABLE 9-continued
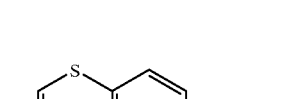
| R¹ | Ia | Ib | Ic | Id | Ie | If |
|---|---|---|---|---|---|---|
| 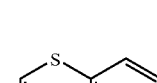 | Ia-83 | Ib-83 | Ic-83 | Id-83 | Ie-83 | If-83 |
| 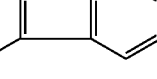 | Ia-84 | Ib-84 | Ic-84 | Id-84 | Ie-84 | If-84 |
|  | Ia-85 | Ib-85 | Ic-85 | Id-85 | Ie-85 | If-85 |
| 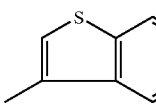 | Ia-86 | Ib-86 | Ic-86 | Id-86 | Ie-86 | If-86 |
|  | Ia-87 | Ib-87 | Ic-87 | Id-87 | Ie-87 | If-87 |
|  | Ia-88 | Ib-88 | Ic-88 | Id-88 | Ie-88 | If-88 |
|  | Ia-89 | Ib-89 | Ic-89 | Id-89 | Ie-89 | If-89 |
|  | Ia-90 | Ib-90 | Ic-90 | Id-90 | Ie-90 | If-90 |

TABLE 10

| R¹ | Ia | Ib | Ic | Id | Ie | If |
|---|---|---|---|---|---|---|
| 3-methylbenzothiophene-NHSO₂NH₂ | Ia-91 | Ib-91 | Ic-91 | Id-91 | Ie-91 | If-91 |
| 3-methylbenzothiophene-NHCO₂Et | Ia-92 | Ib-92 | Ic-92 | Id-92 | Ie-92 | If-92 |
| 3-methylbenzothiophene-NHCONH₂ | Ia-93 | Ib-93 | Ic-93 | Id-93 | Ie-93 | If-93 |
| 3-methylbenzothiophene-CH₂NHAc | Ia-94 | Ib-94 | Ic-94 | Id-94 | Ie-94 | If-94 |
| 3-methylbenzothiophene-CH₂NHCO₂Et | Ia-95 | Ib-95 | Ic-95 | Id-95 | Ie-95 | If-95 |
| 3-methylbenzothiophene-CH₂NHSO₂CH₃ | Ia-96 | Ib-96 | Ic-96 | Id-96 | Ie-96 | If-96 |
| 3-methylbenzothiophene-CH₂NHCONH₂ | Ia-97 | Ib-97 | Ic-97 | Id-97 | Ie-97 | If-97 |
| 3-methylbenzothiophene-CH₂CONH₂ | Ia-98 | Ib-98 | Ic-98 | Id-98 | Ie-98 | If-98 |
| 3-methylbenzothiophene-CONH₂ | Ia-99 | Ib-99 | Ic-99 | Id-99 | Ie-99 | If-99 |
| 3-methylbenzothiophene-CO₂H | Ia-100 | Ib-100 | Ic-100 | Id-100 | Ie-100 | If-100 |

TABLE 11

| R¹ | Ia | Ib | Ic | Id | Ie | If |
|---|---|---|---|---|---|---|
| 3-methylbenzothiophene-5-CONHOCH₃ | Ia-101 | Ib-101 | Ic-101 | Id-101 | Ie-101 | If-101 |
| 3-methylbenzothiophene-5-CONHSO₂CH₃ | Ia-102 | Ib-102 | Ic-102 | Id-102 | Ie-102 | If-102 |
| 3-methylbenzothiophene-6-CONH₂ | Ia-103 | Ib-103 | Ic-103 | Id-103 | Ie-103 | If-103 |
| 3-methylbenzothiophene-7-CONH₂ | Ia-104 | Ib-104 | Ic-104 | Id-104 | Ie-104 | If-104 |
| 7-methylbenzothiophene-3-CONH₂ | Ia-105 | Ib-105 | Ic-105 | Id-105 | Ie-105 | If-105 |
| 3-methylbenzothiophene-5-CONHCH₃ | Ia-106 | Ib-106 | Ic-106 | Id-106 | Ie-106 | If-106 |
| 3-methylbenzothiophene-5-CON(CH₃)₂ | Ia-107 | Ib-107 | Ic-107 | Id-107 | Ie-107 | If-107 |
| 3-methylbenzothiophene-5-CONHEt | Ia-108 | Ib-108 | Ic-108 | Id-108 | Ie-108 | If-108 |
| 3-methylbenzothiophene-5-SO₂NH₂ | Ia-109 | Ib-109 | Ic-109 | Id-109 | Ie-109 | If-109 |
| 3-methylbenzothiophene-6-SO₂NH₂ | Ia-110 | Ib-110 | Ic-110 | Id-110 | Ie-110 | If-110 |

TABLE 12

| R¹ | Ia | Ib | Ic | Id | Ie | If |
|---|---|---|---|---|---|---|
| 3,5-dimethyl-benzothiophene-6-sulfonamide | Ia-111 | Ib-111 | Ic-111 | Id-111 | Ie-111 | If-111 |
| 3-methyl-5-fluoro-benzothiophene-6-sulfonamide | Ia-112 | Ib-112 | Ic-112 | Id-112 | Ie-112 | If-112 |
| 7-methyl-benzothiophene-3-sulfonamide | Ia-113 | Ib-113 | Ic-113 | Id-113 | Ie-113 | If-113 |
| 7-methyl-benzothiophene-3-N,N-dimethylsulfonamide | Ia-114 | Ib-114 | Ic-114 | Id-114 | Ie-114 | If-114 |
| 3,5,7-trimethyl-benzothiophene | Ia-115 | Ib-115 | Ic-115 | Id-115 | Ie-115 | If-115 |
| 6-methyl-thieno-benzodioxole | Ia-116 | Ib-116 | Ic-116 | Id-116 | Ie-116 | If-116 |
| 3,4,7-trimethyl-benzothiophene | Ia-117 | Ib-117 | Ic-117 | Id-117 | Ie-117 | If-117 |
| 6-methyl-thieno-dihydrobenzofuran | Ia-118 | Ib-118 | Ic-118 | Id-118 | Ie-118 | If-118 |

TABLE 12-continued
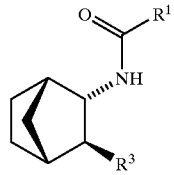
| R¹ | Ia | Ib | Ic | Id | Ie | If |
|---|---|---|---|---|---|---|
| 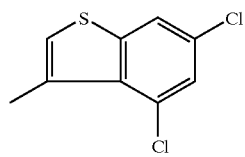 | Ia-119 | Ib-119 | Ic-119 | Id-119 | Ie-119 | If-119 |
| 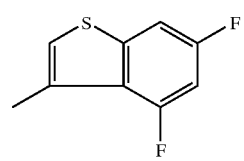 | Ia-120 | Ib-120 | Ic-120 | Id-120 | Ie-120 | If-120 |
TABLE 13
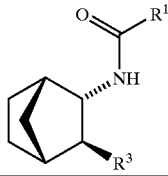
| R¹ | Ia | Ib | Ic | Id | Ie | If |
|---|---|---|---|---|---|---|
| 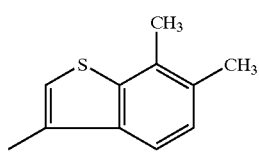 | Ia-121 | Ib-121 | Ic-121 | Id-121 | Ie-121 | If-121 |
| 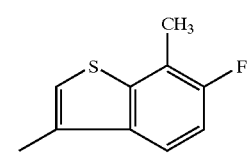 | Ia-122 | Ib-122 | Ic-122 | Id-122 | Ie-122 | If-122 |
| 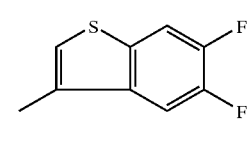 | Ia-123 | Ib-123 | Ic-123 | Id-123 | Ie-123 | If-123 |
| 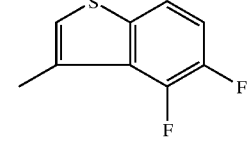 | Ia-124 | Ib-124 | Ic-124 | Id-124 | Ie-124 | If-124 |

TABLE 13-continued
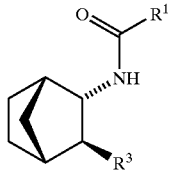
| R[1] | Ia | Ib | Ic | Id | Ie | If |
|---|---|---|---|---|---|---|
| 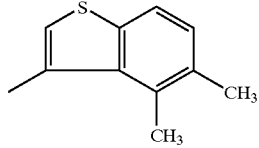 | Ia-125 | Ib-125 | Ic-125 | Id-125 | Ie-125 | If-125 |
| 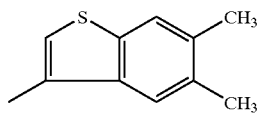 | Ia-126 | Ib-126 | Ic-126 | Id-126 | Ie-126 | If-126 |
| 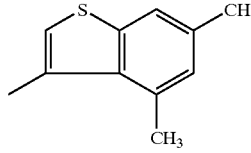 | Ia-127 | Ib-127 | Ic-127 | Id-127 | Ie-127 | If-127 |
| 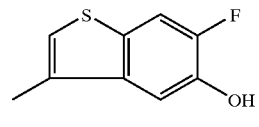 | Ia-128 | Ib-128 | Ic-128 | Id-128 | Ie-128 | If-128 |
| 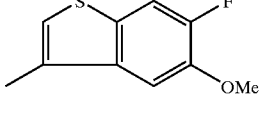 | Ia-129 | Ib-129 | Ic-129 | Id-129 | Ie-129 | If-129 |
| 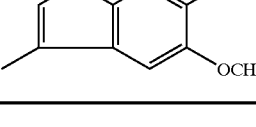 | Ia-130 | Ib-130 | Ic-130 | Id-130 | Ie-130 | If-130 |
TABLE 14
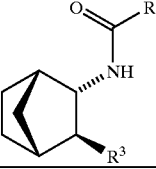
| R[1] | Ia | Ib | Ic | Id | Ie | If |
|---|---|---|---|---|---|---|
| 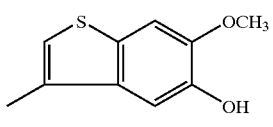 | Ia-131 | I-131b | Ic-131 | Id-131 | Ie-131 | If-131 |

TABLE 14-continued

| R¹ | Ia | Ib | Ic | Id | Ie | If |
|---|---|---|---|---|---|---|
| 3-methylbenzofuran-5-yl-NHAc | Ia-132 | I-132b | Ic-132 | Id-132 | Ie-132 | If-132 |
| 3-methylbenzofuran-5-yl-NHCO₂Et | Ia-133 | I-133b | Ic-133 | Id-133 | Ie-133 | If-133 |
| 3-methylbenzofuran-5-yl-NHSO₂CH₃ | Ia-134 | I-134b | Ic-134 | Id-134 | Ie-134 | If-134 |
| 3-methylbenzofuran-5-yl-NHCONH₂ | Ia-135 | I-135b | Ic-135 | Id-135 | Ie-135 | If-135 |
| 3-methylbenzofuran-5-yl-CH₂NHAc | Ia-136 | I-136b | Ic-136 | Id-136 | Ie-136 | If-136 |
| 3-methylbenzofuran-5-yl-CH₂NHCO₂Et | Ia-137 | I-137b | Ic-137 | Id-137 | Ie-137 | If-137 |
| 3-methylbenzofuran-5-yl-CH₂NHSO₂CH₃ | Ia-138 | I-138b | Ic-138 | Id-138 | Ie-138 | If-138 |
| 3-methylbenzofuran-5-yl-CH₂NHCONH₂ | Ia-139 | I-139b | Ic-139 | Id-139 | Ie-139 | If-139 |
| 3-methylbenzofuran-5-yl-CH₂CONH₂ | Ia-140 | I-140b | Ic-140 | Id-140 | Ie-140 | If-140 |

TABLE 15
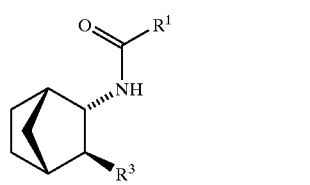
| R¹ | Ia | Ib | Ic | Id | Ie | If |
|---|---|---|---|---|---|---|
| 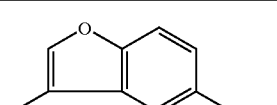 | Ia-141 | Ib-141 | Ic-141 | Id-141 | Ie-141 | If-141 |
| 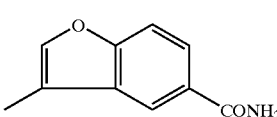 | Ia-142 | Ib-142 | Ic-142 | Id-142 | Ie-142 | If-142 |
| 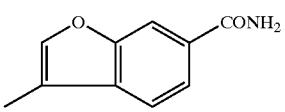 | Ia-143 | Ib-143 | Ic-143 | Id-143 | Ie-143 | If-143 |
| 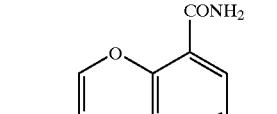 | Ia-144 | Ib-144 | Ic-144 | Id-144 | Ie-144 | If-144 |
| 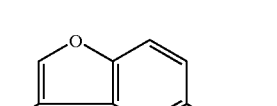 | Ia-145 | Ib-145 | Ic-145 | Id-145 | Ie-145 | If-145 |
| 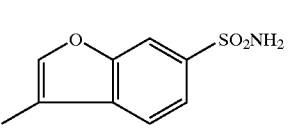 | Ia-146 | Ib-146 | Ic-146 | Id-146 | Ie-146 | If-146 |
| 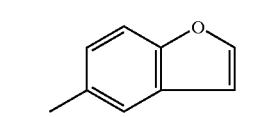 | Ia-147 | Ib-147 | Ic-147 | Id-147 | Ie-147 | If-147 |
| 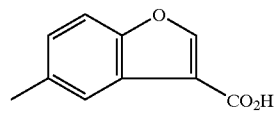 | Ia-148 | Ib-148 | Ic-148 | Id-148 | Ie-148 | If-148 |
| 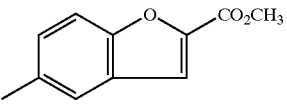 | Ia-149 | Ib-149 | Ic-149 | Id-149 | Ie-149 | If-149 |
| 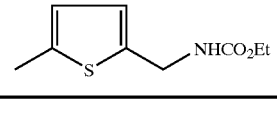 | Ia-150 | Ib-150 | Ic-150 | Id-150 | Ie-150 | If-150 |

TABLE 16

| R¹ | Ia | Ib | Ic | Id | Ie | If |
|---|---|---|---|---|---|---|
| 5-methyl-thiophen-2-yl-CH₂-NHCONH₂ | Ia-151 | Ib-151 | Ic-151 | Id-151 | Ie-151 | If-151 |
| 5-methyl-thiophen-2-yl-CH₂-NHSO₂NH₂ | Ia-152 | Ib-152 | Ic-152 | Id-152 | Ie-152 | If-152 |
| 5-methyl-thiophen-2-yl-CONH₂ | Ia-153 | Ib-153 | Ic-153 | Id-153 | Ie-153 | If-153 |
| 5-methyl-thiophen-2-yl-SO₂NH₂ | Ia-154 | Ib-154 | Ic-154 | Id-154 | Ie-154 | If-154 |
| 4-methyl-thiophen-2-yl-SO₃NH₂ | Ia-155 | Ib-155 | Ic-155 | Id-155 | Ie-155 | If-155 |
| 5-methyl-thiophen-2-yl-CO₂H | Ia-156 | Ib-156 | Ic-156 | Id-156 | Ie-156 | If-156 |
| 5-methyl-thiophen-2-yl-CH₂-CONH₂ | Ia-157 | Ib-157 | Ic-157 | Id-157 | Ie-157 | If-157 |
| 3-methyl-benzothiophen-5-yl-CONHOH | Ia-158 | Ib-158 | Ic-158 | Id-158 | Ie-158 | If-158 |
| 3-methyl-dithienobenzene | Ia-159 | Ib-159 | Ic-159 | Id-159 | Ie-159 | If-159 |
| 2-methyl-dithienobenzene | Ia-160 | Ib-160 | Ic-160 | Id-160 | Ie-160 | If-160 |

TABLE 17
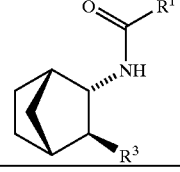
| R¹ | Ia | Ib | Ic | Id | Ie | If |
|---|---|---|---|---|---|---|
| 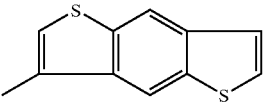 | Ia-161 | Ib-161 | Ic-161 | Id-161 | Ie-161 | If-161 |
| 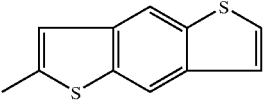 | Ia-162 | Ib-162 | Ic-162 | Id-162 | Ie-162 | If-162 |
| 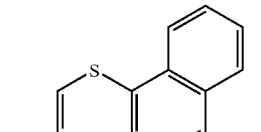 | Ia-163 | Ib-163 | Ic-163 | Id-163 | Ie-163 | If-163 |
| 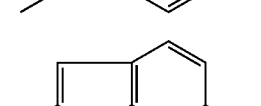 | Ia-164 | Ib-164 | Ic-164 | Id-164 | Ie-164 | If-164 |
| 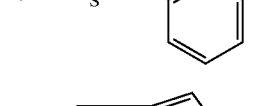 | Ia-165 | Ib-165 | Ic-165 | Id-165 | Ie-165 | If-165 |
| 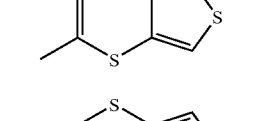 | Ia-166 | Ib-166 | Ic-166 | Id-166 | Ie-166 | If-166 |
TABLE 18
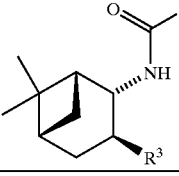
| R¹ | IIa | IIb | IIc | IId | IIe | IIf |
|---|---|---|---|---|---|---|
| 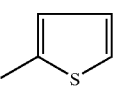 | IIa-1 | IIb-1 | IIc-1 | IId-1 | IIe-1 | IIf-1 |
| 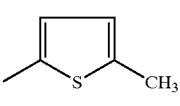 | IIa-2 | IIb-2 | IIc-2 | IId-2 | IIe-2 | IIf-2 |
TABLE 18-continued
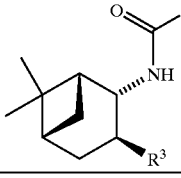
| R¹ | IIa | IIb | IIc | IId | IIe | IIf |
|---|---|---|---|---|---|---|
| 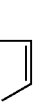 | IIa-3 | IIb-3 | IIc-3 | IId-3 | IIe-3 | IIf-3 |
| 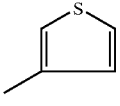 | IIa-4 | IIb-4 | IIc-4 | IId-4 | IIe-4 | IIf-4 |

TABLE 18-continued

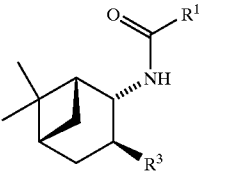

| R¹ | IIa | IIb | IIc | IId | IIe | IIf |
|---|---|---|---|---|---|---|
| (2-methyl-4-thienyl)-CH₃ | IIa-5 | IIb-5 | IIc-5 | IId-5 | IIe-5 | IIf-5 |
| (isopropyl-thienyl) | IIa-6 | IIb-6 | IIc-6 | IId-6 | IIe-6 | IIf-6 |
| (2,3-dimethylthienyl) | IIa-7 | IIb-7 | IIc-7 | IId-7 | IIe-7 | IIf-7 |
| (3-methylthienyl) | IIa-8 | IIb-8 | IIc-8 | IId-8 | IIe-8 | IIf-8 |
| (2-bromo-4-methylthienyl) | IIa-9 | IIb-9 | IIc-9 | IId-9 | IIe-9 | IIf-9 |
| (2-methoxy-4-methylthienyl) | IIa-10 | IIb-10 | IIc-10 | IId-10 | IIe-10 | IIf-10 |

TABLE 19

| R¹ | IIa | IIb | IIc | IId | IIe | IIf |
|---|---|---|---|---|---|---|
| (2-methylthio-4-methylthienyl) | IIa-11 | IIb-11 | IIc-11 | IId-11 | IIe-11 | IIf-11 |
| (benzothienyl) | IIa-12 | IIb-12 | IIc-12 | IId-12 | IIe-12 | IIf-12 |
| (methyl-benzothienyl) | IIa-13 | IIb-13 | IIc-13 | IId-13 | IIe-13 | IIf-13 |

TABLE 19-continued
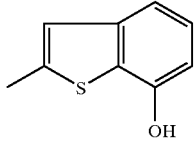
| R¹ | IIa | IIb | IIc | IId | IIe | IIf |
|---|---|---|---|---|---|---|
| 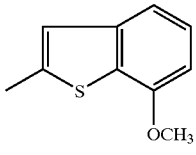 | IIa-14 | IIb-14 | IIc-14 | IId-14 | IIe-14 | IIf-14 |
| 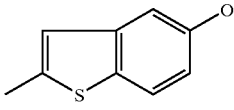 | IIa-15 | IIb-15 | IIc-15 | IId-15 | IIe-15 | IIf-15 |
| 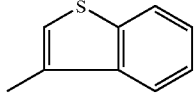 | IIa-16 | IIb-16 | IIc-16 | IId-16 | IIe-16 | IIf-16 |
| 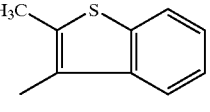 | IIa-17 | IIb-17 | IIc-17 | IId-17 | IIe-17 | IIf-17 |
| 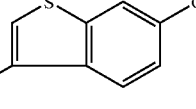 | IIa-18 | IIb-18 | IIc-18 | IId-18 | IIe-18 | IIf-18 |
| 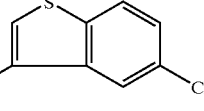 | IIa-19 | IIb-19 | IIc-19 | IId-19 | IIe-19 | IIf-19 |
| 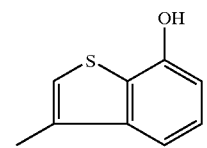 | IIa-20 | IIb-20 | IIc-20 | IId-20 | IIe-20 | IIf-20 |
TABLE 20
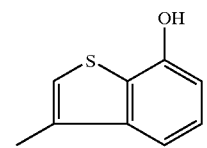
| R¹ | IIa | IIb | IIc | IId | IIe | IIf |
|---|---|---|---|---|---|---|
| 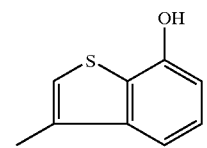 | IIa-21 | IIb-21 | IIc-21 | IId-21 | IIe-21 | IIf-21 |

TABLE 20-continued
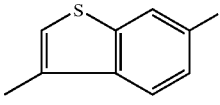
| R¹ | IIa | IIb | IIc | IId | IIe | IIf |
|---|---|---|---|---|---|---|
| 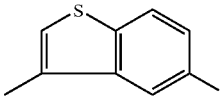 | IIa-22 | IIb-22 | IIc-22 | IId-22 | IIe-22 | IIf-22 |
| 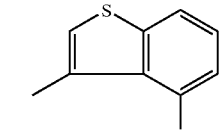 | IIa-23 | IIb-23 | IIc-23 | IId-23 | IIe-23 | IIf-23 |
| 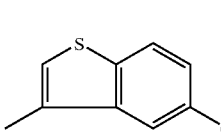 | IIa-24 | IIb-24 | IIc-24 | IId-24 | IIe-24 | IIf-24 |
| 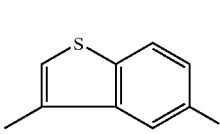 | IIa-25 | IIb-25 | IIc-25 | IId-25 | IIe-25 | IIf-25 |
| 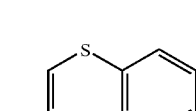 | IIa-26 | IIb-26 | IIc-26 | IId-26 | IIe-26 | IIf-26 |
| 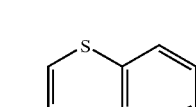 | IIa-27 | IIb-27 | IIc-27 | IId-27 | IIe-27 | IIf-27 |
| 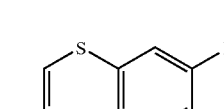 | IIa-28 | IIb-28 | IIc-28 | IId-28 | IIe-28 | IIf-28 |
| 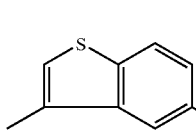 | IIa-29 | IIb-29 | IIc-29 | IId-29 | IIe-29 | IIf-29 |
|  | IIa-30 | IIb-30 | IIc-30 | IId-30 | IIe-30 | IIf-30 |

TABLE 21
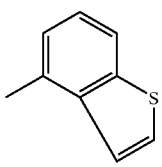
| R¹ | IIA | IIb | IIc | IId | IIe | IIf |
|---|---|---|---|---|---|---|
| 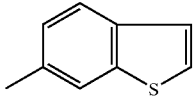 | IIa-31 | IIb-31 | IIc-31 | IId-31 | IIe-31 | IIf-31 |
| 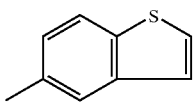 | IIa-32 | IIb-32 | IIc-32 | IId-32 | IIe-32 | IIf-32 |
| 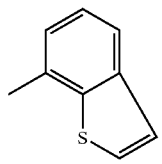 | IIa-33 | IIb-33 | IIc-33 | IId-33 | IIe-33 | IIf-33 |
| 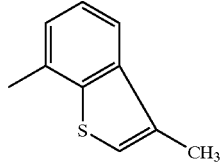 | IIa-34 | IIb-34 | IIc-34 | IId-34 | IIe-34 | IIf-34 |
| 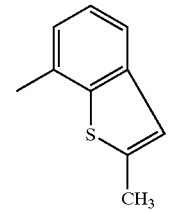 | IIa-35 | IIb-35 | IIc-35 | IId-35 | IIe-35 | IIf-35 |
| 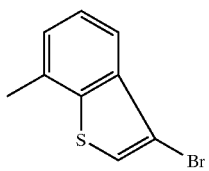 | IIa-36 | IIb-36 | IIc-36 | IId-36 | IIe-36 | IIf-36 |
| 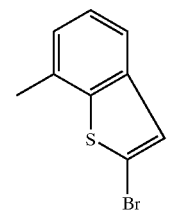 | IIa-37 | IIb-37 | IIc-37 | IId-37 | IIe-37 | IIf-37 |
|  | IIa-38 | IIb-38 | IIc-38 | IId-38 | IIe-38 | IIf-38 |

TABLE 21-continued
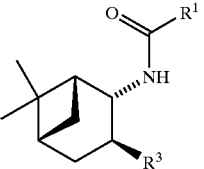
| R¹ | IIA | IIb | IIc | IId | IIe | IIf |
|---|---|---|---|---|---|---|
| 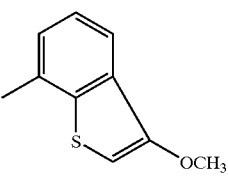 | IIa-39 | IIb-39 | IIc-39 | IId-39 | IIe-39 | IIf-39 |
| 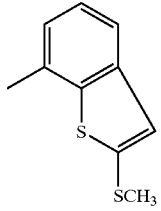 | IIa-40 | IIb-40 | IIc-40 | IId-40 | IIe-40 | IIf-40 |
TABLE 22
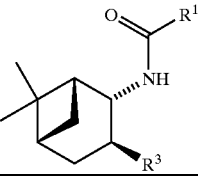
| R¹ | IIa | IIb | IIc | IId | IIe | IIf |
|---|---|---|---|---|---|---|
| 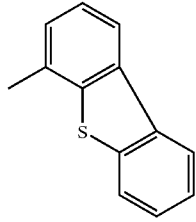 | IIa-41 | IIb-41 | IIc-41 | IId-41 | IIe-41 | IIf-41 |
| 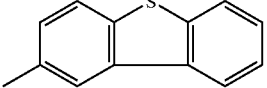 | IIa-42 | IIb-42 | IIc-42 | IId-42 | IIe-42 | IIf-42 |
| 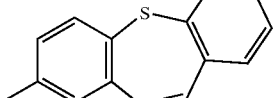 | IIa-43 | IIb-43 | IIc-43 | IId-43 | IIe-43 | IIf-43 |
| 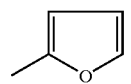 | IIa-44 | IIb-44 | IIc-44 | IId-44 | IIe-44 | IIf-44 |

TABLE 22-continued
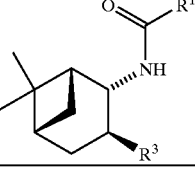
| R¹ | IIa | IIb | IIc | IId | IIe | IIf |
|---|---|---|---|---|---|---|
| 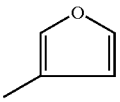 | IIa-45 | IIb-45 | IIc-45 | IId-45 | IIe-45 | IIf-45 |
| 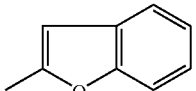 | IIa-46 | IIb-46 | IIc-46 | IId-46 | IIe-46 | IIf-46 |
| 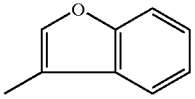 | IIa-47 | IIb-47 | IIc-47 | IId-47 | IIe-47 | IIf-47 |
| 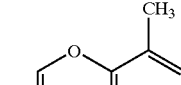 | IIa-48 | IIb-48 | IIc-48 | IId-48 | IIe-48 | IIf-48 |
| 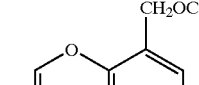 | IIa-49 | IIb-49 | IIc-49 | IId-49 | IIe-49 | IIf-49 |
| 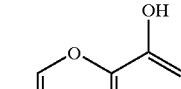 | IIa-50 | IIb-50 | IIc-50 | IId-50 | IIe-50 | IIf-50 |
TABLE 23
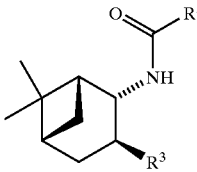
| R¹ | IIa | IIb | IIc | IId | IIe | IIf |
|---|---|---|---|---|---|---|
| 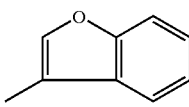 | IIa-51 | IIb-51 | IIc-51 | IId-51 | IIe-51 | IIf-51 |
| 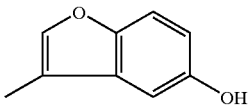 | IIa-52 | IIb-52 | IIc-52 | IId-52 | IIe-52 | IIf-52 |

TABLE 23-continued

| R¹ | IIa | IIb | IIc | IId | IIe | IIf |
|---|---|---|---|---|---|---|
| 3-methyl-4-hydroxybenzofuran | IIa-53 | IIb-53 | IIc-53 | IId-53 | IIe-53 | IIf-53 |
| 3-methyl-6-fluorobenzofuran | IIa-54 | IIb-54 | IIc-54 | IId-54 | IIe-54 | IIf-54 |
| 3-methyl-5-fluorobenzofuran | IIa-55 | IIb-55 | IIc-55 | IId-55 | IIe-55 | IIf-55 |
| 7-methylbenzofuran | IIa-56 | IIb-56 | IIc-56 | IId-56 | IIe-56 | IIf-56 |
| 3-methyldibenzofuran | IIa-57 | IIb-57 | IIc-57 | IId-57 | IIe-57 | IIf-57 |
| 2-methyldibenzofuran | IIa-58 | IIb-58 | IIc-58 | IId-58 | IIe-58 | IIf-58 |
| 2-methylpyrrole | IIa-59 | IIb-59 | IIc-59 | IId-59 | IIe-59 | IIf-59 |
| 1-methyl-2-methylpyrrole | IIa-60 | IIb-60 | IIc-60 | IId-60 | IIe-60 | IIf-60 |

TABLE 24
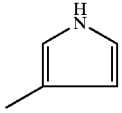
| R¹ | IIa | IIb | IIc | IId | IIe | IIf |
|---|---|---|---|---|---|---|
| 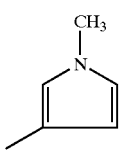 | IIa-61 | IIb-61 | IIc-61 | IId-61 | IIe-61 | IIf-61 |
| 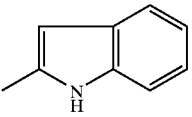 | IIa-62 | IIb-62 | IIc-62 | IId-62 | IIe-62 | IIf-62 |
| 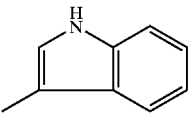 | IIa-63 | IIb-63 | IIc-63 | IId-63 | IIe-63 | IIf-63 |
| 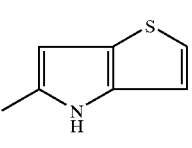 | IIa-64 | IIb-64 | IIc-64 | IId-64 | IIe-64 | IIf-64 |
| 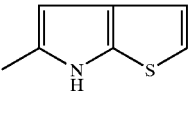 | IIa-65 | IIb-65 | IIc-65 | IId-65 | IIe-65 | IIf-65 |
| 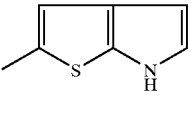 | IIa-66 | IIb-66 | IIc-66 | IId-66 | IIe-66 | IIf-66 |
| 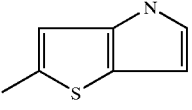 | IIa-67 | IIb-67 | IIc-67 | IId-67 | IIe-67 | IIf-67 |
| 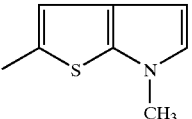 | IIa-68 | IIb-68 | IIc-68 | IId-68 | IIe-68 | IIf-68 |
| 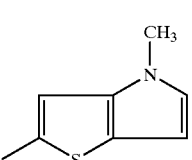 | IIa-69 | IIb-69 | IIc-69 | IId-69 | IIe-69 | IIf-69 |
|  | IIa-70 | IIb-70 | IIc-70 | IId-70 | IIe-70 | IIf-70 |

TABLE 25

| R¹ | IIa | IIb | IIc | IId | IIe | IIf |
|---|---|---|---|---|---|---|
| (4-methyl-thieno[2,3-b]pyrrole) | IIa-71 | IIb-71 | IIc-71 | IId-71 | IIe-71 | IIf-71 |
| (1,5-dimethyl-thieno pyrrole) | IIa-72 | IIb-72 | IIc-72 | IId-72 | IIe-72 | IIf-72 |
| (1,5-dimethyl-thieno pyrrole) | IIa-73 | IIb-73 | IIc-73 | IId-73 | IIe-73 | IIf-73 |
| (methyl-thieno-thiophene) | IIa-74 | IIb-74 | IIc-74 | IId-74 | IIe-74 | IIf-74 |
| (methyl-thieno-thiophene) | IIa-75 | IIb-75 | IIc-75 | IId-75 | IIe-75 | IIf-75 |
| (6-methyl-indole) | IIa-76 | IIb-76 | IIc-76 | IId-76 | IIe-76 | IIf-76 |
| (5-methyl-indole) | IIa-77 | IIb-77 | IIc-77 | IId-77 | IIe-77 | IIf-77 |
| (1,5-dimethyl-indole) | IIa-78 | IIb-78 | IIc-78 | IId-78 | IIe-78 | IIf-78 |
| (3-methyl-6-methoxy-benzofuran) | IIa-79 | IIb-79 | IIc-79 | IId-79 | IIe-79 | IIf-79 |
| (3,7-dimethyl-5-methoxy-benzofuran) | IIa-80 | IIb-80 | IIc-80 | IId-80 | IIe-80 | IIf-80 |

TABLE 26
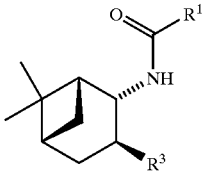
| R¹ | IIa | IIb | IIc | IId | IIe | IIf |
|---|---|---|---|---|---|---|
| 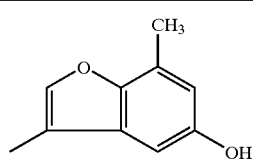 | IIa-81 | IIb-81 | IIc-81 | IId-81 | IIe-81 | IIf-81 |
| 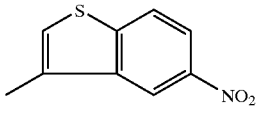 | IIa-82 | IIb-82 | IIc-82 | IId-82 | IIe-82 | IIf-82 |
| 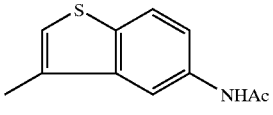 | IIa-83 | IIb-83 | IIc-83 | IId-83 | IIe-83 | IIf-83 |
| 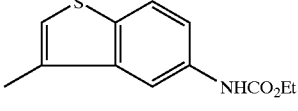 | IIa-84 | IIb-84 | IIc-84 | IId-84 | IIe-84 | IIf-84 |
| 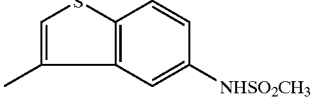 | IIa-85 | IIb-85 | IIc-85 | IId-85 | IIe-85 | IIf-85 |
| 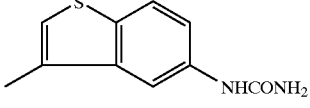 | IIa-86 | IIb-86 | IIc-86 | IId-86 | IIe-86 | IIf-86 |
| 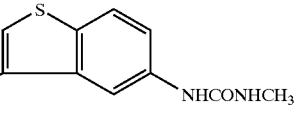 | IIa-87 | IIb-87 | IIc-87 | IId-87 | IIe-87 | IIf-87 |
| 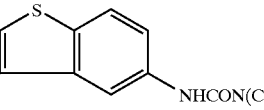 | IIa-88 | IIb-88 | IIc-88 | IId-88 | IIe-88 | IIf-88 |
| 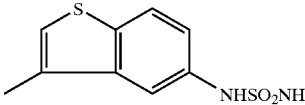 | IIa-89 | IIb-89 | IIc-89 | IId-89 | IIe-89 | IIf-89 |
| 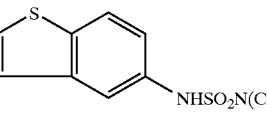 | IIa-90 | IIb-90 | IIc-90 | IId-90 | IIe-90 | IIf-90 |

TABLE 27

| R¹ | IIa | IIb | IIc | IId | IIe | IIf |
|---|---|---|---|---|---|---|
| 3-methylbenzothiophene-6-NHSO₂NH₂ | IIa-91 | IIb-91 | IIc-91 | IId-91 | IIe-91 | IIf-91 |
| 3-methylbenzothiophene-6-NHCO₂Et | IIa-92 | IIb-92 | IIc-92 | IId-92 | IIe-92 | IIf-92 |
| 3-methylbenzothiophene-6-NHCONH₂ | IIa-93 | IIb-93 | IIc-93 | IId-93 | IIe-93 | IIf-93 |
| 3-methylbenzothiophene-5-CH₂NHAc | IIa-94 | IIb-94 | IIc-94 | IId-94 | IIe-94 | IIf-94 |
| 3-methylbenzothiophene-5-CH₂NHCO₂Et | IIa-95 | IIb-95 | IIc-95 | IId-95 | IIe-95 | IIf-95 |
| 3-methylbenzothiophene-5-CH₂NHSO₂CH₃ | IIa-96 | IIb-96 | IIc-96 | IId-96 | IIe-96 | IIf-96 |
| 3-methylbenzothiophene-5-CH₂NHCONH₂ | IIa-97 | IIb-97 | IIc-97 | IId-97 | IIe-97 | IIf-97 |
| 3-methylbenzothiophene-5-CH₂CONH₂ | IIa-98 | IIb-98 | IIc-98 | IId-98 | IIe-98 | IIf-98 |
| 3-methylbenzothiophene-5-CONH₂ | IIa-99 | IIb-99 | IIc-99 | IId-99 | IIe-99 | IIf-99 |
| 3-methylbenzothiophene-5-CO₂H | IIa-100 | IIb-100 | IIc-100 | IId-100 | IIe-100 | IIf-100 |

TABLE 28

| R¹ | IIa | IIb | IIc | IId | IIe | IIf |
|---|---|---|---|---|---|---|
| 3-methylbenzothiophene-5-CONHOCH₃ | IIa-101 | IIb-101 | IIc-101 | IId-101 | IIe-101 | IIf-101 |
| 3-methylbenzothiophene-5-CONHSO₂CH₃ | IIa-102 | IIb-102 | IIc-102 | IId-102 | IIe-102 | IIf-102 |
| 3-methylbenzothiophene-6-CONH₂ | IIa-103 | IIb-103 | IIc-103 | IId-103 | IIe-103 | IIf-103 |
| 3-methylbenzothiophene-7-CONH₂ | IIa-104 | IIb-104 | IIc-104 | IId-104 | IIe-104 | IIf-104 |
| 7-methylbenzothiophene-3-CONH₂ | IIa-105 | IIb-105 | IIc-105 | IId-105 | IIe-105 | IIf-105 |
| 3-methylbenzothiophene-5-CONHCH₃ | IIa-106 | IIb-106 | IIc-106 | IId-106 | IIe-106 | IIf-106 |
| 3-methylbenzothiophene-5-CON(CH₃)₂ | IIa-107 | IIb-107 | IIc-107 | IId-107 | IIe-107 | IIf-107 |
| 3-methylbenzothiophene-5-CONHEt | IIa-108 | IIb-108 | IIc-108 | IId-108 | IIe-108 | IIf-108 |
| 3-methylbenzothiophene-5-SO₂NH₂ | IIa-109 | IIb-109 | IIc-109 | IId-109 | IIe-109 | IIf-109 |
| 3-methylbenzothiophene-6-SO₂NH₂ | IIa-110 | IIb-110 | IIc-110 | IId-110 | IIe-110 | IIf-110 |

TABLE 29

| R¹ | IIa | IIb | IIc | IId | IIe | IIf |
|---|---|---|---|---|---|---|
| (3,6-dimethylbenzothiophene-SO₂NH₂) | IIa-111 | IIb-111 | IIc-111 | IId-111 | IIe-111 | IIf-111 |
| (3-methyl-6-fluorobenzothiophene-SO₂NH₂) | IIa-112 | IIb-112 | IIc-112 | IId-112 | IIe-112 | IIf-112 |
| (7-methylbenzothiophene-3-SO₂NH₂) | IIa-113 | IIb-113 | IIc-113 | IId-113 | IIe-113 | IIf-113 |
| (7-methylbenzothiophene-3-SO₂N(CH₃)₂) | IIa-114 | IIb-114 | IIc-114 | IId-114 | IIe-114 | IIf-114 |
| (3,5,7-trimethylbenzothiophene) | IIa-115 | IIb-115 | IIc-115 | IId-115 | IIe-115 | IIf-115 |
| (methylenedioxy-methylbenzothiophene) | IIa-116 | IIb-116 | IIc-116 | IId-116 | IIe-116 | IIf-116 |
| (3,4,7-trimethylbenzothiophene) | IIa-117 | IIb-117 | IIc-117 | IId-117 | IIe-117 | IIf-117 |
| (dihydrofuran-fused methylbenzothiophene) | IIa-118 | IIb-118 | IIc-118 | IId-118 | IIe-118 | IIf-118 |
| (3-methyl-5,7-dichlorobenzothiophene) | IIa-119 | IIb-119 | IIc-119 | IId-119 | IIe-119 | IIf-119 |

TABLE 29-continued

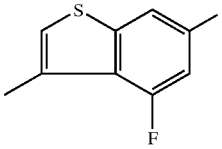

| R¹ | IIa | IIb | IIc | IId | IIe | IIf |
|---|---|---|---|---|---|---|
| (3-methyl-benzothiophene-6,4-diF) | IIa-120 | IIb-120 | IIc-120 | IId-120 | IIe-120 | IIf-120 |

TABLE 30

| R¹ | IIa | IIb | IIc | IId | IIe | IIf |
|---|---|---|---|---|---|---|
| (3-methyl-7,6-diCH₃-benzothiophene) | IIa-121 | IIb-121 | IIc-121 | IId-121 | IIe-121 | IIf-121 |
| (3-methyl-7-CH₃-6-F-benzothiophene) | IIa-122 | IIb-122 | IIc-122 | IId-122 | IIe-122 | IIf-122 |
| (3-methyl-5,6-diF-benzothiophene) | IIa-123 | IIb-123 | IIc-123 | IId-123 | IIe-123 | IIf-123 |
| (3-methyl-4,5-diF-benzothiophene) | IIa-124 | IIb-124 | IIc-124 | IId-124 | IIe-124 | IIf-124 |
| (3-methyl-4,5-diCH₃-benzothiophene) | IIa-125 | IIb-125 | IIc-125 | IId-125 | IIe-125 | IIf-125 |
| (3-methyl-6,7-diCH₃-benzothiophene) | IIa-126 | IIb-126 | IIc-126 | IId-126 | IIe-126 | IIf-126 |

TABLE 30-continued
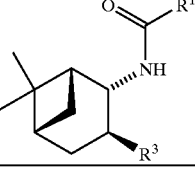
| R¹ | IIa | IIb | IIc | IId | IIe | IIf |
|---|---|---|---|---|---|---|
| 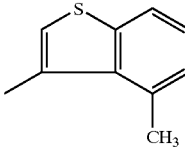 | IIa-127 | IIb-127 | IIc-127 | IId-127 | IIe-127 | IIf-127 |
| 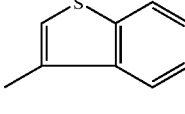 | IIa-128 | IIb-128 | IIc-128 | IId-128 | IIe-128 | IIf-128 |
| 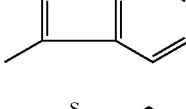 | IIa-129 | IIb-129 | IIc-129 | IId-129 | IIe-129 | IIf-129 |
| 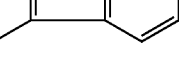 | IIa-130 | IIb-130 | IIc-130 | IId-130 | IIe-130 | IIf-130 |
TABLE 31
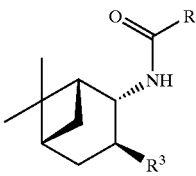
| R¹ | IIa | IIb | IIc | IId | IIe | IIf |
|---|---|---|---|---|---|---|
| 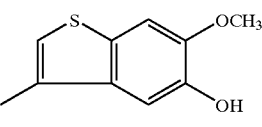 | IIa-131 | IIb-131 | IIc-131 | IId-131 | IIe-131 | IIf-131 |
| 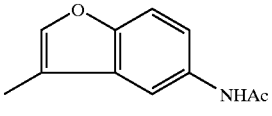 | IIa-132 | IIb-132 | IIc-132 | IId-132 | IIe-132 | IIf-132 |
| 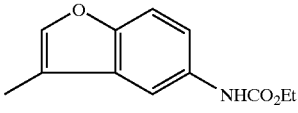 | IIa-133 | IIb-133 | IIc-133 | IId-133 | IIe-133 | IIf-133 |
| 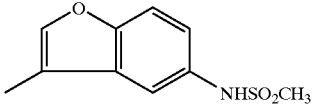 | IIa-134 | IIb-134 | IIc-134 | IId-134 | IIe-134 | IIf-134 |

TABLE 31-continued
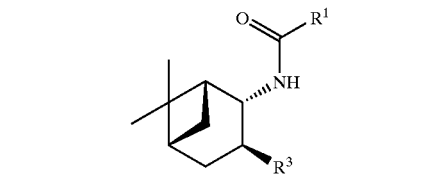
| R¹ | IIa | IIb | IIc | IId | IIe | IIf |
|---|---|---|---|---|---|---|
| 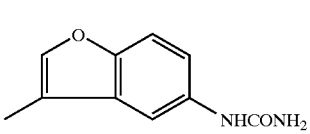 | IIa-135 | IIb-135 | IIc-135 | IId-135 | IIe-135 | IIf-135 |
| 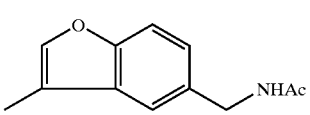 | IIa-136 | IIb-136 | IIc-136 | IId-136 | IIe-136 | IIf-136 |
| 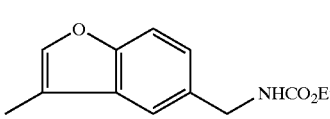 | IIa-137 | IIb-137 | IIc-137 | IId-137 | IIe-137 | IIf-137 |
| 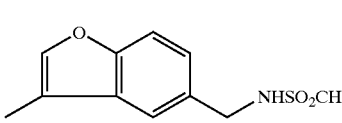 | IIa-138 | IIb-138 | IIc-138 | IId-138 | IIe-138 | IIf-138 |
| 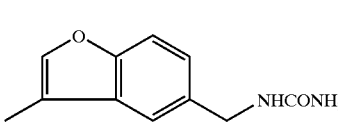 | IIa-139 | IIb-139 | IIc-139 | IId-139 | IIe-139 | IIf-139 |
| 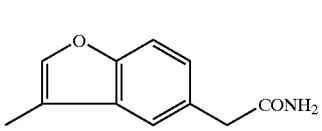 | IIa-140 | IIb-140 | IIc-140 | IId-140 | IIe-140 | IIf-140 |
TABLE 32
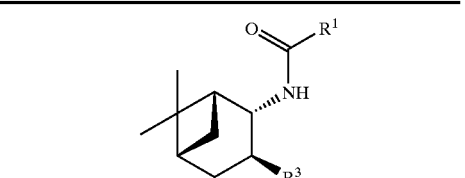
| R¹ | IIa | IIb | IIc | IId | IIe | IIf |
|---|---|---|---|---|---|---|
| 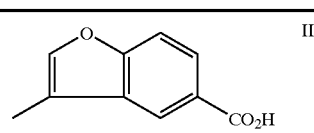 | IIa-141 | IIb-141 | IIc-141 | IId-141 | IIe-141 | IIf-141 |
| 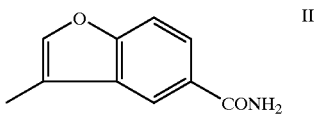 | IIa-142 | IIb-142 | IIc-142 | IId-142 | IIe-142 | IIf-142 |

TABLE 32-continued

| R¹ | IIa | IIb | IIc | IId | IIe | IIf |
|---|---|---|---|---|---|---|
| 3-methylbenzofuran-6-CONH₂ | IIa-143 | IIb-143 | IIc-143 | IId-143 | IIe-143 | IIf-143 |
| 3-methylbenzofuran-7-CONH₂ | IIa-144 | IIb-144 | IIc-144 | IId-144 | IIe-144 | IIf-144 |
| 3-methylbenzofuran-5-SO₂NH₂ | IIa-145 | IIb-145 | IIc-145 | IId-145 | IIe-145 | IIf-145 |
| 3-methylbenzofuran-6-SO₂NH₂ | IIa-146 | IIb-146 | IIc-146 | IId-146 | IIe-146 | IIf-146 |
| 5-methylbenzofuran | IIa-147 | IIb-147 | IIc-147 | IId-147 | IIe-147 | IIf-147 |
| 5-methylbenzofuran-3-CO₂H | IIa-148 | IIb-148 | IIc-148 | IId-148 | IIe-148 | IIf-148 |
| 5-methylbenzofuran-2-CO₂CH₃ | IIa-149 | IIb-149 | IIc-149 | IId-149 | IIe-149 | IIf-149 |
| 5-methylthiophene-2-CH₂-NHCO₂Et | IIa-150 | IIb-150 | IIc-150 | IId-150 | IIe-150 | IIf-150 |

TABLE 33

| R¹ | IIa | IIb | IIc | IId | IIe | IIf |
|---|---|---|---|---|---|---|
| 5-methylthiophene-2-CH₂-NHCONH₂ | IIa-151 | IIb-151 | IIc-151 | IId-151 | IIe-151 | IIf-151 |

TABLE 33-continued

| R¹ | IIa | IIb | IIc | IId | IIe | IIf |
|---|---|---|---|---|---|---|
| 5-methylthiophene-2-CH₂NHSO₂NH₂ | IIa-152 | IIb-152 | IIc-152 | IId-152 | IIe-152 | IIf-152 |
| 5-methylthiophene-2-CONH₂ | IIa-153 | IIb-153 | IIc-153 | IId-153 | IIe-153 | IIf-153 |
| 5-methylthiophene-2-SO₂NH₂ | IIa-154 | IIb-154 | IIc-154 | IId-154 | IIe-154 | IIf-154 |
| 4-methylthiophene-2-SO₂NH₂ | IIa-155 | IIb-155 | IIc-155 | IId-155 | IIe-155 | IIf-155 |
| 5-methylthiophene-2-CO₂H | IIa-156 | IIb-156 | IIc-156 | IId-156 | IIe-156 | IIf-156 |
| 5-methylthiophene-2-CH₂CONH₂ | IIa-157 | IIb-157 | IIc-157 | IId-157 | IIe-157 | IIf-157 |
| 3-methylbenzothiophene-5-CONHOH | IIa-158 | IIb-158 | IIc-158 | IId-158 | IIe-158 | IIf-158 |
| 3-methylbenzo[1,2-b:4,5-b']dithiophene | IIa-159 | IIb-159 | IIc-159 | IId-159 | IIe-159 | IIf-159 |
| 2-methylbenzo[1,2-b:4,5-b']dithiophene | IIa-160 | IIb-160 | IIc-160 | IId-160 | IIe-160 | IIf-160 |

TABLE 34

| R¹ | IIa | IIb | IIc | IId | IIe | IIf |
|---|---|---|---|---|---|---|
| 3-methylbenzo[1,2-b:3,4-b']dithiophene | IIa-161 | IIb-161 | IIc-161 | IId-161 | IIe-161 | IIf-161 |

TABLE 34-continued

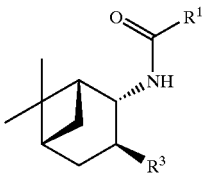

| R¹ | IIa | IIb | IIc | IId | IIe | IIf |
|---|---|---|---|---|---|---|
| 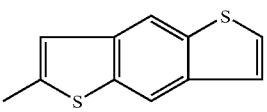 | IIa-162 | IIb-162 | IIc-162 | IId-162 | IIe-162 | IIf-162 |
| 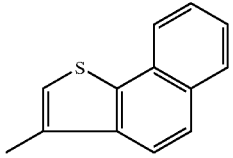 | IIa-163 | IIb-163 | IIc-163 | IId-163 | IIe-163 | IIf-163 |
| 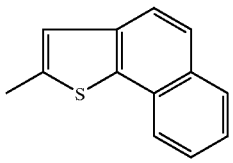 | IIa-164 | IIb-164 | IIc-164 | IId-164 | IIe-164 | IIf-164 |
| 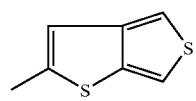 | IIa-165 | IIb-165 | IIc-165 | IId-165 | IIe-165 | IIf-165 |
| 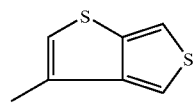 | IIa-166 | IIb-166 | IIc-166 | IId-166 | IIe-166 | IIf-166 |

TABLE 35

| Compound No. | Physical property |
|---|---|
| Ia-04 | mp 175–178° C.; ¹H-NMR (CDCl₃—CD₃OD) δ 1.04 (1H, m), 1.25–1.49 (10H, m), 1.57–1.66 (2H, m), 2.00 (1H, m), 2.15–2.22 (2H, m), 2.51 (1H, m), 3.82 (1H, m), 5.77 (1H, dt, J = 15.9, 1.5 Hz), 6.41 (1H, d, J = 7.8 Hz), 6.95 (1H, dt, J = 15.9, 7.1 Hz), 7.34 (1H, dd, J = 3.0, 4.8 Hz), 7.41 (1H, dd, J = 1.5, 4.8 Hz), 7.90 (1H, dd, J = 1.5, 3.0 Hz); IR (Nujol) 3363, 3105, 2627, 1697, 1618, 1554, 1248 cm⁻¹; $[\alpha]_D^{25}$ + 44.3 ± 0.8° (c = 1.011, MeOH); Anal. (C₁₉H₂₅NO₃S) Calcd. (%): C, 65.68; H, 7.25; N, 4.03; S, 9.23 Found (%): C, 65.58; H, 7.18; N, 4.03; S, 9.18 |
| Ia-17 | mp 155–157° C.; ¹H-NMR (CDCl₃—CD₃OD) δ 1.04 (1H, m), 1.22–1.53 (10H, m), 1.60–1.71 (2H, m), 2.02 (1H, m), 2.17–2.23 (2H, m), 2.58 (1H, m), 3.92 (1H, m), 5.78 (1H, dt, J = 15.6, 1.5 Hz), 6.33 (1H, d, J = 7.5 Hz), 6.97 (1H, dt, J = 15.6, 6.9 Hz), 7.38–7.49 (2H, m), 7.86–7.89 (3H, m), 8.30 (1H, dd, J = 0.9, 6.9 Hz); IR (Nujol) 3276, 2671, 1693, 1622, 1529, 1421, 1377, 1298, 1277, 1254 cm⁻¹; $[\alpha]_D^{25}$ + 38.5 ± 0.8° (c = 1.018, MeOH); Anal. (C₂₃H₂₇NO₃S.0.2H₂O) Calcd. (%): C, 68.87; H, 6.88; N, 3.49; S, 7.99 Found (%): C, 68.93; H, 7.01; N, 3.55; S, 7.87 |

TABLE 35-continued

| Compound No. | Physical property |
| --- | --- |
| Ia-20 | mp 129–131° C.; $^1$H-NMR (CDCl$_3$) δ 1.01 (1H, m), 1.26–1.52 (10H, m), 1.60–1.66 (2H, m), 2.02 (1H, m), 2.18–2.25 (2H, m), 2.49 (3H, s), 2.58 (1H, m), 3.95 (1H, m), 5.80 (1H, d, J = 15.6 Hz), 6.06 (1H, d, J = 7.8 Hz), 7.04 (1H, dt, J = 15.6, 7.1 Hz), 7.23 (1H, dd, J = 1.2, 8.4 Hz), 7.74 (1H, d, J = 8.4 Hz), 7.80 (1H, s), 8.14 (1H, s); IR (Nujol) 3269, 3078, 2677, 1697, 1649, 1624, 1539, 1437, 1377, 1298, 1281 cm$^{-1}$; $[α]_D^{25}$ + 32.0 ± 0.7° (c = 1.005, MeOH); Anal. (C$_{24}$H$_{29}$NO$_3$S) Calcd. (%): C, 70.04; H, 7.10; N, 3.40; S, 7.79 Found (%): C, 69.83; H, 7.10; N, 3.43; S, 7.64 |
| Ia-28 | mp 138–140° C.; $^1$H-NMR (CDCl$_3$) δ 1.02 (1H, m), 1.21–1.52 (10H, m), 1.59–1.70 (2H, m), 2.01 (1H, m), 2.17–2.24 (2H, m), 2.56 (1H, m), 3.92 (1H, m), 5.79 (1H, dt, J = 15.6, 1.5 Hz), 6.14 (1H, d, J = 8.1 Hz), 7.03 (1H, dt, J = 15.6, 7.1 Hz), 7.16 (1H, td, J = 8.6, 2.7 Hz), 7.77 (1H, dd, J = 4.8, 8.6 Hz), 7.91 (1H, s), 8.07 (1H, dd, J = 2.7, 10.2 Hz); IR (Nujol) 3276, 2671, 1695, 1624, 1533, 1442, 1433, 1296, 1277, 1246, 1200 cm$^{-1}$; $[α]_D^{25}$ + 35.6 ± 0.8° (c = 1.014, MeOH); Anal. (C$_{23}$H$_{26}$FNO$_3$S.0.2H$_2$O) Calcd. (%): C, 65.91; H, 6.35; F, 4.53; N, 3.34; S, 7.65 Found (%): C, 65.99; H, 6.38; F, 4.42; N, 3.39; S, 7.57 |
| Ia-34 | mp 172–173° C.; $^1$H-NMR (CDCl$_3$—CD$_3$OD) δ 1.08 (1H, m), 1.29–1.55 (10H, m), 1.60–1.69 (2H, m), 2.03 (1H, m), 2.14–2.21 (2H, m), 2.60 (1H, m), 3.96 (1H, m), 5.76 (1H, dt, J = 15.6, 1.5 Hz), 6.57 (1H, d, J = 7.5 Hz), 6.97 (1H, dt, J = 15.6, 7.1 Hz), 7.38 (1H, d, J = 5.7 Hz), 7.42 (1H, t, J = 7.8 Hz), 7.59 (1H, d, J = 5.7 Hz), 7.65 (1H, d, J = 6.9 Hz), 7.95 (1H, d, J = 7.8 Hz); IR (Nujol) 3302, 2698, 1739, 1693, 1657, 1622, 1581, 1568, 1547, 1205 cm$^{-1}$; $[α]_D^{25}$ + 35.0 ± 0.7° (c = 1.013, MeOH); Anal. (C$_{23}$H$_{27}$NO$_3$S.0.2H$_2$O) Calcd. (%): C, 68.87; H, 6.88; N, 3.49; S, 7.99 Found (%): C, 68.92; H, 7.05; N, 3.44; S, 7.67 |

TABLE 36

| Compound No. | Physical property |
| --- | --- |
| Ia-49 | $^1$H-NMR (CDCl$_3$) δ 1.02 (1H, m), 1.29–1.74 (12H, m), 2.02 (1H, m), 2.17–2.24 (2H, m), 2.56 (1H, m), 3.44 (3H, s), 3.96 (1H, m), 4.79 (2H, s), 5.79 (1H, dt, J = 15.6, 1.2 Hz), 5.98 (1H, d, J = 7.8 Hz), 7.01 (1H, dt, J = 15.6, 7.2 Hz), 7.33–7.40 (2H, m), 7.77 (1H, dd, J = 7.2, 2.4 Hz), 8.14 (1H, s); IR (CHCl$_3$) 3442, 2682, 1695, 1652, 1573, 1508, 1425, 1284, 1205, 1120 cm$^{-1}$; $[α]_D^{25.0}$ + 31.0 ± 0.7° (c = 1.009, MeOH); Anal. (C$_{25}$H$_{31}$NO$_5$.0.5H$_2$O) Calcd. (%): C, 69.10; H, 7.42; N, 3.22 Found (%): C, 68.83; H, 7.48; N, 3.30 |
| Ia-51 | $^1$H-NMR (CDCl$_3$—CD$_3$OD) δ 1.03 (1H, m), 1.20–1.51 (9H, m), 1.59–1.71 (3H, m), 2.01 (1H, d, J = 3.6 Hz), 2.15–2.22 (2H, m), 2.56 (1H, s), 3.90 (1H, m), 5.77 (1H, d, J = 15.6 Hz), 6.90 (1H, dd, J = 2.1, 8.4 Hz), 6.96 (1H, dt, J = 15.6, 6.9 Hz), 6.99 (1H, d, J = 2.1 Hz), 7.58 (1H, d, J = 8.4 Hz), 8.01 (1H, s); IR (KBr) 3350, 3141, 1695, 1628, 1560, 1523, 1493, 1441, 1367, 1279, 1225, 1136, 1124 cm$^{-1}$; $[α]_D^{27}$ + 26.6 ± 0.7° (c = 1.008, MeOH); Anal. (C$_{23}$H$_{27}$NO$_5$.0.3H$_2$O) Calcd. (%): C, 68.57; H, 6.91; N, 3.48 Found (%): C, 68.47; H, 6.91; N, 3.66 |
| Ia-52 | $^1$H-NMR (CDCl$_3$—CD$_3$OD) δ 1.02 (1H, m), 1.22–1.48 (9H, m), 1.57–1.60 (3H, m), 1.98 (1H, d, J = 3.3 Hz), 2.11–2.18 (2H, m), 2.53 (1H, s), 3.89 (1H, m), 5.75 (1H, dd, J = 1.5, 15.3 Hz), 6.31 (1H, d, J = 7.8 Hz), 6.90 (1H, dd, J = 2.4, 8.7 Hz), 6.96 (1H, dt, J = 15.3, 6.9 Hz), 7.33 (1H, d, J = 8.7 Hz), 7.43 (1H, d, J = 2.4 Hz), 8.07 (1H, s); IR (KBr) 3347, 1695, 1635, 1558, 1524, 1462, 1309, 1271, 1192, 1173, 1134 cm$^{-1}$; $[α]_D^{25}$ + 20.1 ± 0.6° (c = 1.013, MeOH); Anal. (C$_{23}$H$_{27}$NO$_5$.0.4H$_2$O) Calcd. (%): C, 68.27; H, 6.92; N, 3.46 Found (%): C, 68.12; H, 7.00; N, 3.59 |
| Ia-54 | $^1$H-NMR (CDCl$_3$) δ 1.05 (1H, m), 1.23–1.72 (10H, m), 2.02 (1H, m), 2.18–2.25 (2H, m), 2.55 (1H, m), 3.94 (1H, m), 5.79 (1H, dt, J = 15.6, 1.5 Hz), 5.91 (1H, d, J = 8.1 Hz), 7.03 (1H, dt, J = 15.6, 6.9 Hz), 7.09–7.16 (1H, m), 7.25 (1H, dd, J = 9.0, 1.8 Hz), 7.84 (1H, dd, J = 9.0, 5.4 Hz), 8.06 (1H, s); IR (CHCl$_3$) 3442, 2680, 1695, 1652, 1563, 1506, 1257, 1224, 1218, 1133, cm$^{-1}$; $[α]_D^{25.0}$ + 25.4 ± 0.7° (c = 1.005, MeOH); Anal. (C$_{23}$H$_{28}$FNO$_4$.0.1H$_2$O) Calcd. (%): C, 68.85; H, 6.58; F, 4.73; N, 3.49 Found (%): C, 68.65; H, 6.43; F, 4.59; N, 3.60 |

TABLE 36-continued

| Compound No. | Physical property |
| --- | --- |
| Ia-56 | $^1$H-NMR (CDCl$_3$) δ 1.12 (1H, m), 1.29–1.53 (9H, m), 1.60–1.74 (3H, m), 2.04 (1H, d, J = 3.6 Hz), 2.16–2.22 (2H, m), 2.57 (1H, s), 4.03 (1H, m), 5.77 (1H, d, J = 15.6 Hz), 6.89 (1H, d, J = 2.1 Hz), 7.02 (1H, dt, J = 15.3, 7.2 Hz), 7.36 (1H, t, J = 7.5 Hz), 7.57 (1H, d, J = 7.8 Hz), 7.74 (1H, dd, J = 1.2, 7.5 Hz), 7.74 (1H, d, J = 2.1 Hz), 8.11 (1H, dd, J = 1.2, 7.5 Hz); IR (CHCl$_3$) 3435, 2679, 1695, 1653, 1595, 1547, 1533, 1475, 1458, 1421, 1306, 1286, 1167, 1120 cm$^{-1}$; [α]$_D^{25.5}$ + 47.7 ± 0.9° (c = 1.003, MeOH); Anal. (C$_{23}$H$_{27}$NO$_4$0.1H$_2$O) Calcd. (%): C, 72.08; H, 7.15; N, 3.65 Found (%): C, 72.01; H, 7.11; N, 3.72 |

TABLE 37

| Compound No. | Physical property |
| --- | --- |
| Ia-65 | $^1$H-NMR (CDCl$_3$) δ 1.02 (1H, m), 1.27–1.71 (12H, m), 2.01 (1H, d, J = 3.9 Hz), 2.16–2.23 (2H, m), 2.48 (1H, br s), 3.92 (1H, m), 5.81 (1H, d, J = 15.6 Hz), 6.08 (1H, d, J = 8.4 Hz), 6.80 (1H, d, J = 1.5 Hz), 6.98 (1H, dt, J = 5.4 and 0.6 Hz), 7.03 (1H, dt, J = 15.6 and 6.9 Hz), 10.49 (1H, s); IR (CHCl$_3$) 3446, 3215, 1726, 1693, 1643, 1541, 1504, 1477, 1462, 1402, 1373, 1303, 1248 cm$^{-1}$; [α]$_D^{26}$ + 67.8 ± 1.1° (c = 1.002, MeOH) Anal. (C$_{21}$H$_{26}$N$_2$O$_3$S.0.25CH$_3$COOEt) Calcd. (%): C, 63.43; H, 6.77; N, 6.72; S, 7.69 Found (%): C, 63.66; H, 6.60; N, 6.93; S, 7.60 |
| Ia-66 | $^1$H-NMR (CDCl$_3$) δ 1.02 (1H, m), 1.27–1.70 (12H, m), 2.01 (1H, d, J = 3.6 Hz), 2.15–2.22 (2H, m), 2.51 (1H, br s), 3.92 (1H, m), 5.80 (1H, d, J = 15.6 Hz), 6.08 (1H, d, J = 7.8 Hz), 6.77 (1H, d, J = 2.1 Hz), 6.88 (1H, d, J = 5.4 Hz), 6.95 (1H, d, J = 5.4 Hz), 7.03 (1H, dt, J = 15.6 and 6.9 Hz), 11.07 (1H, s); IR (CHCl$_3$) 3444, 3191, 2677, 1693, 1639, 1543, 1518, 1475, 1458, 1421, 1396, 1378, 1296, 1279, 1255 cm$^{-1}$; [α]$_D^{26}$ + 55.3 ± 1.0° (c = 1.001, MeOH) Anal. (C$_{21}$H$_{26}$N$_2$O$_3$S.0.3H$_2$O) Calcd. (%): C, 64.36; H, 6.84; N, 7.15; S, 8.18 Found (%): C, 64.22; H, 6.48; N, 7.13; S, 8.22 |
| Ia-95 | mp 113–114° C.; $^1$H-NMR (CDCl$_3$—DMSO—d$_6$) δ 1.12 (1H, m), 1.26 (3H, t, J = 6.9 Hz), 1.27–1.64 (12H, m), 2.01 (1H, m), 2.15–2.22 (2H, m), 2.57 (1H, br s), 3.90 (1H, m), 4.14 (2H, q, J = 6.9 Hz), 4.48 (2H, br s), 5.57 (1H, br s), 5.77 (1H, d, J = 15.6 Hz), 6.68 (1H, br s), 6.92 (1H, dd, J = 15.6, 7.2 Hz), 7.38 (1H, br d, J = 8.1 Hz), 7.81 (1H, d, J = 8.1 Hz), 7.95 (1H, s), 8.33 (1H, br s); IR (CHCl$_3$) 3446, 1703, 1653, 1514, 1435, 1300, 1223, 1134 cm$^{-1}$; [α]$_D^{23}$ + 5.5 ± 0.5° (c = 1.008, MeOH). Anal. (C$_{27}$H$_{34}$N$_2$O$_5$S.0.3H$_2$O) Calcd. (%): C, 64.34; H, 6.92; N, 5.56; S, 6.36 Found (%): C, 64.27; H, 6.69; N, 5.54; S, 6.37 |
| Ic-04 | mp 105–107° C.; $^1$H-NMR (CDCl$_3$) δ 1.02 (1H, m), 1.20–1.70 (12H, m), 2.00 (1H, m), 2.49 (1H, br s), 3.47–3.58 (2H, m), 3.91 (1H, m), 4.04 (2H, s), 6.07 (1H, d, J = 7.2 Hz), 7.34 (1H, dd, J = 3.0, 5.1 Hz), 7.37 (1H, dd, J = 1.5, 5.1 Hz), 7.88 (1H, dd, J = 1.5, 3.0 Hz); IR (Nujol) 3354, 3093, 2553, 1730, 1612, 1556, 1240, 1138 cm$^{-1}$; [α]$_D^{25}$ + 46.6 ± 0.9° (c = 1.009, MeOH); Anal. (C$_{18}$H$_{25}$NO$_4$S) Calcd. (%): C, 61.51; H, 7.17; N, 3.99; S, 9.12 Found (%): C, 61.45; H, 7.32; N, 4.06; S, 9.10 |
| Ic-17 | mp 149–151° C.; $^1$H-NMR (CDCl$_3$) δ 1.05 (1H, m), 1.21–1.72 (12H, m), 2.02 (1H, m), 2.57 (1H, br s), 3.47–3.58 (2H, m), 3.98 (1H, m), 4.03 (2H, s), 6.14 (1H, d, J = 7.8 Hz), 7.40 (1H, d, J = 7.8 Hz), 7.44 (1H, dt, J = 1.2, 7.5 Hz), 7.46 (1H, dt, J = 1.2, 7.5 Hz), 7.87 (1H, dd, J = 1.2, 7.5 Hz), 7.88 (1H, s), 8.29 (1H, dd, J = 1.2, 7.5 Hz); IR (Nujol) 3296, 2528, 1726, 1604, 1558, 1240, 1228, 1140 cm$^{-1}$; [α]$_D^{25}$ + 38.1 ± 0.8° (c = 1.013, MeOH); Anal. (C$_{22}$H$_{27}$NO$_4$S) Calcd. (%): C, 65.18; H, 6.78; N, 3.49; S, 7.99 Found (%): C, 65.62; H, 7.06; N, 3.51; S, 7.78 |

TABLE 38

| Compound No. | Physical property |
| --- | --- |
| Ic-19 | mp 145–147° C.; $^1$H-NMR (CDCl$_3$) δ 1.05 (1H, m), 1.21–1.33 (2H, m), 1.40–1.71 (10H, m), 2.01 (1H, m), 2.48 (3H, s), 2.6 (1H, br s), 3.47–3.58 (2H, m), 3.97 (1H, m), 4.03 (2H, s), 6.12 (1H, d, J = 7.8 Hz), 7.28 (1H, m), 7.65 (1H, m), 7.78 (1H, s), 8.15 (1H, d, J = 8.4 Hz); IR (Nujol) 3288, 2521, 1724, 1601, 1560, 1225, 1138 cm$^{-1}$; [α]$_D^{25}$ + 36.8 ± 0.8° (c = 1.008, MeOH) Anal. (C$_{23}$H$_{29}$NO$_4$S) Calcd. (%): C, 66.48; H, 7.03; N, 3.37; S, 7.72 Found (%): C, 66.33; H, 7.03; N, 3.30; S, 7.43 |

TABLE 38-continued

| Compound No. | Physical property |
| --- | --- |
| Ic-20 | mp 135–136° C.; $^1$H-NMR (CDCl$_3$) δ 1.05 (1H, m), 1.21–1.72 (12H, m), 2.02 (1H, m), 2.49 (3H, s), 2.57 (1H, br s), 3.48–3.59 (2H, m), 3.97 (1H, m), 4.03 (2H, s), 6.12 (1H, d, J = 7.5 Hz), 7.23 (1H, dd, J = 1.5, 8.4 Hz), 7.74 (1H, d, J = 8.4 Hz), 7.83 (1H, s), 8.12 (1H, d, J = 1.5 Hz); IR (Nujol) 3384, 3361, 2546, 1736, 1718, 1616, 1533, 1225, 1140 cm$^{-1}$; $[α]_D^{25}$ + 32.4 ± 0.7° (c = 1.003, MeOH); Anal. (C$_{23}$H$_{29}$NO$_4$S) Calcd. (%): C, 66.48; H, 7.03; N, 3.37; S, 7.72 Found (%): C, 66.31; H, 7.32; N, 3.34; S, 7.60 |
| Ic-22 | mp 76–79° C.; $^1$H-NMR (CDCl$_3$—CD$_3$OD) δ 1.07 (1H, m), 1.20–1.32 (2H, m), 1.34–1.70 (10H, m), 2.00 (1H, m), 2.57 (1H, br s), 3.44–3.55 (2H, m), 3.88 (1H, m), 4.00 (2H, s), 6.43 (1H, d, J = 7.8 Hz), 6.97 (1H, dd, J = 2.4 and 8.7 Hz), 7.25 (1H, d, J = 2.4 Hz), 7.65 (1H, s), 8.06 (1H, d, J = 8.7 Hz); IR (CHCl$_3$) 3599, 3437, 1780, 1649, 1603, 1516, 1124 cm$^{-1}$; $[α]_D^{25}$ + 36.4 ± 0.8° (c = 1.013, MeOH) Anal. (C$_{22}$H$_{27}$NO$_5$S.0.6H$_2$O) Calcd. (%): C, 61.69; H, 6.64; N, 3.27; S, 7.49 Found (%): C, 61.58; H, 6.37; N, 3.54; S, 7.48 |
| Ic-23 | mp 149–151° C.; $^1$H-NMR (CDCl$_3$) δ 1.08 (1H, m), 1.21–1.86 (12H, m), 1.99 (1H, m), 2.22 (1H, br s), 2.56 (1H, m), 3.53 (2H, t, J = 6.0 Hz), 3.92 (1H, m), 4.03 (2H, s), 6.31 (1H, d, J = 7.2 Hz), 7.00 (1H, dd, J = 2.1, 8.7 Hz), 7.67 (1H, d, J = 8.7 Hz), 7.72 (1H, d, J = 2.4 Hz), 7.83 (1H, s); IR (Nujol) 3313, 3104, 2636, 1743, 1626, 1599, 1552, 1439, 1248, 1190, 1153, 1124 cm$^{-1}$; $[α]_D^{26}$ + 33.6 ± 0.7° (c = 1.002%, MeOH); Anal. (C$_{22}$H$_{27}$NO$_5$S) Calcd. (%): C, 63.29; H, 6.52; N, 3.35; S, 7.68 Found (%): C, 62.99; H, 6.66; N, 3.39; S, 7.57 |
| Ic-28 | mp 149–151° C.; $^1$H-NMR (CDCl$_3$) δ 1.05 (1H, m), 1.21–1.72 (12H, m), 2.03 (1H, m), 2.56 (1H, br s), 3.48–3.60 (2H, m), 3.95 (1H, m), 4.04 (2H, s), 6.11 (1H, d, J = 8.1 Hz), 7.16 (1H, dt, J = 2.4, 8.7 Hz), 7.78 (1H, dd, J = 4.8, 8.7 Hz), 7.92 (1H, s), 8.05 (1H, dd, J = 2.4, 9.9 Hz); IR (Nujol) 3384, 3361, 2546, 1736, 1718, 1616, 1533, 1225, 1140 cm$^{-1}$; $[α]_D^{25}$ + 35.6 ± 0.8° (c = 1.014, MeOH); Anal. (C$_{22}$H$_{26}$FNO$_4$S) Calcd. (%): C, 62.99; H, 6.25; F, 4.53; N, 3.34; S, 7.64 Found (%): C, 62.84; H, 6.51; F, 4.44; N, 3.41; S, 7.40 |
| Ic-34 | mp 154–157° C.; $^1$H-NMR (CDCl$_3$) δ 1.09 (1H, m), 1.24–1.72 (12H, m), 2.04 (1H, m), 2.59 (1H, br s), 3.47–3.58 (2H, m), 4.02 (1H, m), 4.02 (2H, s), 6.42 (1H, d, J = 7.5 Hz), 7.38 (1H, d, J = 5.4 Hz), 7.43 (1H, d, J = 7.5 Hz), 7.59 (1H, d, J = 5.4 Hz), 7.61 (1H, d, J = 7.5 Hz), 7.96 (1H, dd, J = 0.9, 7.5 Hz); IR (Nujol) 3288, 2540, 1726, 1614, 1577, 1554, 1319, 1244, 1225, 1138 cm$^{-1}$; $[α]_D^{25}$ + 39.8 ± 0.8° (c = 1.017, MeOH); Anal. (C$_{22}$H$_{27}$NO$_4$S) Calcd. (%): C, 65.81; H, 6.78; N, 3.49; S, 7.99 Found % C, 65.53; H, 6.94; N, 3.52; S, 7.76 |

TABLE 39

| Compound No. | Physical property |
| --- | --- |
| Ic-39 | $^1$H-NMR (CDCl$_3$) δ 1.10 (1H, m), 1.25–1.71 (12H, m), 2.03 (1H, m), 2.58 (1H, br s), 3.49–3.56 (2H, m), 3.98 (3H, s), 4.02 (2H, s), 4.03 (1H, m), 6.40 (1H, d, J = 8.4 Hz), 6.42 (2H, s), 7.42 (1H, t, J = 7.5 Hz), 7.66 (1H, d, J = 7.5 Hz), 7.93 (1H, d, J = 7.5 Hz); IR (CHCl$_3$) 3451, 1780, 1732, 1649, 1508, 1373, 1220, 1151 cm$^{-1}$; $[α]_D^{24}$ + 37.0 ± 0.8° (c = 1.008, MeOH); Anal. (C$_{23}$H$_{29}$NO$_5$S.0.3H$_2$O) Calcd. (%): C, 63.22; H, 6.83; N, 3.21; S, 7.34 Found (%): C, 63.26; H, 6.78; N, 3.23; S, 7.17 |
| Ic-49 | $^1$H-NMR (CDCl$_3$) δ 1.06 (1H, m), 1.29–1.36 (2H, m), 1.36–1.74 (10H, m), 2.03 (1H, m), 2.53 (1H, m), 3.45 (3H, s), 3.52 (2H, dt, J = 6.3, 1.5 Hz), 4.00 (1H, m), 4.02 (2H, s), 4.79 (2H, s), 6.07 (1H, d, J = 7.8 Hz), 7.33–7.40 (2H, m), 7.77 (1H, dd, J = 6.9, 2.1 Hz), 8.16 (1H, s); IR (CHCl$_3$) 3440, 2829, 1652, 1573, 1509, 1226, 1205, 1124 cm$^{-1}$; $[α]_D^{25.0}$ + 33.3 ± 0.7° (c = 1.016, MeOH); Anal. (C$_{24}$H$_{31}$NO$_6$) Calcd. (%): C, 67.11; H, 7.27; N, 3.26 Found (%): C, 66.82; H, 7.39; N, 3.32 |
| Ic-51 | $^1$H-NMR (CDCl$_3$—CD$_3$OD) δ 1.08 (1H, m), 1.25–1.28 (2H, m), 1.37–1.62 (10H, m), 1.99 (1H, d, J = 3.3 Hz), 2.54 (1H, s), 3.45–3.49 (2H, m), 3.87 (1H, m), 4.00 (2H, s), 6.44 (1H, d, J = 7.8 Hz), 6.88 (1H, dd, J = 2.1, 8.7 Hz), 6.97 (1H, d, J = 2.1 Hz), 7.60 (1H, d, J = 8.7 Hz), 8.02 (1H, s); IR (KBr) 3365, 3140, 1734, 1628, 1560, 1527, 1493, 1440, 1363, 1279, 1220, 1136, 1124 cm$^{-1}$; $[α]_D^{27}$ + 29.1 ± 0.7° (c = 1.016, MeOH); Anal. (C$_{22}$H$_{27}$NO$_6$.0.5H$_2$O) Calcd. (%): C, 64.38; H, 6.88; N, 3.41 Found (%): C, 64.39; H, 6.95; N, 3.66 |

TABLE 39-continued

| Compound No. | Physical property |
| --- | --- |
| Ic-52 | $^1$H-NMR (CDCl$_3$—CD$_3$OD) δ 1.07 (1H, m), 1.24–1.30 (3H, m), 1.45–1.49 (5H, m), 1.59–1.65 (4H, m), 2.00 (1H, d, J = 3.3 Hz), 2.59 (1H, s), 3.52 (2H, t, J = 6.0 Hz), 3.89 (1H, m), 4.00 (1H, d, J = 16.5 Hz), 4.06 (1H, d, J = 16.5 Hz), 6.14 (1H, d, J = 8.1 Hz), 6.90 (1H, dd, J = 2.1, 9.0 Hz), 7.34 (1H, d, J = 2.1 Hz), 7.36 (1H, d, J = 9.0 Hz), 8.06 (1H, s); IR (CHCl$_3$) 3438, 3267, 1730, 1647, 1620, 1558, 1514, 1468, 1169, 1134 cm$^{-1}$; $[\alpha]_D^{27}$ + 25.0 ± 0.7° (c = 1.003, MeOH); Anal. (C$_{22}$H$_{27}$NO$_6$·0.3H$_2$O) Calcd. (%): C, 64.95; H, 6.84; N, 3.44 Found (%): C, 64.84; H, 6.96; N, 3.62 |
| Ic-54 | $^1$H-NMR (CDCl$_3$) δ 1.04 (1H, m), 1.25–1.32 (2H, m), 1.43–1.68 (10H, m), 2.03 (1H, m), 2.53 (1H, m), 3.53 (2H, t, J = 6.6 Hz), 3.96 (1H, m), 4.04 (2H, s), 6.04 (1H, d, J = 8.1 Hz), 7.09–7.16 (1H, m), 7.25 (1H, dd, J = 8.4, 2.4 Hz), 7.84 (1H, dd, J = 8.4, 5.7 Hz), 8.10 (1H, s); IR (CHCl$_3$) 3440, 2875, 1656, 1563, 1506, 1224, 1216, 1205 cm$^{-1}$; $[\alpha]_D^{26.0}$ + 27.6 ± 0.7° (c = 1.018, MeOH); Anal. (C$_{22}$H$_{26}$FNO$_5$·0.6H$_2$O) Calcd. (%): C, 63.79; H, 6.62; F, 4.59; N, 3.38 Found (%): C, 63.48; H, 6.49; F, 4.47; N, 3.59 |
| Ic-65 | mp 148–149° C.; $^1$H-NMR (CDCl$_3$) δ 1.05 (1H, m), 1.27–1.30 (2H, m), 1.41–1.52 (6H, m), 1.59–1.71 (4H, m), 2.01 (1H, d, J = 3.3 Hz), 2.45 (1H, s), 3.53 (2H, dt, J = 1.5, 6.3 Hz), 3.94 (1H, m), 4.07 (2H, s), 6.13 (1H, d, J = 8.1 Hz), 6.78 (1H, d, J = 1.5 Hz), 6.98 (1H, d, J = 5.1 Hz), 7.23 (1H, d, J = 8.1 Hz), 10.27 (1H, s); IR (KBr) 3367, 3292, 3111, 2758, 2636, 2544, 1712, 1601, 1574, 1510, 1458, 1325, 1250, 1225, 1138 cm$^{-1}$; $[\alpha]_D^{25}$ + 66.6 ± 1.1° (c = 1.008, MeOH); Anal. (C$_{20}$H$_{26}$N$_2$O$_4$S·0.1H$_2$O) Calcd. (%): C, 61.23; H, 6.68; N, 7.14; S, 8.17 Found (%): C, 61.20; H, 6.79; N, 7.25; S, 8.25 |

TABLE 40

| Compound No. | Physical property |
| --- | --- |
| Ic-66 | mp 143–144° C.; $^1$H-NMR (CDCl$_3$) δ 1.05 (1H, m), 1.24–1.30 (2H, m), 1.38–1.52 (6H, m), 1.59–1.67 (4H, m), 2.01 (1H, d, J = 3.0 Hz), 2.48 (1H, s), 3.52 (2H, t, J = 6.3 Hz), 3.94 (1H, m), 4.07 (2H, s), 6.12 (1H, d, J = 8.4 Hz), 6.73 (1H, d, J = 1.8 Hz), 6.88 (1H, d, J = 5.4 Hz), 6.93 (1H, d, J = 5.4 Hz), 10.80 (1H, s); IR (KBr) 3348, 3105, 2754, 2648, 2551, 1738, 1587, 1556, 1520, 1437, 1425, 1223, 1146 cm$^{-1}$; $[\alpha]_D^{25}$ + 50.5 ± 0.9° (c = 1.014, MeOH); Anal. (C$_{20}$H$_{26}$N$_2$O$_4$S·0.1H$_2$O) Calcd. (%): C, 61.23; H, 6.68; N, 7.14; S, 8.17 Found (%): C, 61.13; H, 6.79; N, 7.17; S, 8.07 |
| Ic-81 | $^1$H-NMR (CDCl$_3$—CD$_3$OD) δ 1.06 (1H, m), 1.20–1.28 (2H, m), 1.34–1.49 (6H, m), 1.55–1.63 (4H, m), 1.95 (1H, d, J = 3.6 Hz), 2.42 (3H, s), 2.56 (1H, brs), 3.48 (2H, t, J = 6.5 Hz), 3.84 (1H, br s), 4.01 (2H, s), 6.37 (1H, d, J = 7.5 Hz), 6.71 (1H, d, J = 2.1 Hz), 7.16 (1H, d, J = 2.1 Hz), 8.10 (1H, s); IR (KBr) 3361, 3134, 1734, 1635, 1560, 1529, 1458, 1415, 1362, 1288, 1198, 1165, 1136 cm$^{-1}$; $[\alpha]_D^{24}$ + 28.1 ± 0.7° (c = 1.012, MeOH) Anal. (C$_{23}$H$_{29}$NO$_6$·0.5H$_2$O) Calcd. (%): C, 65.08; H, 7.12; N, 3.30 Found (%): C, 65.14; H, 7.06; N, 3.43 |
| Ic-84 | mp 133–135° C.; $^1$H-NMR (CDCl$_3$) δ 1.09 (1H, m), 1.22–1.70 (12H, m), 2.01 (1H, d, J = 3.3 Hz), 2.55 (1H, br s), 3.50–3.68 (2H, m), 3.96–4.09 (3H, m), 4.21–4.35 (2H, m), 6.11 (1H, m), 7.64 (1H, dd, J = 1.8, 8.7 Hz), 7.77 (1H, d, J = 8.7 Hz), 7.85 (1H, br s), 8.18 (1H, br s); IR (Nujol) 3323, 2924, 1736, 1599, 1562, 1514, 1448, 1281, 1217, 1142 cm$^{-1}$; $[\alpha]_D^{24}$ + 21.7 ± 0.6° (c = 1.017%, MeOH); Anal. (C$_{25}$H$_{32}$N$_2$O$_6$S) Calcd. (%): C, 61.45; H, 6.60; N, 5.73; S, 6.56 Found (%): C, 61.26; H, 6.41; N, 5.70; S, 6.48 |
| Ic-86 | $^1$H-NMR (CDCl$_3$) δ 1.16–1.69 (13H, m), 1.92 (1H, br s), 2.39 (1H, br s), 3.41 (2H, t, J = 5.4 Hz), 3.68 (1H, m), 3.92 (2H, s), 5.83 (2H, s), 7.65 (1H, dd, J = 2.1, 8.7 Hz), 7.83 (1H, d, J = 8.7 Hz), 8.23 (1H, d, J = 8.4 Hz), 8.25 (1H, s), 8.27 (1H, d, J = 2.1 Hz), 8.77 (1H, s), 12.53 (1H, br s); IR (Nujol) 3332, 2924, 1724, 1680, 1631, 1572, 1529, 1444, 1375, 1350, 1244, 1128 cm$^{-1}$; $[\alpha]_D^{24}$ + 23.6 ± 0.6° (c = 1.014%, MeOH); Anal. (C$_{23}$H$_{29}$N$_3$O$_5$S·0.4H$_2$O) Calcd. (%): C, 59.18; H, 6.43; N, 9.00; S, 6.87 Found (%): C, 59.33; H, 6.48; N, 8.87; S, 6.48 |
| Ic-95 | mp 118–120° C.; $^1$H-NMR (CDCl$_3$—DMSO—d$_6$) δ 1.16 (1H, m), 1.26 (3H, t, J = 7.2 Hz), 1.27–1.66 (12H, m), 2.01 (1H, m), 2.59 (1H, m), 3.52 (2H, m), 3.90 (1H, m), 4.00 (2H, s), 4.14 (2H, q, J = 7.2 Hz), 4.48 (2H, br s), 5.62 (1H, br s), 6.68 (1H, br s), 7.38 (1H, br d, J = 8.7 Hz), 7.81 (1H, d, J = 8.7 Hz), 7.96 (1H, s), 8.31 (1H, br s); IR (CHCl$_3$) 3442, 1724, 1655, 1516, 1477, 1435, 1225, 1217, 1132, 1059 cm$^{-1}$; $[\alpha]_D^{23}$ + 25.9 ± 0.7° (c = 1.012, MeOH) Anal. (C$_{26}$H$_{34}$N$_2$O$_6$S·0.2H$_2$O) Calcd. (%): C, 61.69; H, 6.85; N, 5.53; S, 6.33 Found (%): C, 61.71; H, 6.73; N, 5.48; S, 6.32 |

TABLE 41

| Compound No. | Physical property |
| --- | --- |
| Ic-99 | $^1$H-NMR (d$_6$—DMSO) δ 1.19–1.68 (13H, m), 1.93 (1H, br s), 2.43 (1H, br s), 3.41 (2H, t, J = 6.6 Hz), 3.49 (2H, s), 3.71 (1H, m), 3.92 (2H, s), 7.38 (1H, br s), 7.87 (1H, dd, J = 1.8, 8.7 Hz), 8.07 (1H, br s), 8.09 (1H, d, J = 8.4 Hz), 8.35 (1H, d, J = 6.6 Hz), 8.39 (1H, s), 8.85 (1H, d, J = 1.2 Hz); IR (Nujol) 3340, 3251, 2927, 1741, 1655, 1624, 1539, 1458, 1377, 1244, 1134 cm$^{-1}$; $[\alpha]_D^{25}$ + 24.2 ± 0.6° (c = 1.009%, MeOH); Anal. (C$_{23}$H$_{28}$N$_2$O$_5$S.0.5H$_2$O) Calcd. (%): C, 60.91; H, 6.44; N, 6.18; S, 7.07 Found (%): C, 60.89; H, 6.57; N, 5.80; S, 6.91 |
| Ic-115 | mp 133–135° C.; $^1$H-NMR (CDCl$_3$) δ 1.05 (1H, m), 1.21–1.34 (2H, m), 1.40–1.72 (10H, m), 2.02 (1H, m), 2.47 (3H, s), 2.53 (3H, s), 2.57 (1H, br s), 3.48–3.59 (2H, m), 3.97 (1H, m), 4.03 (2H, s), 6.12 (1H, d, J = 7.5 Hz), 7.05 (1H, s), 7.84 (1H, s), 7.94 (1H, s); IR (Nujol) 3344, 2540, 1730, 1614, 1539, 1219, 1142 cm$^{-1}$; $[\alpha]_D^{25}$ + 34.7 ± 0.7° (c = 1.012, MeOH) Anal. (C$_{23}$H$_{29}$NO$_4$S) Calcd. (%): C, 67.10; H, 7.27; N, 3.26; S, 7.64 Found (%): C, 66.81; H, 7.50; N, 3.18; S, 7.32 |
| Ic-128 | $^1$H-NMR (CDCl$_3$) δ 1.05 (1H, m), 1.19–1.68 (12H, m), 1.99 (1H, br s), 2.57 (1H, br s), 3.48 (2H, t, J = 6.3 Hz), 3.49 (2H, s), 3.95 (1H, m), 3.99 (2H, s), 4.85 (2H, br s), 6.27 (1H, d, J = 8.1 Hz), 7.47 (1H, d, J = 9.9 Hz), 7.76 (1H, s), 8.07 (1H, d, J = 8.4 Hz); IR (CHCl$_3$) 3435, 3192, 2954, 1730, 1637, 1520, 1435, 1275 cm$^{-1}$; $[\alpha]_D^{26}$ + 29.9 ± 0.7° (c = 1.011%, MeOH); Anal. (C$_{22}$H$_{26}$NO$_5$SF.0.4H$_2$O) Calcd. (%): C, 59.20; H, 6.14; N, 3.14; S, 7.18; F, 4.26 Found (%): C, 59.16; H, 5.90; N, 3.05; S, 7.09; F, 4.14 |
| Ic-129 | mp 135–137° C.; $^1$H-NMR (CDCl$_3$) δ 1.05 (1H, m), 1.22–1.69 (12H, m), 2.04 (1H, br s), 2.56 (1H, br s), 3.54 (2H, dt, J = 1.5, 6.6 Hz), 3.96 (1H, m), 3.98 (3H, s), 4.03 (2H, s), 6.12 (1H, d, J = 6.9 Hz), 7.52 (1H, d, J = 10.5 Hz), 7.77 (1H, s), 8.04 (1H, d, J = 8.4 Hz); IR (Nujol) 3334, 2924, 1745, 1618, 1535, 1498, 1462, 1415, 1281, 1259 cm$^{-1}$; $[\alpha]_D^{24}$ + 23.6 ± 0.6° (c = 1.014%, MeOH); Anal. (C$_{23}$H$_{28}$NO$_5$SF) Calcd. (%): C, 61.45; H, 6.28; N, 3.12; S, 7.13; F, 4.23 Found (%): C, 61.17; H, 6.33; N, 3.03; S, 7.04; F, 4.03 |
| Ic-135 | $^1$H-NMR (CDCl$_3$—DMSO—d$_6$) δ 1.17 (1H, m), 1.26–1.66 (12H, m), 2.00 (1H, m), 2.56 (1H, m), 3.53 (2H, t, J = 6.3 Hz), 3.86 (1H, m), 4.01 (2H, s), 6.62 (1H, br d, J = 8.1 Hz), 7.40 (2H, br s), 7.96 (1H, s), 8.17 (1H, s); IR (nujol) 1726, 1633, 1556, 1303, 1252, 1176, 1130 cm$^{-1}$; $[\alpha]_D^{24}$ + 19.5 ± 0.6° (c = 1.009, MeOH) |
| Ic-140 | mp 96–98° C.; $^1$H-NMR (DMSO—d$_6$) δ 1.18–1.31 (8H, m), 1.49–1.56 (5H, m), 1.94 (1H, m), 2.38 (1H, br s), 3.40 (2H, t, J = 6.5 Hz), 3.47 (2H, s), 3.68 (1H, m), 3.93 (2H, s), 6.88 (1H, br s), 7.26 (1H, dd, J = 1.5 and 8.7 Hz), 7.50 (1H, br s), 7.54 (1H, d, J = 8.7 Hz), 7.94 (1H, d, J = 1.5 Hz), 8.12 (1H, d, J = 6.6 Hz), 8.59 (1H, s); IR (Nujol) 3386, 3276, 3195, 3064, 2549, 1747, 1697, 1666, 1624, 1560, 1128 cm$^{-1}$; $[\alpha]_D^{25}$ + 22.0 ± 0.6° (c = 1.006, MeOH) Anal. (C$_{24}$H$_{30}$N$_2$O$_6$.0.8H$_2$O) Calcd. (%): C, 63.09; H, 6.97; N, 6.13 Found (%): C, 63.18; H, 6.98; N, 5.94 |

TABLE 42

| Compound No. | Physical property |
| --- | --- |
| Ic-142 | $^1$H-NMR (CDCl$_3$—CD$_3$OD) δ 1.19 (1H, m), 1.26–1.31 (2H, m), 1.39–1.64 (10H, m), 1.98 (1H, m), 2.55 (1H, br s), 3.50 (2H, t, J = 6.3 Hz), 3.86 (1H, m), 4.01 (2H, s), 6.44 (1H, br s), 6.88 (1H, d, J = 7.2 Hz), 7.29 (1H, br s), 7.50 (1H, d, J = 8.4 Hz), 7.89 (1H, dd, J = 1.8 and 8.4 Hz), 8.22 (1H, s), 8.45 (1H, d, J = 1.8 Hz); IR (CHCl$_3$) 3026, 3014, 2875, 1728, 1662, 1587, 1562, 1510, 1126 cm$^{-1}$; $[\alpha]_D^{25}$ + 19.6 ± 0.6° (c = 1.008, MeOH) Anal. (C$_{23}$H$_{28}$N$_2$O$_6$.0.5H$_2$O) Calcd. (%): C, 63.14; H, 6.68; N, 6.40 Found (%): C, 63.02; H, 6.49; N, 6.35 |
| Ie-34 | $^1$H-NMR (CDCl$_3$) δ 1.08 (1H, m), 1.23–1.71 (12H, m), 2.03 (1H, d, J = 3.3 Hz), 2.60 (1H, br s), 2.63 (2H, t, J = 6.9 Hz), 3.18 (2H, br s), 4.03 (1H, m), 6.45 (1H, d, J = 7.5 Hz), 7.38 (1H, d, J = 5.7 Hz), 7.42 (1H, t, J = 7.5 Hz), 7.58 (1H, d, J = 5.4 Hz), 7.63 (1H, d, J = 6.9 Hz), 7.96 (1H, d, J = 7.8 Hz); IR (CHCl$_3$) 3452, 2954, 1711, 1649, 1520, 1495, 1458, 1300, 1284 cm$^{-1}$; $[\alpha]_D^{26}$ + 38.1 ± 1.6° (c = 0.502%, MeOH); Anal. (C$_{22}$H$_{27}$NO$_3$S$_2$.0.3H$_2$O) Calcd. (%): C, 62.47; H, 6.58; N, 3.31; S, 15.16 Found (%): C, 62.53; H, 6.63; N, 3.38; S, 15.16 |
| Ie-49 | $^1$H-NMR (CDCl$_3$) δ 1.07 (1H, m), 1.29–1.68 (12H, m), 2.01 (1H, m), 2.55 (1H, m), 2.64 (2H, t, J = 7.5 Hz), 3.18 (2H, s), 3.44 (3H, s), 3.99 (1H, m), 4.78 (2H, s), 6.12 (1H, d, J = 7.2 Hz), 7.33–7.40 (2H, m), 7.79 (1H, dd, J = 6.9, 1.8 Hz), 8.17 (1H, s); IR (CHCl$_3$) 3440, 2670, 1710, 1650, 1573, 1562, 1509, 1425, 1297, 1238, 1224 cm$^{-1}$; $[\alpha]_D^{24.0}$ + 33.2 ± 0.7° (c = 1.019, MeOH); Anal. (C$_{24}$H$_{31}$NO$_5$S.0.2H$_2$O) Calcd. (%): C, 64.18; H, 7.05; N, 3.12 Found (%): C, 64.11; H, 7.11; N, 3.24 |

TABLE 42-continued

| Compound No. | Physical property |
| --- | --- |
| IIa-22 | $^1$H-NMR (CDCl$_3$) δ0.94 (1H, d, J = 10.2 Hz), 1.11 (3H, s), 1.23 (3H, s), 1.34–1.54 (6H, m), 1.65–1.89 (2H, m), 2.00 (1H, m), 2.13–2.39 (5H, m), 4.32 (1H, m), 5.75 (1H, dt, J = 15.9, 1.2 Hz), 6.22 (1H, d, J = 8.7 Hz), 6.98 (1H, dd, J = 2.1, 9.0 Hz), 6.99 (1H, td, J = 7.2, 15.9 Hz), 7.26 (1H, d, J = 2.1 Hz), 7.58 (1H, s), 8.08 (1H, d, J = 9.0 Hz); IR (KBr) 3300, 1695, 1603, 1522, 1468, 1417, 1236 cm$^{-1}$; [α]$_D^{26}$ + 31.3 ± 0.7° (c = 1.000, MeOH); Anal. (C$_{25}$H$_{31}$NO$_4$S.0.4H$_2$O) Calcd. (%): C, 66.91; H, 7.14; N, 3.12; S, 7.14 Found (%): C, 66.81; H, 7.05; N, 3.13; S, 7.07 |
| IIa-23 | mp 189–192° C.; $^1$H-NMR (CDCl$_3$) δ 0.96 (1H, d, J = 10.2 Hz), 1.13 (3H, s), 1.25 (3H, s), 1.28–2.39 (14H, m), 4.31 (1H, m), 5.78 (1H, d, J = 15.6 Hz), 6.19 (1H, d, J = 9.6 Hz), 6.99 (1H, m), 7.01 (1H, dd, J = 8.7, 2.7 Hz), 7.66 (1H, d, J = 8.7 Hz), 7.67 (1H, s), 7.89 (1H, d, J = 2.7 Hz); IR (Nujol) 3199, 2683, 1684, 1635, 1599, 1525, 1437, 1304, 1286, 1225 cm$^{-1}$; [α]$_D^{26.0}$ + 26.8 ± 0.7° (c = 1.011, MeOH); Anal. (C$_{25}$H$_{31}$NO$_4$S.0.3H$_2$O) Calcd. (%): C, 68.00; H, 7.08; N, 3.17; S, 7.26 Found (%): C, 68.09; H, 6.94; N, 3.16; S, 7.18 |

TABLE 43

| Compound No. | Physical property |
| --- | --- |
| IIa-24 | $^1$H-NMR (CDCl$_3$) δ 0.96 (1H, d, J = 9.9 Hz), 1.15 (3H, s), 1.27 (3H, s), 1.32–1.60 (6H, m), 1.66–1.90 (2H, m), 2.04 (1H, m), 2.17–2.43 (5H, m), 4.29 (1H, m), 5.79 (1H, d, J = 15.6 Hz), 6.49 (1H, d, J = 9.0 Hz), 6.93 (1H, dd, J = 2.7, 5.7 Hz), 7.02 (1H, td, J = 6.9, 15.6 Hz), 7.31 (1H, d, J = 2.7 Hz), 7.32 (1H, t, J = 5.7 Hz), 7.65 (1H, s), 12.09 (1H, s); IR (CHCl$_3$) 3521, 3454, 2686, 1695, 1651, 1624, 1585, 1562, 1522, 1456, 1271 cm$^{-1}$; [α]$_D^{27}$ + 29.4 ± 0.7° (c = 1.004, MeOH); Anal. (C$_{25}$H$_{31}$NO$_4$S.0.4H$_2$O) Calcd. (%): C, 66.91; H, 7.14; N, 3.12; S, 7.14 Found (%): C, 66.97; H, 7.01; N, 3.23; S, 7.17 |
| IIa-28 | mp 172–174° C.; $^1$H-NMR (CDCl$_3$) δ 0.96 (1H, d, J = 9.9 Hz), 1.13 (3H, s), 1.25 (3H, s), 1.30–2.42 (14H, m), 4.31 (1H, m), 5.79 (1H, dt, J = 15.6, 1.5 Hz), 6.08 (1H, d, J = 9.3 Hz), 7.03 (1H, dt, J = 15.6, 7.2 Hz), 7.17 (1H, dt, J = 8.7, 2.7 Hz), 7.80 (1H, dd, J = 8.7, 5.1 Hz), 7.83 (1H, s), 8.07 (1H, dd, J = 10.2, 2.7 Hz); IR (Nujol) 3374, 2719, 1698, 1650, 1627, 1525, 1442, 1431 cm$^{-1}$; [α]$_D^{24.0}$ + 28.2 ± 0.7° (c = 1.012, MeOH); Anal. (C$_{30}$H$_{37}$NO$_4$S.1.1H$_2$O) Calcd. (%): Calcd. (%): C, 67.57; H, 6.50; N, 3.15; S, 7.22 Found (%): C, 67.35; H, 6.76; N, 3.26; S, 7.12 |
| IIa-34 | mp 141–142° C.; $^1$H-NMR (CDCl$_3$) δ 0.96 (1H, d, J = 9.9 Hz), 1.16 (3H, s), 1.24 (3H, s), 1.29–2.42 (14H, m), 4.39 (1H, m), 5.77 (1H, d, J = 15.6 Hz), 6.43 (1H, d, J = 8.7 Hz), 7.01 (1H, dt, J = 15.6, 3.6 Hz), 7.38 (1H, d, J = 5.4 Hz), 7.43 (1H, t, J = 7.5 Hz), 7.54 (1H, d, J = 7.5 Hz), 7.59 (1H, d, J = 5.4 Hz), 7.96 (1H, d, J = 7.5 Hz); IR (Nujol) 3380, 2686, 1699, 1619, 1581, 1461, 1234, 1200 cm$^{-1}$; [α]$_D^{25.0}$ + 48.8 ± 0.9° (c = 1.009, MeOH); Anal. (C$_{25}$H$_{31}$NO$_3$S) Calcd. (%): C, 70.55; H, 7.34; N, 3.29; S, 7.53 Found (%): C, 70.35; H, 7.33; N, 3.31; S, 7.44 |
| IIa-51 | mp 211–213° C.; $^1$H-NMR (CDCl$_3$—CD$_3$OD) δ 0.94 (1H, d, J = 9.9 Hz), 1.15 (3H, s), 1.24 (3H, s), 1.36–1.55 (6H, m), 1.70 (1H, m), 1.83 (1H, m), 2.02 (1H, m), 2.15–2.38 (5H, m), 4.29 (1H, m), 5.74 (1H, d, J = 15.6 Hz), 6.90 (1H, dd, J = 2.1, 8.7 Hz), 6.90 (1H, dt, J = 15.6, 6.9 Hz), 7.00 (1H, d, J = 2.1 Hz), 7.56 (1H, d, J = 8.7 Hz), 7.99 (1H, s); IR (KBr) 3425, 3255, 2600, 1938, 1685, 1626, 1605, 1579, 1522, 1442, 1265, 1146, 1128, 1107 cm$^{-1}$; [α]$_D^{27}$ + 23.9 ± 0.6° (c = 1.004, MeOH); Anal. (C$_{25}$H$_{31}$NO$_5$.0.1H$_2$O) CaLcd. (%): C, 70.27; H, 7.36; N, 3.28 Found (%): C, 70.13; H, 7.34; N, 3.47 |
| IIa-52 | mp 159–160° C.; $^1$H-NMR (CDCl$_3$) δ 0.92 (1H, d, J = 9.9 Hz), 1.11 (3H, s), 1.21 (3H, s), 1.36–1.50 (6H, m), 1.63 (1H, m), 1.79 (1H, m), 1.98 (1H, s), 2.10–2.20 (4H, m), 2.30 (1H, s), 4.30 (1H, s), 5.69 (1H, d, J = 15.6 Hz), 6.20 (1H, d, J = 9.0 Hz), 6.91 (1H, dd, J = 2.4, 9.0 Hz), 6.94 (1H, dt, J = 15.6, 6.9 Hz), 7.33 (1H, d, J = 9.0 Hz), 7.56 (1H, d, J = 2.4 Hz), 7.98 (1H, s); IR (KBr) 3255, 2688, 1684, 1643, 1560, 1522, 1306, 1288, 1269, 1219, 1192, 1167, 1134 cm$^{-1}$; [α]$_D^{25}$ + 21.8 ± 0.6° (c = 1.020, MeOH); Anal. (C$_{25}$H$_{31}$NO$_5$) Calcd. (%): C, 70.57; H, 7.34; N, 3.29 Found (%): C, 70.41; H, 7.16; N, 3.34 |

TABLE 44

| Compound No. | Physical property |
|---|---|
| IIa-54 | $^1$H-NMR (CDCl$_3$) δ 0.95 (1H, d, J = 10.2 Hz), 1.14 (3H, s), 1.24 (3H, s), 1.32–1.57 (6H, m), 1.69–1.88 (2H, m), 2.02 (1H, m), 2.16–2.24 (4H, m), 2.35 (1H, m), 4.32 (1H, m), 5.78 (1H, dt, J = 15.3, 1.5 Hz), 6.02 (1H, d, J = 9.0 Hz), 7.02 (1H, dt, J = 15.3, 6.9 Hz), 7.09–7.15 (1H, m), 7.26 (1H, dd, J = 8.7, 2.1 Hz), 7.82 (1H, dd, J = 8.7, 5.4 Hz), 8.05 (1H, s); IR (CHCl$_3$) 3446, 2680, 1695, 1652, 1257, 1220, 1214 cm$^{-1}$; [α]$_D^{25.0}$ + 23.3 ± 0.6° (c = 1.008, MeOH); Anal. (C$_{25}$H$_{30}$FNO$_4$.0.4H$_2$O) Calcd. (%): C, 69.07; H, 7.14; F, 4.37; N, 3.22 Found (%): C, 68.82; H, 6.89; F, 4.49; N, 3.34 |
| IIa-66 | $^1$H-NMR (CDCl3) δ 0.95 (1H, d, J = 10.2 Hz), 1.14 (3H, s), 1.24 (3H, s), 1.40–1.55 (6H, m), 1.70–1.85 (2H, m), 2.00 (1H, br s), 2.12–2.37 (5H, m), 4.30 (1H, m), 5.80 (1H, d, J = 15.6 Hz), 6.17 (1H, d, J = 9.0 Hz), 6.68 (1H, d, J = 2.1 Hz), 6.88 (1H, d, J = 5.4 Hz), 6.94 (1H, d, J = 5.4 Hz), 7.03 (1H, dt, J = 15.6 and 6.9 Hz), 11.22 (1H, s); IR (CHCl$_3$) 3448, 3188, 1693, 1637, 1543, 1518, 1471, 1421, 1396, 1385, 1257, 1232 cm$^{-1}$; [α]$_D^{26}$ + 18.2 ± 0.6° (c = 1.005, MeOH) Anal. (C$_{23}$H$_{30}$N$_2$O$_3$S.0.2H$_2$O) Calcd. (%): C, 66.06; H, 7.33; N, 6.70; S, 7.66 Found (%): C, 66.19; H, 7.06; N, 6.83; S, 7.35 |
| IIa-81 | mp 167–168° C.; $^1$H-NMR (CDCl$_3$) δ 0.96 (1H, d, J = 10.2 Hz), 1.13 (3H, s), 1.23 (3H, s), 1.33–1.54 (6H, m), 1.64 (1H, m), 1.80 (1H, m), 1.99 (1H, br s), 2.12–2.38 (5H, m), 2.44 (3H, s), 4.31 (1H, m), 5.71 (1H, d, J = 15.6 Hz), 6.08 (1H, d, J = 9.6 Hz), 6.72 (1H, d, J = 2.1 Hz), 6.97 (1H, dt, J = 15.6 and 6.9 Hz), 7.30 (1H, d, J = 2.1 Hz), 7.97 (1H, s); IR (KBr) 3276, 2686, 1693, 1643, 1610, 1562, 1518, 1460, 1417, 1385, 1367, 1284, 1200, 1136 cm$^{-1}$; [α]$_D^{24}$ + 23.0 ± 0.6° (c = 1.020, MeOH) Anal. (C$_{26}$H$_{33}$NO$_5$.0.2HO) Calcd. (%): C, 70.47; H, 7.60; N, 3.16 Found (%): C, 70.50; H, 7.47; N, 3.35 |
| IIa-94 | $^1$H-NMR (CDCl$_3$) δ 0.97 (1H, d, J = 10.2 Hz), 1.14 (3H, s), 1.25 (3H, s), 1.42–1.56 (6H, m), 1.70–1.88 (2H, m), 2.00 (1H, m), 2.03 (3H, s), 2.18–2.38 (5H, m), 4.31 (1H, m), 4.55 (2H, m), 5.78 (1H, d, J = 15.6 Hz), 6.18–6.23 (2H, m), 6.98 (1H, dt, J = 15.6, 6.9 Hz), 7.34 (1H, dd, J = 1.8, 8.4 Hz), 7.77 (1H, s), 7.79 (1H, d, J = 8.4 Hz), 8.31 (1H, br s); IR (CHCl$_3$) 3446, 1695, 1655, 1514, 1471, 1435, 1369, 1222, 1215 cm$^{-1}$; [α]$_D^{24}$ + 23.4 ± 0.6° (c = 1.006, MeOH) Anal. (C$_{28}$H$_{36}$N$_2$O$_4$S.0.4H$_2$O) Calcd. (%): C, 66.74; H, 7.36; N, 5.56; S, 6.36 Found (%): C, 66.79; H, 7.23; N, 5.51; S, 6.39 |
| IIa-99 | mp 130–133° C.; 0.85 (1H, d, J = 9.6 Hz), 1.12 and 1.19 (3H, s), 1.25–2.38 (12H, m), 3.99 (1H, m), 5.72 (1H, d, J = 15.6 Hz), 6.79 (1H, dt, J = 6.6, 15.6 Hz), 7.38 (1H, s), 7.87 (1H, dd, J = 1.8, 8.7 Hz), 8.05–8.13 (3H, m), 8.31 (1H, s), 8.82 (1H, d, J = 1.2 Hz); IR (Nujol) 3375, 3178, 2918, 1703, 1653, 1626, 1527, 1460, 1398, 1255 cm$^{-1}$; [α]$_D^{25}$ + 27.9 ± 0.7° (c = 1.011%, MeOH); Anal. (C$_{26}$H$_{32}$N$_2$O$_4$S.0.7AcOEt) Calcd. (%): C, 65.23; H, 7.15; N, 5.28; S, 6.05 Found (%): C, 64.99; H, 6.91; N, 5.52; S, 6.18 |

TABLE 45

| Compound No. | Physical property |
|---|---|
| IIb-28 | $^1$H-NMR (CDCl$_3$) δ 0.97 (1H, d, J = 10.2 Hz), 1.13 (3H, s), 1.26 (3H, s), 1.59 (1H, ddd, J = 2.7, 5.7, 13.5 Hz), 1.95–2.57 (7H, m), 4.06–4.27 (4H, m), 4.33 (1H, m), 5.60–5.80 (2H, m), 6.18 (1H, d, J = 9.0 Hz), 7.17 (1H, dt, J = 3.0, 9.0 Hz), 7.79 (1H, dd, J = 4.8, 8.7 Hz), 7.89 (1H, s), 8.04 (1H, dd, J = 2.7, 9.9 Hz); IR (CHCl$_3$) 3442, 3022, 1734, 1651, 1603, 1564, 1516, 1496, 1471, 1433, 1244, 1119 cm$^{-1}$; [α]$_D^{25}$ + 43.8 ± 1.4° (c = 1.003%, MeOH); Anal. (C$_{24}$H$_{28}$NO$_4$SF.0.4H$_2$O) Calcd. (%): C, 63.67; H, 6.41; F, 4.20; N, 3.09; S, 7.08 Found (%): C, 63.73; H, 6.35; F, 4.11; N, 3.20; S, 7.07 |
| IIc-04 | mp 132–134° C.; $^1$H-NMR (CDCl$_3$) δ 0.94 (1H, d, J = 9.9 Hz), 1.13 (3H, s), 1.23 (3H, s), 1.40–1.86 (8H, m), 2.00 (1H, m), 2.13 (1H, m), 2.18–2.37 (2H, m), 3.53 (2H, t, J = 6.0 Hz), 4.04 (2H, s), 4.28 (1H, m), 6.14 (1H, d, J = 9.0 Hz), 7.31–7.36 (2H, m), 7.85 (1H, m); IR (Nujol) 3373, 3105, 2528, 1736, 1601, 1556, 1215, 1138 cm$^{-1}$; [α]$_D^{25}$ + 22.7 ± 0.6° (c = 1.004, MeOH); Anal. (C$_{20}$H$_{29}$NO$_4$S) Calcd. (%): C, 63.30; H, 7.70; N, 3.69; S, 8.45 Found (%): C, 63.10; H, 7.73; N, 3.74; S, 8.34 |
| IIc-17 | mp 125–126° C.; $^1$H-NMR (CDCl$_3$) δ 0.97 (1H, d, J = 10.2 Hz), 1.13 (3H, s), 1.25 (3H, s), 1.40–1.93 (8H, m), 2.02 (1H, m), 2.17–2.41 (3H, m), 3.53 (2H, t, J = 6.3 Hz), 4.02 (2H, s), 4.36 (1H, m), 6.21 (1H, d, J = 9.0 Hz), 7.37–7.49 (2H, m), 7.84 (1H, s), 7.87 (1H, m), 8.30 (1H, m); IR (Nujol) 3282, 2540, 1724, 1604, 1554, 1246, 1228, 1130, 1109 cm$^{-1}$; [α]$_D^{25}$ + 29.6 ± 0.7° (c = 1.013, MeOH); Anal. (C$_{24}$H$_{31}$NO$_4$S) Calcd. (%): C, 67.10; H, 7.27; N, 3.26; S, 7.46 Found (%): C, 66.88; H, 7.10; N, 3.30; S, 7.25 |

TABLE 45-continued

| Compound No. | Physical property |
| --- | --- |
| IIc-19 | $^1$H-NMR (CDCl$_3$) δ 0.96 (1H, d, J = 10.2 Hz), 1.13 (3H, s), 1.24 (3H, s), 1.40–1.92 (8H, m), 2.01 (1H, m), 2.17–2.40 (3H, m), 2.48 (3H, s), 3.47–3.58 (2H, m), 3.97 (1H, m), 4.02 (2H, s), 4.34 (1H, m), 6.21 (1H, d, J = 9.3 Hz), 7.28 (1H, m), 7.65 (1H, m), 7.75 (1H, s), 8.16 (1H, d, J = 8.4 Hz); IR (CHCl$_3$) 3442, 2567, 1780, 1732, 1649, 1514, 1242, 1134 cm$^{-1}$; [α]$_D^{25}$ + 28.7 ± 0.8° (c = 1.003, MeOH) Anal. (C$_{25}$H$_{33}$NO$_4$S.0.4H$_2$O) Calcd. (%): C, 66.61; H, 7.56; N, 3.11; S, 7.11 Found (%): C, 66.67; H, 7.37; N, 3.03; S, 6.88 |
| IIc-20 | mp 87–90° C.; $^1$H-NMR (CDCl$_3$) δ 0.97 (1H, d, J = 10.5 Hz), 1.14 (3H, s), 1.26 (3H, s), 1.40–1.92 (8H, m), 2.02 (1H, m), 2.18–2.41 (3H, m), 2.49 (3H, s), 3.54 (2H, t, J = 6.0 Hz), 4.02 (2H, s), 4.35 (1H, m), 6.20 (1H, d, J = 8.4 Hz), 7.23 (1H, dd, J = 0.6, 8.4 Hz), 7.74 (1H, d, J = 8.4 Hz), 7.80 (1H, s), 8.11 (1H, d, J = 0.6 Hz); IR (Nujol) 3411, 3357, 1736, 1604, 1531, 1219, 1134 cm$^{-1}$; [α]$_D^{25}$ + 27.4 ± 0.7° (c = 1.013, MeOH); Anal. (C$_{25}$H$_{33}$NO$_4$S.0.3H$_2$O) Calcd. (%): C, 66.87; H, 7.54; N, 3.12; S, 7.14 Found (%): C, 66.90; H, 7.50; N, 3.23; S, 7.05 |

TABLE 46

| Compound No. | Physical property |
| --- | --- |
| IIc-21 | mp 183–185° C.; $^1$H-NMR (d$_6$—DMSO) δ 0.84 (1H, d, J = 9.6 Hz), 1.11 (3H, s), 1.18 (3H, s), 1.22–1.60 (7H, m), 1.93 (1H, m), 2.10–2.34 (6H, m), 3.41 (2H, t, J = 6.3 Hz), 3.92 (2H, s), 3.97 (1H, m), 6.79 (1H, d, J = 7.8 Hz), 7.24 (1H, t, J = 7.8 Hz), 7.77 (1H, d, J = 7.8 Hz), 7.97 (1H, d, J = 6.9 Hz), 8.18 (1H, s), 10.39 (1H, br), 12.53 (1H, br); IR (Nujol) 3425, 3303, 3093, 2598, 1729, 1604, 1574, 1522, 1469, 1282, 1230, 1122 cm$^{-1}$; [α]$_D^{27}$ + 32.1 ± 0.7° (c = 1.000, MeOH); Anal. (C$_{24}$H$_{31}$NO$_5$S.0.4H$_2$O) Calcd. (%): C, 63.66; H, 7.08; N, 3.09; S, 7.08 Found (%): C, 63.79; H, 7.14; N, 3.15; S, 7.06 |
| IIc-22 | $^1$H-NMR (CDCl$_3$) δ 0.93 (1H, d, J = 10.2 Hz), 1.10 (3H, s), 1.23 (3H, s), 1.38–1.92 (8H, m), 1.99 (1H, m), 2.16–2.38 (3H, m), 3.46 (2H, t, J = 6.3 Hz), 3.95 (2H, s), 4.32 (1H, m), 6.32 (1H, d, J = 9.0 Hz), 6.96 (1H, dd, J = 2.1, 9.0 Hz), 7.24 (1H, t, J = 2.1 Hz), 7.51 (1H, s), 8.04 (1H, d, J = 9.0 Hz); IR (KBr) 3359, 1734, 1603, 1523, 1469, 1236, 1128 cm$^{-1}$; [α]$_D^{26}$ + 26.8 ± 0.7° (c = 1.015, MeOH); Anal. (C$_{24}$H$_{31}$NO$_5$S.0.4H$_2$O) Calcd. (%): C, 63.66; H, 7.08; N, 3.09; S, 7.08 Found (%): C, 63.64; H, 7.13; N, 3.07; S, 6.99 |
| IIc-23 | $^1$H-NMR (CDCl$_3$) δ 0.98 (1H, d, J = 10.5 Hz), 1.12 (3H, s), 1.24 (3H, s), 1.38–2.40 (12H, m), 3.47 (2H, t, J = 6.6 Hz), 3.97 (2H, s), 4.33 (1H, m), 5.36 (2H, br s), 6.28 (1H, d, J = 9.0 Hz), 7.00 (1H, dd, J = 2.1, 8.7 Hz), 7.65 (1H, d, J = 8.7 Hz), 7.71 (1H, s), 7.98 (1H, d, J = 2.1 Hz); IR (CHCl$_3$) 3438, 3238, 1730, 1637, 1601, 1518, 1436, 1124 cm$^{-1}$; [α]$_D^{24}$ + 23.7 ± 0.6° (c = 1.004, MeOH); Anal. (C$_{24}$H$_{31}$NO$_5$S.0.5H$_2$O) Calcd. (%): C, 63.41; H, 7.10; N, 3.08; S, 7.05 Found (%): C, 63.40; H, 6.98; N, 3.25; S, 7.09 |
| IIc-24 | $^1$H-NMR (CDCl$_3$) δ 0.96 (1H, d, J = 10.5 Hz), 1.16 (3H, s), 1.20 (3H, s), 1.40–1.92 (8H, m), 2.04 (1H, m), 2.18–2.42 (3H, m), 3.55 (2H, t, J = 6.3 Hz), 4.04 (2H, s), 4.30 (1H, m), 6.55 (1H, d, J = 8.7 Hz), 6.93 (1H, dd, J = 2.4, 6.6 Hz), 7.32 (1H, d, J = 2.4 Hz), 7.33 (1H, d, J = 6.6 Hz), 7.67 (1H, s), 12.10 (1H, s); IR (CHCl$_3$) 3508, 3450, 2684, 1780, 1732, 1624, 1585, 1562, 1523, 1456, 1269 cm$^{-1}$; [α]$_D^{27}$ + 28.4 ± 0.7° (c = 1.000, MeOH); Anal. (C$_{24}$H$_{31}$NO$_5$S.0.5H$_2$O) Calcd. (%): C, 63.41; H, 7.10; N, 3.08; S, 7.05 Found (%): C, 63.48; H, 6.98; N, 3.16; S, 6.98 |
| IIc-27 | $^1$H-NMR (CDCl$_3$) δ 0.96 (1H, d, J = 10.2 Hz), 1.13 (3H, s), 1.25 (3H, s), 1.40–1.92 (8H, m), 2.02 (1H, m), 2.17–2.41 (3H, m), 3.53 (2H, t, J = 6.6 Hz), 4.03 (2H, s), 4.32 (1H, m), 6.18 (1H, d, J = 8.7 Hz), 7.21 (1H, dt, J = 2.4, 9.0 Hz), 7.53 (1H, dd, J = 2.4, 8.4 Hz), 8.33 (1H, dd, J = 5.1, 9.0 Hz); IR (CHCl$_3$) 3508, 3442, 1780, 1732, 1651, 1603, 1516, 1468, 1244, 1122 cm$^{-1}$; [α]$_D^{25}$ + 29.2 ± 0.7° (c = 1.006, MeOH); Anal. (C$_{24}$H$_{30}$FNO$_4$S.0.3H$_2$O) Calcd. (%): C, 63.64; H, 6.81; F, 4.19; N, 3.09; S, 7.08 Found (%): C, 63.65; H, 6.76; F, 4.10; N, 3.14; S, 7.16 |

TABLE 47

| Compound No. | Physical property |
|---|---|
| IIc-28 | mp 144–146° C.; $^1$H-NMR (CDCl$_3$) δ 0.97 (1H, d, J = 10.5 Hz), 1.13 (3H, s), 1.25 (3H, s), 1.40–1.92 (8H, m), 2.02 (1H, m), 2.17–2.41 (3H, m), 3.52–3.57 (2H, m), 4.03 (2H, s), 4.33 (1H, m), 6.16 (1H, d, J = 8.4 Hz), 7.17 (1H, dt, J = 2.7, 8.7 Hz), 7.78 (1H, dd, J = 5.1, 8.7 Hz), 8.06 (1H, dd, J = 2.7, 9.9 Hz); IR (Nujol) 3286, 2538, 1722, 1608, 1552, 1244, 1136 cm$^{-1}$; [α]$_D^{25}$ + 27.3 ± 0.7° (c = 1.009, MeOH); Anal. (C$_{24}$H$_{30}$FNO$_4$S) Calcd. (%): C, 64.41; H, 6.76; F, 4.24; N, 3.13; S, 7.16 Found (%): C, 64.23; H, 6.84; F, 4.16; N, 3.19; S, 7.12 |
| IIc-34 | mp 95–96° C.; $^1$H-NMR (CDCl$_3$) δ 0.97 (1H, d, J = 10.5 Hz), 1.17 (3H, s), 1.24 (3H, s), 1.40–1.96 (8H, m), 2.02 (1H, m), 2.18–2.41 (3H, m), 3.47–3.58 (2H, m), 4.01 (2H, s), 4.40 (1H, m), 6.50 (1H, d, J = 8.7 Hz), 7.38 (1H, d, J = 5.7 Hz), 7.43 (1H, d, J = 7.8 Hz), 7.55 (1H, d, J = 7.8 Hz), 7.59 (1H, d, J = 5.7 Hz), 7.96 (1H, dd, J = 1.2, 7.8 Hz); IR (Nujol) 3265, 2544, 1728, 1608, 1577, 1550, 1319, 1240, 1225, 1128, 1111 cm$^{-1}$; [α]$_D^{25}$ + 45.6 ± 0.9° (c = 1.006, MeOH); Anal. (C$_{24}$H$_{31}$NO$_4$S) Calcd. (%): C, 67.10; H, 7.27; N, 3.26; S, 7.46 Found (%): C, 66.88; H, 7.14; N, 3.34; S, 7.43 |
| IIc-39 | $^1$H-NMR (CDCl$_3$) δ 0.99 (1H, d, J = 10.2 Hz), 1.17 (3H, s), 1.24 (3H, s), 1.44–1.94 (8H, m), 2.02 (1H, m), 2.18–2.40 (3H, m), 3.53 (2H, t, d = 6.3 Hz), 3.98 (3H, s), 4.01 (2H, s), 4.40 (1H, m), 6.43 (1H, s), 6.49 (1H, d, J = 8.7 Hz), 7.42 (1H, t, J = 7.5 Hz), 7.58 (1H, dd, J = 0.9, 7.5 Hz), 7.93 (1H, dd, J = 0.9, 7.5 Hz); IR (CHCl$_3$) 3455, 1780, 1732, 1649, 1508, 1373, 1205, 1151 cm$^{-1}$; [α]$_D^{24}$ + 41.7 ± 0.8° (c = 1.007, MeOH); Anal. (C$_{25}$H$_{33}$NO$_5$S.0.2H$_2$O) Calcd. (%): C, 64.82; H, 7.27; N, 3.02; S, 6.92 Found (%): C, 64.85; H, 7.30; N, 3.10; S, 6.64 |
| IIc-41 | $^1$H-NMR (CDCl$_3$) δ 0.98 (1H, d, J = 9.9 Hz), 1.19 (3H, s), 1.25 (3H, s), 1.46–1.96 (8H, m), 2.03 (1H, m), 2.22–2.41 (3H, m), 3.53 (2H, t, J = 6.3 Hz), 4.00 (2H, s), 4.43 (1H, m), 6.53 (1H, d, J = 9.3 Hz), 7.44–7.56 (3H, m), 7.66 (1H, d, J = 6.3 Hz), 7.91 (1H, m), 8.18 (1H, m), 8.30 (1H, d, J = 7.5 Hz); IR (CHCl$_3$) 3454, 1780, 1731, 1649, 1512, 1444, 1217, 1122 cm$^{-1}$; [α]$_D^{25}$ + 45.4 ± 0.8° (c = 1.013, MeOH); Anal. (C$_{28}$H$_{33}$NO$_4$S.0.3H$_2$O) Calcd. (%): C, 69.34; H, 6.98; N, 2.89; S, 6.61 Found (%): C, 69.21; H, 7.01; N, 3.04; S, 6.59 |
| IIc-49 | $^1$H-NMR (CDCl$_3$) δ 0.97 (1H, d, J = 9.9 Hz), 1.17 (3H, s), 1.25 (3H, s), 1.49–2.39 (12H, m), 3.45 (2H, s), 3.51 (2H, t, J = 6.3 Hz), 4.00 (3H, s), 4.37 (1H, m), 4.79 (2H, s), 6.20 (1H, d, J = 9.3 Hz), 7.32–7.40 (2H, m), 7.74 (1H, dd, J = 7.2, 1.5 Hz), 8.16 (1H, s); IR (CHCl$_3$) 3444, 2829, 1733, 1650, 1573, 1508, 1471, 1425, 1384, 1367, 1214 cm$^{-1}$; [α]$_D^{24.0}$ + 24.8 ± 0.6° (c = 1.020, MeOH); Anal. (C$_{26}$H$_{35}$NO$_6$.0.5H$_2$O) Calcd. (%): C, 66.93; H, 7.78; N, 3.00 Found (%): C, 66.85; H, 7.78; N, 3.10 |

TABLE 48

| Compound No. | Physical property |
|---|---|
| IIc-51 | $^1$H-NMR (CDCl$_3$) δ 0.93 (1H, d, J = 9.9 Hz), 1.14 (3H, s), 1.23 (3H, s), 1.41–1.90 (8H, m), 2.00 (1H, m), 2.17–2.38 (3H, m), 3.49 (2H, t, J = 6.3 Hz), 3.99 (2H, s), 4.29 (1H, m), 6.27 (1H, d, J = 9.0 Hz), 6.89 (1H, dd, J = 2.1, 8.7 Hz), 6.99 (1H, d, J = 2.1 Hz), 7.56 (1H, d, J = 8.7 Hz), 8.00 (1H, s); IR (KBr) 3475, 1734, 1626, 1560, 1518, 1493, 1471, 1441, 1385, 1367, 1265, 1221, 1122 cm$^{-1}$; [α]$_D^{27}$ + 22.3 ± 0.6° (c = 1.000, MeOH); Anal. (C$_{24}$H$_{31}$NO$_6$.0.5H$_2$O) Calcd. (%): C, 65.74; H, 7.35; N, 3.19 Found (%): C, 65.79; H, 7.43; N, 3.36 |
| IIc-52 | $^1$H-NMR (CDCl$_3$) δ 0.98 (1H, d, J = 10.5 Hz), 1.13 (3H, s), 1.24 (3H, s), 1.48–1.90 (8H, m), 2.01 (1H, m), 2.18–2.40 (3H, m), 3.49 (2H, t, J = 6.5 Hz), 3.95 (1H, d, J = 16.5 Hz), 4.02 (1H, d, J = 16.5 Hz), 4.32 (1H, m), 6.12 (1H, d, J = 9.0 Hz), 6.91 (1H, dd, J = 2.7, 9.0 Hz), 7.36 (1H, d, J = 9.0 Hz), 7.52 (1H, d, J = 9.0 Hz), 7.98 (1H, s); IR (CHCl$_3$) 3442, 3265, 1730, 1643, 1620, 1558, 1514, 1468, 1385, 1367, 1190, 1167, 1136 cm$^{-1}$; [α]$_D^{27}$ + 21.6 ± 0.6° (c = 1.006, MeOH); Anal. (C$_{24}$H$_{31}$NO$_6$.0.5H$_2$O) Calcd. (%): C, 65.74; H, 7.35; N, 3.19 Found (%): C, 65.80; H, 7.46; N, 3.34 |
| IIc-56 | $^1$H-NMR (CDCl$_3$) δ 0.99 (1H, d, J = 10.2 Hz), 1.25 (6H, s), 1.47–1.79 (7H, m), 1.92–2.05 (2H, m), 2.19 (1H, m), 2.25–2.39 (2H, m), 3.51 (2H, t, J = 6.3 Hz), 3.96 (1H, d, J = 16.2 Hz), 4.00 (1H, d, J = 16.2 Hz), 4.46 (1H, m), 6.89 (1H, d, J = 2.1 Hz), 7.37 (1H, t, J = 7.8 Hz), 7.69 (1H, d, J = 2.1 Hz), 7.74 (1H, dd, J = 1.2, 7.8 Hz), 7.88 (1H, d, J = 9.3 Hz), 8.13 (1H, dd, J = 1.2, 7.8 Hz); IR (CHCl$_3$) 3435, 2665, 2573, 2474, 1780, 1732, 1651, 1606, 1595, 1547, 1535, 1473, 1421, 1367, 1352, 1325, 1296, 1167, 1120 cm$^{-1}$; [α]$_D^{25.5}$ + 14.7 ± 0.5° (c = 1.007, MeOH); Anal. (C$_{24}$H$_{31}$NO$_5$.0.3H$_2$O) Calcd. (%): C, 68.81; H, 7.60; N, 3.34 Found (%): C, 68.71; H, 7.60; N, 3.44 |

TABLE 48-continued

| Compound No. | Physical property |
| --- | --- |
| IIc-65 | mp 191–192° C.; $^1$H-NMR (CDCl$_3$) δ 0.96 (1H, d, J = 10.5 Hz), 1.15 (3H, s), 1.25 (3H, s), 1.46–1.88 (8H, m), 2.01 (1H, m), 2.11 (1H, m), 2.21–2.37 (2H, m), 3.51–3.58 (2H, m), 4.07 (2H, s), 4.30 (1H, m), 6.21 (1H, d, J = 9.3 Hz), 6.68 (1H, d, J = 1.2 Hz), 6.99 (1H, d, J = 5.4 Hz), 7.23 (1H, dd, J = 0.6, 5.4 Hz), 11.27 (1H, s) ; IR (KBr) 3433, 3276, 2663, 2534, 1736, 1591, 1541, 1508, 1473, 1458, 1244, 1228, 1211, 1151 cm$^{-1}$; [α]$_D^{25}$ + 18.0 ± 06° (c = 1.008, MeOH); Anal. (C$_{22}$H$_{30}$N$_2$O$_4$S.0.1H$_2$O) Calcd. (%): C, 62.86; H, 7.24; N, 6.66; S, 7.63 Found (%): C, 62.81; H, 7.30; N, 6.80; S, 7.47 |
| IIc-66 | $^1$H-NMR (CDCl$_3$) δ 0.96 (1H, d, J = 10.2 Hz), 1.14 (3H, s), 1.24 (3H, s), 1.46–1.88 (8H, m), 2.01 (1H, m), 2.14 (1H, m), 2.21–2.37 (2H, m), 3.53 (2H, t, J = 6.6 Hz), 4.07 (2H, s), 4.29 (1H, m), 6.20 (1H, d, J = 9.3 Hz), 6.64 (1H, d, J = 2.1 Hz), 6.86 (1H, d, J = 5.4 Hz), 6.92 (1H, d, J = 5.4 Hz), 11.06 (1H, s); IR (CHCl$_3$) 3448, 3209, 1726, 1631, 1543, 1518, 1126 cm$^{-1}$; [α]$_D^{25}$ + 14.4 ± 0.5° (c = 1.007, MeOH); Anal. (C$_{22}$H$_{30}$N$_2$O$_4$S.0.4H$_2$O) Calcd. (%): C, 62.06; H, 7.29; N, 6.58; S, 7.53 Found (%): C, 62.02; H, 7.31; N, 6.67; S, 7.56 |

TABLE 49

| Compound No. | Physical property |
| --- | --- |
| IIc-81 | $^1$H-NMR (CDCl$_3$) δ 0.92 (1H, d, J = 10.2 Hz), 1.09 (3H, s), 1.20 (3H, s), 1.41–1.73 (7H, m), 1.82 (1H, m), 1.96 (1H, br s), 2.14–2.35 (3H, m), 2.41 (3H, s), 3.46 (2H, t, J = 6.3 Hz), 3.98 (2H, s), 4.27 (1H, m), 6.22 (1H, d, J = 9.0 Hz), 6.72 (1H, d, J = 2.1 Hz), 7.24 (1H, d, J = 2.1 Hz), 8.03 (1H, s); IR (CHCl$_3$) 3599, 3442, 3265, 2565, 1730, 1645, 1608, 1570, 1514, 1460, 1417, 1385, 1367, 1329, 1286, 1240, 1137 cm$^{-1}$; [α]$_D^{24}$ + 24.2 ± 0.6° (c = 1.014, MeOH) Anal. (C$_{25}$H$_{33}$NO$_6$.0.4H$_2$O) Calcd. (%): C, 66.62; H, 7.55; N, 3.10 Found (%): C, 66.66; H, 7.47; N, 3.29 |
| IIc-84 | $^1$H-NMR (CDCl$_3$) δ 0.98 (1H, d, J = 10.2 Hz), 1.12 (3H, s), 1.25 (3H, s), 1.34 (2H, t, J = 7.5 Hz), 1.44–2.41 (10H, m), 3.56 (2H, br t, J = 5.4 Hz), 4.04 (2H, br s), 4.22–4.40 (3H, m), 6.22 (1H, d, J = 9.0 Hz), 7.65 (1H, dd, J = 1.5, 8.7 Hz), 7.77 (1H, d, J = 8.7 Hz), 7.78 (1H, br s), 8.22 (1H, br s); IR (CHCl$_3$) 3437, 2924, 1730, 1651, 1514, 1441, 1319 cm$^{-1}$; [α]$_D^{24}$ + 20.9 ± 0.6° (c = 1.010%, MeOH), Anal. (C$_{27}$H$_{36}$N$_2$O$_6$S.0.4H$_2$O) Calcd. (%): C, 61.90; H, 7.08; N, 5.35; S, 6.12 Found (%): C, 61.82; H, 6.85; N, 5.30; S, 6.09 |
| IIc-86 | $^1$H-NMR (d$_6$—DMSO) δ 0.85 (1H, d, J = 8.7 Hz), 1.11 (3H, s), 1.18 (3H, s), 1.27–2.38 (12H, m), 3.41 (2H, t, J = 6.3 Hz), 3.73 (2H, s), 3.97 (1H, m), 5.83 (2H, br s), 7.61 (1H, dd, J = 2.1, 8.7 Hz), 7.83 (1H, d, J = 8.7 Hz), 7.98 (1H, d, J = 6.6 Hz), 8.18 (1H, br s), 8.28 (1H, d, J = 2.1 Hz), 8.73 (1H, s), 12.54 (1H, br s); IR (Nujol) 3334 2923, 1676, 1633, 1571, 1523, 1442, 1377, 1244, 1126 cm$^{-1}$; [α]$_D^{24}$ + 19.1 ± 0.6° (c = 1.018%, MeOH); Anal. (C$_{25}$H$_{33}$N$_3$O$_5$S.0.4H$_2$O) Calcd. (%): C, 60.68; H, 6.88; N, 8.49; S, 6.48 Found (%): C, 60.73; H, 6.86; N, 8.67; S, 6.41 |
| IIc-94 | $^1$H-NMR (CDCl$_3$) δ 0.98 (1H, d, J = 10.2 Hz), 1.15 (3H, s), 1.26 (3H, s), 1.48–1.91 (8H, m), 2.02 (1H, m), 2.06 (3H, s), 2.18–2.40 (3H, m), 3.51 (2H, t, J = 6.3 Hz), 3.90 and 3.97 (each 1H, ABq, J = 16.2 Hz), 4.36 (1H, m), 4.49 (1H, dd, J = 6.3, 15.0 Hz), 4.61 (1H, dd, J = 6.3, 15.0 Hz), 6.27 (1H, br d, J = 9.0 Hz), 6.41 (1H, br s), 7.33 (1H, br d, J = 8.7 Hz), 7.76 (1H, s), 7.79 (1H, d, J = 8.7 Hz), 8.29 (1H, br s); IR (CHCl$_3$) 3444, 1733, 1653, 1516, 1471, 1435, 1367, 1240, 1130 cm$^{-1}$; [α]$_D^{24}$ + 23.2 ± 0.6° (c = 1.015, MeOH) Anal. (C$_{27}$H$_{36}$N$_2$O$_5$S.0.3H$_2$O) Calcd. (%): C, 64.08; H, 7.29; N, 5.54; S, 6.34 Found (%): C, 63.99; H, 7.24; N, 5.46; S, 6.35 |
| IIc-95 | mp 133–134° C.; $^1$H-NMR (CDCl$_3$—DMSO—d$_6$) δ 0.96 (1H, d, J = 9.9 Hz), 1.13 (3H, s), 1.25 (3H, s), 1.26 (3H, t, J = 7.5 Hz), 1.42–2.03 (9H, m), 2.22–2.39 (3H, m), 3.52 (2H, t, J = 6.6 Hz), 3.99 (2H, s), 4.14 (2H, q, J = 7.5 Hz), 4.29 (1H, m), 4.49 (2H, br s), 5.50 (1H, br s), 6.34 (1H, br d, J = 8.7 Hz), 7.38 (1H, d, J = 8.1 Hz), 7.82 (1H, d, J = 8.1 Hz), 7.84 (1H, br s), 8.30 (1H, s); IR (CHCl$_3$) 3446, 1722, 1653, 1514, 1471, 1435, 1385, 1238, 1132, 1061 cm$^{-1}$; [α]$_D^{23}$ + 22.9 ± 0.6° (c = 1.013, MeOH) Anal. (C$_{28}$H$_{38}$N$_2$O$_6$S) Calcd. (%): C, 63.37; H, 7.22; N, 5.28; S, 6.04 Found (%): C, 63.18; H, 7.14; N, 5.23; S, 5.95 |

TABLE 50

| Compound No. | Physical property |
| --- | --- |
| IIc-96 | $^1$H-NMR (CDCl$_3$) δ 0.98 (1H, d, J = 10.5 Hz), 1.16 (3H, s), 1.26 (3H, s), 1.47–1.72 (7H, m), 1.86 (1H, m), 2.02 (1H, m), 2.18–2.39 (3H, m), 2.92 (3H, s), 3.51 (2H, m), 3.96 and 4.03 (each 1H, ABq, J = 16.5 Hz), 4.36 (1H, m), 4.44 (2H, br s), 5.75 (1H, br s), 6.24 (1H, br d, J = 8.7 Hz), 7.41 (1H, br d, J = 8.1 Hz), 7.76 (1H, s), 7.83 (1H, d, J = 8.1 Hz), 8.42 (1H, br s); IR (CHCl$_3$) 3442, 1734, 1649, 1516, 1496, 1471, 1437, 1327, 1223, 1149, 1074 cm$^{-1}$; $[\alpha]_D^{26}$ + 19.2 ± 0.6° (c = 1.010, MeOH) Anal. (C$_{26}$H$_{36}$N$_2$O$_6$S$_2$.0.4H$_2$O) Calcd. (%): C, 57.41; H, 6.82; N, 5.15; S, 11.79 Found (%): C, 57.36; H, 6.65; N, 5.02; S, 11.65 |
| IIc-97 | $^1$H-NMR (CDCl$_3$) δ 0.96 (1H, d, J = 10.2 Hz), 1.13 (3H, s), 1.24 (3H, s), 1.48–1.72 (7H, m), 1.89 (1H, m), 2.00 (1H, m), 2.16–2.38 (3H, m), 3.49 (2H, t, J = 6.6 Hz), 3.89 and 3.96 (each 1H, ABq, J = 16.5 Hz), 4.25 (1H, br d, J = 15.0 Hz), 4.32 (1H, m), 4.46 (1H, br d, J = 15.0 Hz), 6.37 (1H, d, J = 8.4 Hz), 7.21 (1H, dd, J = 1.2, 8.7 Hz), 7.71 (1H, d, J = 8.7 Hz), 7.74 (1H, s), 8.21 (1H, br s); IR (CHCl$_3$) 3440, 1720, 1645, 1601, 1518, 1471, 1437, 1240, 1215, 1132 cm$^{-1}$; $[\alpha]_D^{25}$ + 23.7 ± 0.6° (c = 1.009, MeOH) Anal. (C$_{26}$H$_{35}$N$_3$O$_5$S.0.5H$_2$O) Calcd. (%): C, 61.15; H, 7.11; N, 8.23; S, 6.28 Found (%): C, 61.02; H, 6.81; N, 8.14; S, 6.30 |
| IIc-99 | mp 164–166° C.; $^1$H-NMR (d$_6$—DMSO) δ 0.85 (1H, d, J = 9.6 Hz), 1.12 (3H, s), 1.19 (3H, s), 1.24–2.37 (12H, m), 3.41 (2H, t, J = 6.3 Hz), 3.92 (2H, s), 3.99 (1H, m), 7.38 (1H, br s), 7.87 (1H, dd, J = 2.1, 8.7 Hz), 8.05–8.13 (3H, m), 8.32 (1H, s), 8.82 (1H, d, J = 1.2 Hz); IR (Nujol) 3448, 3356, 3211, 2925, 1718, 1691, 1639, 1520, 1462, 1402, 1254, 1144 cm$^{-1}$; $[\alpha]_D^{25}$ + 28.4 ± 0.7° (c = 1.008%, MeOH); Anal. (C$_{25}$H$_{32}$N$_2$O$_5$S.0.2H$_2$O) Calcd. (%): C, 63.05; H, 6.86; N, 5.88; S, 6.73 Found (%): C, 63.01; H, 6.78; N, 5.84; S, 6.70 |
| IIc-115 | $^1$H-NMR (CDCl$_3$) δ 0.97 (1H, d, J = 10.2 Hz), 1.14 (3H, s), 1.25 (3H, s), 1.40–1.92 (8H, m), 2.02 (1H, m), 2.18–2.41 (3H, m), 2.46 (3H, s), 2.53 (3H, s), 3.47–3.58 (2H, m), 4.02 (2H, s), 4.35 (1H, m), 6.22 (1H, d, J = 8.4 Hz), 7.05 (1H, s), 7.83 (1H, s), 7.93 (1H, s); IR (CHCl$_3$) 3508, 3440, 1780, 1732, 1649, 1514, 1242, 1126 cm$^{-1}$; $[\alpha]_D^{25}$ + 30.4 ± 0.7° (c = 1.017, MeOH) Anal. (C$_{26}$H$_{35}$NO$_4$S.0.2H$_2$O) Calcd. (%): C, 67.71; H, 7.74; N, 3.01; S, 6.95 Found (%): C, 67.37; H, 7.91; N, 2.95; S, 6.79 |
| IIc-128 | $^1$H-NMR (CDCl$_3$) δ 0.99 (1H, d, J = 10.5 Hz), 1.12 (3H, s), 1.25 (each 3H, s), 1.41–2.41 (12H, m), 3.49 (2H, t, J = 7.5 Hz), 3.99 (2H, s), 4.32 (2H, s), 5.05 (2H, br s), 6.29 (1H, d, J = 9.0 Hz), 7.48 (1H, d, J = 10.2 Hz), 7.67 (1H, s), 8.09 (1H, d, J = 8.7 Hz); IR (CHCl3) 3579, 3438, 3192, 2924, 1730, 1635, 1518, 1433, 1277 cm$^{-1}$; $[\alpha]_D^{26}$ + 22.4 ± 0.6° (c = 1.014%, MeOH); Anal. (C$_{24}$H$_{30}$NO$_5$SF.0.6H$_2$O) Calcd. (%): C, 60.77; H, 6.63; N, 2.95; S, 6.76; F, 4.00 Found (%): C, 60.72; H, 6.35; N, 2.85; S, 6.58; F, 4.01 |

TABLE 51

| Compound No. | Physical property |
| --- | --- |
| IIc-129 | $^1$H-NMR (CDCl$_3$) δ 0.97 (1H, d, J = 10.5 Hz), 1.15 (3H, s), 1.25 (3H, s), 1.44–2.40 (12H, m), 3.55 (2H, t, J = 6.3 Hz), 3.98 (3H, s), 4.02 (2H, s), 4.32 (1H, m), 6.19 (1H, d, J = 6.6 Hz), 7.62 (1H, d, J = 10.5 Hz), 7.69 (1H, s), 8.07 (1H, d, J = 8.1 Hz); IR (CHCl$_3$) 3444, 2924, 1780, 1732, 1649, 1512, 1466, 1415, 1263, 1225 cm$^{-1}$; $[\alpha]_D^{25}$ + 22.5 ± 0.6° (c = 1.006%, MeOH); Anal. (C$_{25}$H$_{32}$NO$_5$SF.0.2H$_2$O) Calcd. (%): C, 62.40; H, 6.79; N, 2.91; S, 6.66; F, 3.95 Found (%): C, 62.32; H, 6.74; N, 2.86; S, 6.72; F, 3.88 |
| IIc-135 | $^1$H-NMR (CDCl$_3$—DMSO—d$_6$) δ 0.93 (1H, d, J = 10.2 Hz), 1.16 (3H, s), 1.23 (3H, s), 1.42–1.74 (7H, m), 1.91–2.02 (2H, m), 2.20–2.36 (3H, m), 3.52 (2H, t, J = 6.9 Hz), 4.00 (2H, s), 4.27 (1H, m), 6.34 (1H, br d, J = 8.4 Hz), 7.35 (1H, dd, J = 2.1, 8.7 Hz), 7.42 (1H, d, J = 8.7 Hz), 7.96 (1H, d, J = 2.1 Hz), 8.11 (1H, s); IR (nujol) 3440, 1724, 1635, 1556, 1298, 1252, 1173, 1128 cm$^{-1}$; $[\alpha]_D^{24}$ + 17.1 ± 0.6° (c = 1.004, MeOH) |
| IIe-04 | mp 79–81° C.; $^1$H-NMR (CDCl$_3$) δ 0.95 (1H, d, J = 9.9 Hz), 1.21 (3H, s), 1.23 (3H, s), 1.36–1.88 (8H, m), 2.00 (1H, m), 2.10–2.38 (3H, m), 2.65 (2H, t, J = 6.9 Hz), 3.17 (1H, d, J = 14.7 Hz), 3.22 (1H, d, J = 14.7 Hz), 4.27 (1H, m), 6.18 (1H, d, J = 9.0 Hz), 7.32–7.36 (2H, m), 7.86 (1H, dd, J = 1.5, 2.4 Hz); IR (Nujol) 3396, 3361, 3109, 3076, 2617, 1720, 1631, 1593, 1543, 1508, 1234, 1221, 1124 cm$^{-1}$; $[\alpha]_D^{26}$ + 29.4 ± 0.7° (c = 1.005, MeOH). Anal. (C$_{20}$H$_{29}$NO$_3$S$_2$) Calcd. (%): C, 60.72; H, 7.39; N, 3.54; S, 16.21 Found (%): C, 60.73; H, 7.45; N, 3.61; S, 16.17 |

TABLE 51-continued

| Compound No. | Physical property |
| --- | --- |
| IIe-17 | mp 176–178° C.; $^1$H-NMR (CDCl$_3$) δ 0.98 (1H, d, J = 9.9 Hz), 1.13 (3H, s), 1.25 (3H, s), 1.40–1.92 (8H, m), 2.02 (1H, m), 2.18–2.41 (3H, m), 2.66 (2H, t, J = 6.9 Hz), 3.15 (1H, d, J = 14.7 Hz), 3.21 (1H, d, J = 14.7 Hz), 4.36 (1H, m), 6.24 (1H, d, J = 8.7 Hz), 7.40 (1H, dt, J = 1.2, 7.5 Hz), 7.45 (1H, dt, J = 1.2, 7.5 Hz), 7.85 (1H, s), 7.87 (1H, dd, J = 1.2, 7.5 Hz), 8.30 (1H, dd, 1.2, 7.5 Hz); IR (Nujol) 3425, 3091, 3059, 2632, 1726, 1608, 1522, 1261, 1250, 1215, 1126 cm$^{-1}$; $[α]_D^{26}$ + 34.0 ± 0.7° (c = 1.002, MeOH); Anal. (C$_{24}$H$_{31}$NO$_3$S$_2$) Calcd. (%): C, 64.68; H, 7.01; N, 3.14; S, 14.39 Found (%): C, 64.48; H, 7.01; N, 3.15; S, 14.25 |
| IIe-20 | mp 117–118° C.; $^1$H-NMR (CDCl$_3$) δ 0.98 (1H, d, J = 10.5 Hz), 1.14 (3H, s), 1.26 (3H, s), 1.40–1.92 (8H, m), 2.02 (1H, m), 2.18–2.42 (3H, m), 2.49 (3H, s), 2.66 (2H, t, J = 6.9 Hz), 3.16 (1H, d, J = 14.7 Hz), 3.21 (1H, d, J = 14.7 Hz), 4.35 (1H, m), 6.23 (1H, d, J = 8.7 Hz), 7.23 (1H, dd, J = 1.2, 8.4 Hz), 7.74 (1H, d, J = 8.4 Hz), 7.82 (1H, s), 8.11 (1H, d, J = 1.2 Hz); IR (Nujol) 3348, 1726, 1597, 1537, 1255, 1219 cm$^{-1}$; $[α]_D^{26}$ + 31.9 ± 0.7° (c = 1.002, MeOH); Anal. (C$_{25}$H$_{33}$NO$_3$S$_2$) Calcd. (%): C, 65.32; H, 7.24; N, 3.05; S, 13.95 Found (%): C, 65.15; H, 7.05; N, 3.10; S, 13.93 |
| IIe-21 | mp 170–172° C.; $^1$H-NMR (d$_6$—DMSO) δ 0.84 (1H, d, J = 9.9 Hz), 1.11 (3H, s), 1.18 (3H, s), 1.28–1.60 (7H, m), 1.94 (1H, m), 2.12–2.34 (6H, m), 2.55 (2H, t, J = 7.2 Hz), 3.17 (2H, s), 3.97 (1H, m), 6.79 (1H, d, J = 7.8 Hz), 7.24 (1H, t, J = 7.8 Hz), 7.78 (1H, d, J = 7.8 Hz), 7.98 (1H, d, J = 6.6 Hz), 8.18 (1H, s), 10.39 (1H, br), 12.46 (1H, br); IR (Nujol) 3357, 3246, 32613, 1693, 1595, 1574, 1541, 1469, 1296, 1228 cm$^{-1}$; $[α]_D^{27}$ + 38.7 ± 0.80 (c = 1.004, MeOH); Anal. (C$_{24}$H$_{31}$NO$_4$S$_2$) Calcd. (%): C, 62.44; H, 6.77; N, 3.03; S, 13.89 Found (%): C, 62.25; H, 6.86; N, 3.08; S, 13.60 |

TABLE 52

| Compound No. | Physical property |
| --- | --- |
| IIe-22 | $^1$H-NMR (CDCl$_3$) δ 0.93 (1H, d, J = 10.2 Hz), 1.10 (3H, s), 1.23 (3H, s), 1.36–1.92 (8H, m), 1.99 (1H, m), 2.16–2.39 (3H, m), 2.56 (2H, t, J = 7.2 Hz), 3.13 (2H, s), 4.32 (1H, m), 6.35 (1H, d, J = 9.0 Hz), 6.95 (1H, dd, J = 2.1, 9.0 Hz), 7.24 (1H, t, J = 2.1 Hz), 7.51 (1H, s), 8.03 (1H, d, J = 9.0 Hz); IR (KBr) 3361, 2661, 1707, 1603, 1523, 1468, 1236 cm$^{-1}$; $[α]_D^{26}$ + 23.2 ± 0.6° (c = 1.015, MeOH); Anal. (C$_{24}$H$_{31}$NO$_4$S$_2$.0.4H$_2$O) Calcd. (%): C, 61.48; H, 6.84; N, 2.99; S, 13.68 Found (%): C, 61.51; H, 6.74; N, 3.01; S, 13.67 |
| IIe-24 | $^1$H-NMR (CDCl$_3$) δ 0.96 (1H, d, J = 10.5 Hz), 1.15 (3H, s), 1.26 (3H, s), 1.40–1.92 (8H, m), 2.03 (1H, m), 2.18–2.42 (3H, m), 2.64 (2H, t, J = 7.2 Hz), 3.19 (2H, s), 4.29 (1H, m), 6.59 (1H, d, J = 8.4 Hz), 6.92 (1H, dd, J = 2.1, 6.6 Hz), 7.31 (1H, t, J = 2.1 Hz), 7.32 (1H, t, J = 6.6 Hz), 7.69 (1H, s), 12.22 (1H, s); IR (CHCl$_3$) 3508, 3452, 2683, 1711, 1624, 1585, 1562, 1523, 1456, 1271, 1227, 1217, 1205 cm$^{-1}$; $[α]_D^{26}$ + 34.1 ± 0.7° (c = 1.005, MeOH); Anal. (C$_{24}$H$_{31}$NO$_4$S) Calcd. (%): C, 62.44; H, 6.77; N, 3.03; S, 13.89 Found (%): C, 62.48; H, 6.86; N, 3.03; S, 13.63 |
| IIe-28 | mp 197–199° C.; $^1$H-NMR (CDCl$_3$) δ 0.98 (1H, d, J = 10.5 Hz), 1.14 (3H, s), 1.25 (3H, s), 1.40–1.92 (8H, m), 2.02 (1H, m), 2.18–2.41 (3H, m), 2.66 (2H, t, J = 6.9 Hz), 3.16 (1H, d, J = 15.0 Hz), 3.21 (1H, d, J = 15.0 Hz), 4.33 (1H, m), 6.19 (1H, d, J = 9.3 Hz), 7.16 (1H, td, J = 2.4, 8.7 Hz), 7.78 (1H, dd, J = 4.8, 8.7 Hz), 7.88 (1H, s), 8.07 (1H, dd, J = 2.4, 10.2 Hz); IR (Nujol) 3423, 3087, 2636, 1728, 1606, 1523, 1444, 1433, 1248, 1203, 1128 cm$^{-1}$; $[α]_D^{26}$ + 31.0 ± 0.7° (c = 1.013, MeOH); Anal. (C$_{24}$H$_{30}$FNO$_3$S$_2$.0.1AcOEt) Calcd. (%): C, 62.03; H, 6.57; F, 4.02; N, 2.96; S, 13.57 Found (%): C, 61.84; H, 6.48; F, 3.96; N, 2.98; S, 13.56 |
| IIe-34 | mp 143–144° C.; $^1$H-NMR (CDCl$_3$) δ 0.98 (1H, d, J = 10.2 Hz), 1.17 (3H, s), 1.24 (3H, s), 1.40–1.96 (8H, m), 2.02 (1H, m), 2.19–2.41 (3H, m), 2.64 (2H, t, J = 7.2 Hz), 3.15 (1H, d, J = 15.0 Hz), 3.20 (1H, d, J = 15.0 Hz), 4.41 (1H, m), 6.53 (1H, d, J = 8.7 Hz), 7.38 (1H, d, J = 5.4 Hz), 7.43 (1H, t, J = 7.8 Hz), 7.43 (1H, t, J = 7.8 Hz), 7.55 (1H, dd, J = 1.2, 7.8 Hz), 7.59 (1H, d, J = 5.4 Hz), 7.96 (1H, dd, J = 1.2, 7.8 Hz); IR (Nujol) 3421, 3402, 2625, 1712, 1618, 1579, 1529, 1250, 1215, 1120 cm$^{-1}$; $[α]_D^{26}$ + 48.2 ± 0.9° (c = 1.016, MeOH); Anal. (C$_{24}$H$_{31}$NO$_3$S$_2$) Calcd. (%): C, 64.68; H, 7.01; N, 3.14; S, 14.39 Found (%): C, 64.49; H, 6.85; N, 3.16; S, 14.12 |

TABLE 52-continued

| Compound No. | Physical property |
|---|---|
| IIe-54 | $^1$H-NMR (CDCl$_3$) δ 0.96 (1H, d, J = 10.2 Hz), 1.14 (3H, s), 1.24 (3H, s), 1.41–2.40 (12H, m), 2.64 (1H, t, J = 7.2 Hz), 3.19 (2H, s), 4.33 (1H, m), 6.14 (1H, d, J = 8.7 Hz), 7.12 (1H, dt, J = 6.0, 2.4 Hz), 7.25 (1H, dd, J = 8.4, 2.4 Hz), 7.81 (1H, dd, J = 8.4, 6.0 Hz), 8.09 (1H, s); IR (CHCl$_3$) 3446, 2674, 1710, 1654, 1563, 1506, 1490, 1257, 1220, 1205 cm$^{-1}$; [α]$_D^{26.0}$ + 22.8 ± 1.2° (c = 0.510, MeOH); Anal. (C$_{24}$H$_{30}$FNO$_4$S.0.2H$_2$O) Calcd. (%): C, 63.89; H, 6.79; F, 4.21; N, 3.10; S, 7.11 Found (%): C, 63.83; H, 6.93; F, 4.02; N, 3.18; S, 7.15 |

TABLE 53

| Compound No. | Physical property |
|---|---|
| IIf-28 | $^1$H-NMR (CDCl$_3$) δ 0.96 (1H, d, J = 9.9 Hz), 1.13 (3H, s), 1.25 (3H, s), 1.42–1.86 (9H, m), 2.02 (1H, m), 2.20–2.39 (4H, m), 4.31 (1H, m), 6.01 (1H, d, J = 8.7 Hz), 7.16 (1H, dt, J = 2.4, 9.0 Hz), 7.77 (1H, dd, J = 4.5, 9.0 Hz), 7.84 (1H, s), 8.08 (1H, dd, J = 2.4, 10.2 Hz); IR (CHCl$_3$) 3516, 3444, 1709, 1653, 1603, 1564, 1514, 1471, 1433, 1250, 1142 cm$^{-1}$; [α]$_D^{25}$ + 33.6 ± 0.7° (c = 1.007, MeOH) Anal. (C$_{23}$H$_{28}$FNO$_3$S.0.2H$_2$O) Calcd. (%): C, 65.60; H, 6.80; N, 3.33; F, 4.51; S, 7.61 Found (%): C, 65.70; H, 6.70; N, 3.28; F, 4.32; S, 7.56 |
| IIf-84 | $^1$H-NMR (CDCl$_3$) δ 0.95 (1H, d, J = 9.9 Hz), 1.10 (3H, s), 1.25 (3H, s), 1.32 (3H, t, d = 7.2 Hz), 1.44–1.86 (9H, m), 2.00 (1H, m), 2.21–2.39 (4H, m), 2.24 (2H, q, J = 7.2 Hz), 4.30 (1H, m), 6.15 (1H, m), 7.65 (1H, br d, J = 8.4 Hz), 7.76 (1H, d, J = 8.4 Hz), 7.78 (1H, s), 8.18 (1H, br s); IR (CHCl$_3$) 3510, 3437, 1713, 1651, 1606, 1570, 1514, 1441, 1319, 1225, 1207, 1169, 1155, 1080, 1066 cm$^{-1}$; [α]$_D^{24}$ + 26.3 ± 0.7° (c = 1.009, MeOH) Anal. (C$_{26}$H$_{34}$N$_2$O$_5$S.0.4H$_2$O) Calcd. (%): C, 63.24; H, 7.10; N, 5.67; S, 6.49 Found (%): C, 63.35; H, 6.88; N, 5.55; S, 6.34 |

The compounds prepared in Examples above were tested for determining the in vivo and in vitro activities according to the method as shown in Experimental examples below.

Experiment 1 Binding Activity to PGD$_2$ Receptor (1) Preparation of Human Platelet Membrane Fraction Blood was collected using a plastic syringe containing 3.8% sodium citrate from the vein of healthy volunteers (adult male and female), then put into a plastic test tube and mixed by slow-reversion. The sample was then centrifuged at 1800 rpm, for 10 min at room temperature, and the supernatant containing PRP (platelet-rich plasma) was collected. The PRP was re-centrifuged at 2300 rpm, for 22 min at room temperature to obtain platelets. The platelets were homogenized using a homogenizer (Ultra-Turrax) followed by centrifugation 3 times at 20,000 rpm, 10 min at 4° C. to obtain a platelet membrane fraction. After protein determination, the membrane fraction was adjusted to 2 mg/ml and preserved in a refrigerator at −80° C. until using for the binding test.

(2) Binding to PGD$_2$ Receptor

To a binding-reaction solution (50 mM Tris/HCl, pH 7.4, 5 mM MgCl$_2$) (0.2 ml) were added the human platelet membrane fraction (0.1 mg) and 5 nM [$^3$H]PGD$_2$ (115 Ci/mmol), and the mixture was reacted at 4° C. for 90 min. After the reaction, the mixture was filtered through a glass fiber filter paper and washed several times with cooled physiological saline, then the radioactivity retained on the filter paper was measured. The specific-binding ratio was calculated by subtracting the non-specific binding ratio which is the radioactivity similarly measured in the presence of 10 μM PGD$_2$ from the total binding. The inhibitory activity of each compound was expressed as the concentration required for 50% inhibition (IC$_{50}$), which was determined by depicting a substitution curve by plotting the binding ratio (%) in the presence of each compound, where the binding ratio in the absence of a test compound is 100%.

Experiment 2 Evaluation of Antagonistic Activity Against PGD$_2$ Receptor Using Human Platelet Peripheral blood was collected from a healthy volunteer using a syringe in which ⅑ volume of a citric acid/dextrose solution was previously added. The sample was subjected to centrifugation at 1200 rpm for 10 min to obtain the supernatant (PRP: platelet rich plasma). The resultant PRP was washed 3 times with a washing buffer and the number of platelets was counted with a micro cell counter. A suspension adjusted to contain the platelets at a final concentration of 5×10$^8$/ml was warmed at 37° C., then subjected to the pre-treatment with 3-isobutyl-1-methylxanthine (0.5 mM) for 5 min. To the suspension was added a test compound diluted at various concentration, and 10 minutes later, 0.1 μM PGD$_2$ was added to induce the reaction 2 minutes later, hydrochloric acid was added to terminate the reaction. The platelet was destroyed with an ultrasonic homogenizer. After centrifugation, the cAMP in the supernatant was determined by radioimmunoassay. PGD$_2$ receptor antagonism of a drug was evaluated as follows: the inhibition rate regarding cAMP increased by the addition of PGD$_2$ was determined at each concentration, and the concentration of the drug required for 50% inhibition (IC$_{50}$) was calculated.

The results of Experiment 1 and 2 are shown below.

TABLE 54

| Compound No. | Binding activity to PGD$_2$ receptor in human platelet membrane fraction IC$_{50}$ (μM) | Inhibitory activity for the increase of cAMP caused by PGD$_2$ in human platelet IC$_{50}$ (μM) |
|---|---|---|
| Ia-17 | | 0.011 |
| Ia-20 | | 0.017 |
| Ia-65 | | 0.018 |
| Ic-22 | | 0.010 |

TABLE 54-continued

| Compound No. | Binding activity to PGD$_2$ receptor in human platelet membrane fraction IC$_{50}$ (μM) | Inhibitory activity for the increase of cAMP caused by PGD$_2$ in human platelet IC$_{50}$ (μM) |
|---|---|---|
| Ic-23 | | 0.01 |
| Ic-52 | 0.074 | 0.01 |
| IIa-4 | | 0.019 |
| IIa-17 | | 0.015 |
| IIa-22 | | 0.0037 |
| IIa-23 | 0.033 | 0.0025 |
| IIa-28 | | 0.016 |
| IIa-34 | | 0.014 |
| IIa-52 | | 0.0037 |
| IIa-54 | | 0.015 |
| IIa-66 | | 0.017 |
| IIc-4 | | 0.018 |
| IIc-17 | | 0.0054 |
| IIc-20 | | 0.015 |
| IIc-22 | | 0.0046 |
| IIc-23 | 0.0095 | 0.0049 |
| IIc-24 | | 0.013 |
| IIc-28 | | 0.013 |
| IIc-34 | | 0.011 |
| IIc-52 | 0.0035 | 0.0082 |
| IIc-81 | | 0.008 |
| IIc-86 | | 0.008 |
| IIc-96 | | 0.017 |
| IIc-97 | | 0.011 |
| IIc-99 | | 0.006 |
| IIc-128 | | 0.005 |
| IIc-129 | | 0.018 |
| IIc-135 | | 0.003 |
| IIe-22 | | 0.0048 |
| IIe-24 | | 0.0057 |
| IIe-28 | | 0.017 |
| IIe-34 | | 0.019 |
| IIf-84 | | 0.020 |

Experiment 3 Change of Plasma Concentration of Drug in Rat

Compound (0.5 to 2 mg/kg) was administered intravenously to Jcl-SD male rats. The concentration of the unchanged compound was measured at 2, 5, 15, 30, 60, 120, and 240 min after the administration by the use of HPLC (determination limit; 0.05 μg/ml) and LC/MS/MS (determination limit; 0.001 μg/ml) and the half life of the disappearance was calculated.

Reference compound 1

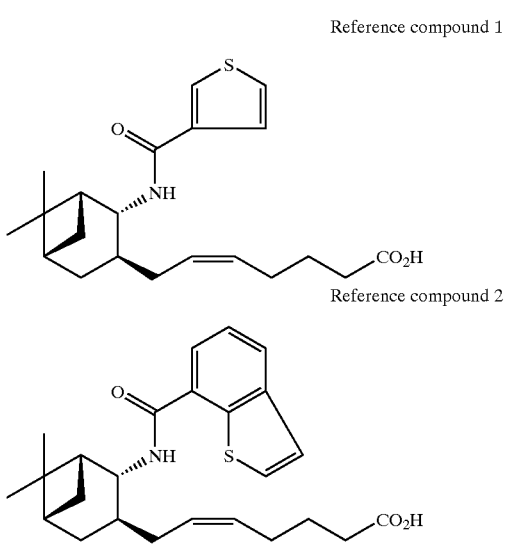

Reference compound 2

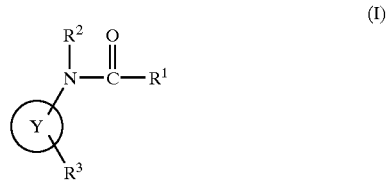

Reference compound 3

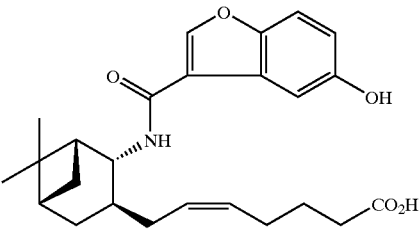

TABLE 55

| Compound No. | Half life of the disappearance (min) |
|---|---|
| Reference compound 1 | 8.0 |
| IIa-4 | 21.6 |
| IIc-4 | 44.3 |
| IIe-4 | 40.0 |
| Reference compound 2 | 17.0 |
| IIa-34 | 34.6 |
| IIc-34 | 66.7 |
| Reference compound 3 | 8.7 |
| IIa-52 | 16.7 |
| IIc-52 | 23.4 |

INDUSTRIAL APPLICABILITY

The compound of the present invention represented by the formula (I) having an antagonistic activity against PGD$_2$ receptor, is metabolically stable, and is useful in the improvement of conditions due to excessive production of PGD$_2$.

What is claimed is:

1. A compound represented by the formula (I):

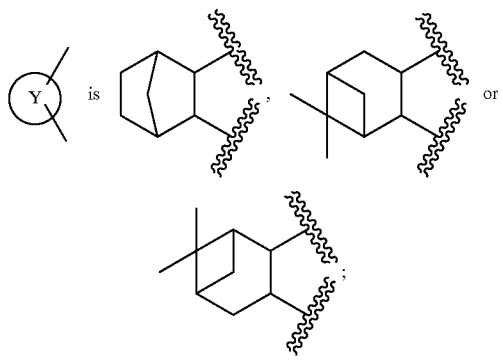

wherein $R^1$ is optionally substituted heteroaryl;
$R^2$ is hydrogen or alkyl;
$R^3$ is —$CH_2$—$CH_2$—$CH_2$—$CH_2$—CH=CH—$COOR^4$,
—$CH_2$—$CH_2$—$CH_2$—$CH_2$—$X^1$—$CH_2$—$COOR^4$,
—$CH_2$—CH=CH—$CH_2$—$X^1$—$CH_2$—$COOR^4$ or
—$CH_2$—$CH_2$—$CH_2$—$CH_2$—$COOR^4$;
$R^4$ is hydrogen or alkyl;
$X^1$ is —O— or —S—,
a prodrug, a pharmaceutically acceptable salt or a solvate thereof.

2. A compound as described in claim 1, wherein

is

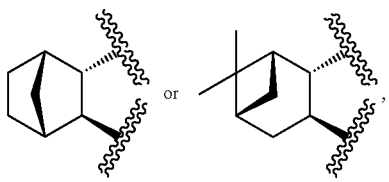

a prodrug, a pharmaceutically acceptable salt or a solvate thereof.

3. A compound as described in claim 1, wherein $R^1$ is heteroaryl which may be substituted with a group of the formula: -$Z^1$-$Z^2$ wherein $Z^1$ is a bond, —O—, —S—, —NH—, —NH—C(=O)—, —NH—C(=O)—O—, —NH—$SO_2$—, —O—C(=O)—, —C(=O)—O—, —$SO_2$—, —$CH_2$—O—, —$CH_2$—NH—C(=O)—, —$CH_2$—NH—C(=O)—O—, —$CH_2$—NH—$SO_2$— or —$CH_2$—C(O)— and $Z^2$ is alkyl or optionally substituted amino; carboxy; halogen; hydroxy; or nitro, a prodrug, a pharmaceutically acceptable salt or a solvate thereof.

4. A compound as described in claim 1, wherein $R^3$ is —$CH_2$—$CH_2$—$CH_2$—$CH_2$—CH=CH—$COOR^4$, —$CH_2$—$CH_2$—$CH_2$—$CH_2$—$X^1$—$CH_2$—$COOR^4$, —$CH_2$—CH=CH—$CH_2$—$X^1$—$CH_2$—$COOR^4$ or —$CH_2$—$CH_2$—$CH_2$—$CH_2$—$COOR^4$; $R^4$ is hydrogen; and $X^1$ is —O— or —S—, a prodrug, a pharmaceutically acceptable salt or a solvate thereof.

5. A compound as described in claim 4, wherein $R^3$ is —$CH_2$—$CH_2$—$CH_2$—$CH_2$—CH=CH—$COOR^4$ or —$CH_2$—$CH_2$—$CH_2$—$CH_2$—$X^1$—$CH_2$—$COOR^4$; $R^4$ is hydrogen; and $X^1$ is —O— or —S—, a prodrug, a pharmaceutically acceptable salt or a solvate thereof.

6. A pharmaceutical composition comprising an auxiliary component and a compound of Formula (I):

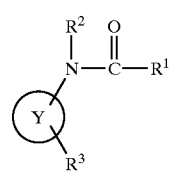
(I)

wherein

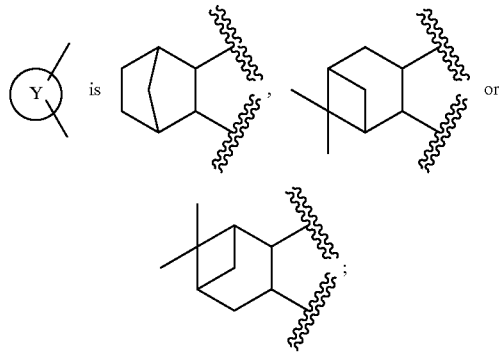

$R^1$ is optionally substituted heteroaryl;
$R^2$ is hydrogen or alkyl;
$R^3$ is —$CH_2$—$CH_2$—$CH_2$—$CH_2$—CH=CH—$COOR^4$,
—$CH_2$—$CH_2$—$CH_2$—$CH_2$—$X^1$—$CH_2$—$COOR^4$,
—$CH_2$—CH=CH—$CH_2$—$X^1$—$CH_2$—$COOR^4$ or
—$CH_2$—$CH_2$—$CH_2$—$CH_2$—$COOR^4$;
$R^4$ is hydrogen or alkyl;
$X^1$ is —O— or —S—,
a prodrug, a pharmaceutically acceptable salt or a solvate thereof.

7. A method for treating nasal blockage, allergic conjunctivitis or allergic rhinitis, which comprises administrating a compound of Formula (I):

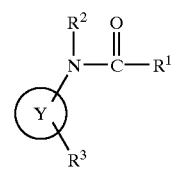
(I)

wherein

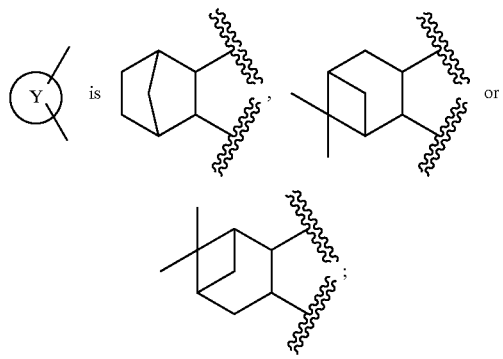

$R^1$ is optionally substituted heteroaryl;
$R^2$ is hydrogen or alkyl;
$R^3$ is —$CH_2$—$CH_2$—$CH_2$—$CH_2$—CH=CH—$COOR^4$,
—$CH_2$—$CH_2$—$CH_2$—$CH_2$—$X^1$—$CH_2$—$COOR^4$,
—$CH_2$—CH=CH—$CH_2$—$X^1$—$CH_2$—$COOR^4$ or
—$CH_2$—$CH_2$—$CH_2$—$CH_2$—$COOR^4$;
$R^4$ is hydrogen or alkyl;
$X^1$ is —O— or —S—,
a prodrug, a pharmaceutically acceptable salt or a solvent thereof.

8. A method of making a pharmaceutical composition for treating nasal blockage, allergic conjunctivitis or allergic rhinitis, comprising introducing to an auxiliary component a compound of claim 1.

9. A pharmaceutical composition of claim 6, wherein

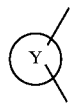

is

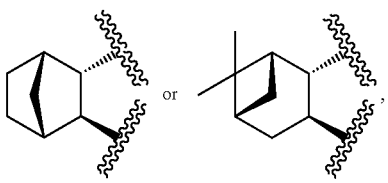

a prodrug, a pharmaceutically acceptable salt or a solvate thereof.

10. A pharmaceutical composition of claim 6, wherein $R^1$ is heteroaryl which may be substituted with a group of the formula: $-Z^1-Z^2$ wherein $Z^1$ is a bond, —O—, —S—, —NH—, —NH—C(=O)—, —NH—C(=O)—O—, —NH—SO$_2$—, —C(=O)—, —O—C(=O)—, —C(=O)—O—, —SO$_2$—, —CH$_2$—O—, —CH$_2$—NH—C(=O)—, —CH$_2$—NH—C(=O)—O—, —CH$_2$—NH—SO$_2$— or —CH$_2$—C(O)— and $Z^2$ is alkyl or optionally substituted amino; carboxy; halogen; hydroxy; or nitro, a prodrug, a pharmaceutically acceptable salt or a solvate thereof.

11. A pharmaceutical composition of claim 6, wherein $R^3$ is —CH$_2$—CH$_2$—CH$_2$—CH$_2$—CH=CH—COOR$^4$, —CH$_2$—CH$_2$—CH$_2$—CH$_2$—X$^1$—CH$_2$—COOR$^4$, —CH$_2$—CH=CH—CH$_2$—X$^1$—CH$_2$—COOR$^4$ or —CH$_2$—CH$_2$—CH$_2$—CH$_2$—COOR$^4$; R$^4$ hydrogen; and X$^1$ is —O— or —S—, a prodrug, a pharmaceutically acceptable salt or a solvate thereof.

12. A pharmaceutical composition of claim 11, wherein $R^3$ is —CH$_2$—CH$_2$—CH$_2$—CH$_2$—CH=CH—COOR$^4$ or —CH$_2$—CH$_2$—CH$_2$—CH$_2$—X$^1$—CH$_2$—COOR$^4$; R$^4$ is hydrogen; and X$^1$ is —O— or —S—, a prodrug, a pharmaceutically acceptable salt or a solvate thereof.

13. A method of claim 7, wherein

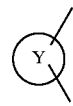

is

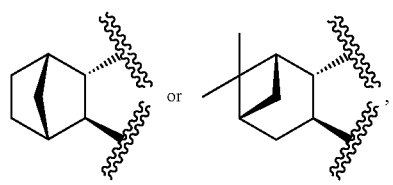

a prodrug, a pharmaceutically acceptable salt or a solvate thereof.

14. A method of claim 7, wherein $R^1$ is heteroaryl which may be substituted with a group of the formula: $-Z^1-Z^2$ wherein $Z^1$ is a bond, —O—, —S—, —NH—, —NH—C(=O)—, —NH—C(=O)—O—, —NH—SO$_2$—, —C(=O)—, —O—C(=O)—, —C(=O)—O—, —SO$_2$—, —CH$_2$—O—, —CH$_2$—NH—C(=O)—, —CH$_2$—NH—C(=O)—O—, —CH$_2$—NH—SO$_2$— or —CH$_2$—C(O)— and $Z^2$ is alkyl or optionally substituted amino; carboxy; halogen; hydroxy; or nitro, a prodrug, a pharmaceutically acceptable salt or a solvate thereof.

15. A method of claim 7, wherein $R^3$ is —CH$_2$—CH$_2$—CH$_2$—CH$_2$—CH=CH—COOR$^4$, —CH$_2$—CH$_2$—CH$_2$—CH$_2$—X$^1$—CH$_2$—COOR$^4$, —CH$_2$—CH=CH—CH$_2$—X$^1$—CH$_2$—COOR$^4$ or —CH$_2$—CH$_2$—CH$_2$—CH$_2$—COOR$^4$; R$^4$ is hydrogen; and X$^1$ is —O— or —S—, a prodrug, a pharmaceutically acceptable salt or a solvate thereof.

16. A method of claim 15, wherein $R^3$ is —CH$_2$—CH$_2$—CH$_2$—CH$_2$—CH=CH—COOR$^4$ or —CH$_2$—CH$_2$—CH$_2$—CH$_2$—X$^1$—CH$_2$—COOR$^4$; R$^4$ is hydrogen; and X$^1$ is —O— or —S—, a prodrug, a pharmaceutically acceptable salt or a solvate thereof.

* * * * *